(12) United States Patent
Hansson et al.

(10) Patent No.: US 6,222,094 B1
(45) Date of Patent: Apr. 24, 2001

(54) TRANSGENIC NON-HUMAN MAMMAL EXPRESSING THE DNA SEQUENCE ENCODING KAPPA CASEIN MAMMARY GLAND AND MILK

(75) Inventors: Lennart Hansson; Mats Strömqvist; Sven Bergström; Olle Hernell, all of Umeå ; Jan Törnell, Västra, all of (SE)

(73) Assignee: Symbicom Aktiebolag, Umea (SE)

( * ) Notice: Subject to any disclaimer, the term of this patent is extended or adjusted under 35 U.S.C. 154(b) by 0 days.

(21) Appl. No.: 08/256,799

(22) PCT Filed: Jan. 25, 1993

(86) PCT No.: PCT/DK93/00024

§ 371 Date: Dec. 6, 1994

§ 102(e) Date: Dec. 6, 1994

(87) PCT Pub. No.: WO93/15196

PCT Pub. Date: Aug. 5, 1993

(30) Foreign Application Priority Data

Jan. 23, 1992 (SE) ..................................... 0088/92

(51) Int. Cl.$^7$ ......................... A01K 67/027; C12P 21/00; C12N 15/00

(52) U.S. Cl. ................................. 800/14; 800/7; 800/14; 800/15; 800/16; 800/17; 800/18; 800/25; 526/580; 526/801; 526/72

(58) Field of Search ............... 800/2; 435/69.1, 435/172.3

(56) References Cited

U.S. PATENT DOCUMENTS

| | | |
|---|---|---|
| 4,736,866 | 4/1988 | Leder et al. . |
| 4,873,316 | 10/1989 | Meade et al. . |
| 5,391,497 | 2/1995 | Menon et al. ..................... 435/320.1 |
| 6,020,015 | * 1/2000 | Gaull ..................................... 426/580 |

FOREIGN PATENT DOCUMENTS

| | | |
|---|---|---|
| 0181634 A2 | * 5/1986 | (EP) ............................. C12N/15/00 |
| 0247494 | 5/1987 | (EP) . |
| 0264166 | 4/1988 | (EP) . |
| 0279582 | 8/1988 | (EP) . |
| 8204443 | 12/1982 | (WO) . |
| 8800239 | 1/1988 | (WO) . |
| 8801648 | 3/1988 | (WO) . |
| 9103551 | 3/1991 | (WO) . |
| 9108216 | 6/1991 | (WO) . |
| 9108675 | 6/1991 | (WO) . |

OTHER PUBLICATIONS

Brignon et al. (1985) Febs Le H. 188, 48–54.*
Lee et al. (1988) Nucleric Acids Res. 16, 1027–1041.*
Dialog Information Services, file 350, World Patent Index, Dialog accession No. 002266417, *Synthetic Milk with Similar Protein Content to Human Milk*...

Menon et al., Swissprot Database, accession No. PO7498, *Kappa Casein Precursor*, Aug. 1, 1992.

Brignon, et al., *Preparation and Amino Acid Sequence of Human k–casein*, Febs, vol. 188, No. 1, pp. 48–54, Aug. 1985.

Brinster, et al., *Introns Increase Transcriptional Efficiency in Transgenic Mice*, Proc. Natl. Acad. Sci. USA, vol. 85, pp. 836–840, Feb. 1988.

Hennighausen, *The Mammary Gland as a Bioreactor: Production of Foreign Proteins in Milk*, Protein Expression and Purification, vol. 1, pp. 3–8, 1990.

Cheung, et al., *Nucleotide sequence of cloned cDNA of human apolipoprotein A–1*, Nucleic Acids Research, vol. 11, No. 11, pp. 3703–3715, 1983.

Mercier, et al., *Construction and identification of recombinant plasmids carrying cDNAs coding for ovine $\alpha_{s1}$–, $\alpha_{s2}$–, β–, κ–Casein and β–lactoglobulin. Nucleotide sequence of $\alpha_{s1}$–casein cDNA*, BIOCHIMIE, vol. 67, pp. 959–971, 1985.

Palmitter, et al., *Heterologous introns can enhance expression of transgenes in mice*, Proc. Natl. Acad. Sci., USA, vol. 88, pp. 478–482, Jan. 1991.

(List continued on next page.)

Primary Examiner—Deborah Crouch
(74) Attorney, Agent, or Firm—Iver P. Cooper

(57) ABSTRACT

The present invention relates to an expression system comprising a DNA sequence encoding a polypeptide which ha a biological activity of human κ-casein, the system comprising a 5'-flanking sequence capable of mediating expression of said DNA sequence. In preferred embodiments the 5'-flanking sequence is from a milk protein gene of a mammal such as a casein gene or whey acidic protein (WAP) gene and the DNA sequence contains at least one intron sequence. The invention further relates to DNA sequences, replicable expression vectors and cells harboring said vectors, recombinant polypeptide e.g. in glycosylated form, and milk, infant formula or nutrient supplement comprising recombinant polypeptide. The invention also relates to a method for producing a transgenic non-human mammal comprising injecting an expression system as defined above and optionally a further DNA encoding β-casein or an analog, variant or subsequence thereof into a fertilized egg or a cell of an embryo of a mammal so as to incorporate the expression system into the germline of the mammal and developing the resulting injected fertilized egg or embryo into an adult female mammal. In one embodiment, the endogenous polypeptide expressing capability of the mammal is destroyed and/or replaced with the expression system defined above. The invention further relates to a transgenic non-human mammal such as a mouse, rat, rabbit, goat, sheep, pig, lama, camel or bovine species whose germ cells a somatic cells contain a DNA sequence as defined above as a result of chromosomal incorporation into the non-human mammalian genome, or into the genome of an ancestor of said non-human mammal.

26 Claims, 18 Drawing Sheets

OTHER PUBLICATIONS

Figure 1:
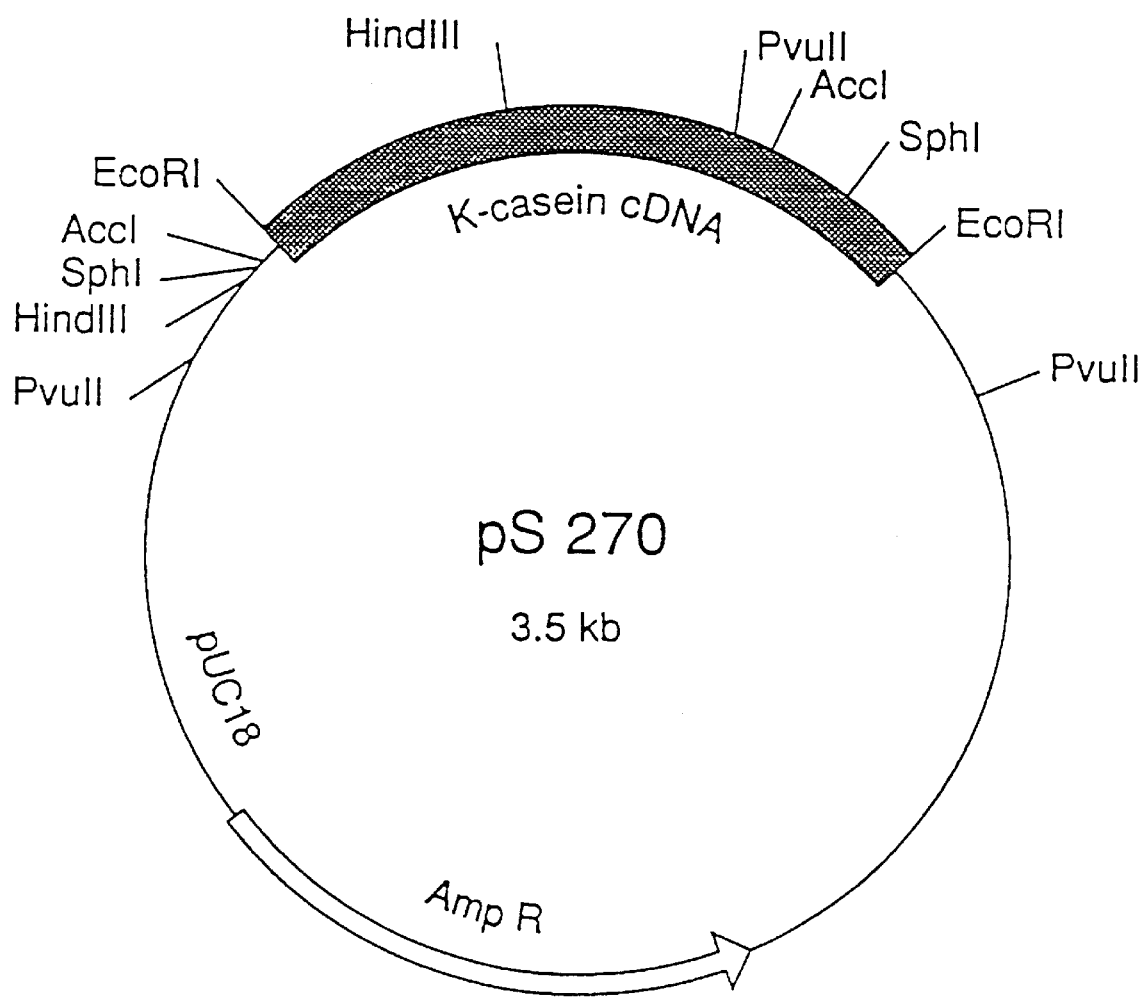

Rosen, et al., *Isolation and Characterization of the Rat Proenkephalin Gene*, The Journal of Biological Chemistry, vol. 259, No. 22, pp. 14309–14313, Nov. 25, 1984.

Stewart, et al., *Nucleotide sequences of bovine $\alpha_{s1}$–and $\alpha$–casein cDNAs*, Nucleic Acids Research, vol. 12, No. 9, pp. 3895–3907, 1984.

Sudhof, et al., *Human 67–kDa calelectrin contains a duplication of four repeats found in 35–k–Da lipocortins*, Proc. Natl. Acad. Sci. USA, vol. 85, pp. 664–668, Feb. 1988.

Taniguchi, et al., *Structure and expression of a cloned cDNA for human interleukin–2*, Nature, vol. 302, pp. 305–310, Mar. 24, 1983.

Whitelaw, et al., *Targeting expression to the mammary gland: intronic sequences can enhance the efficiency of gene expression in transgenic mice*, Transgenic Research, vol. 1, pp. 3–13, 1991.

Alexander et al., *Isolation and Characterization of the Bovine k–Casein Gene*, Eur. J. Biochem., vol. 178, pp. 395–401, 1988.

Geneseq Protein Sequence Database, Menon et al., *Homo Sapiens Kappa–Casein mRNA, complete cds*, accession No. M73628, Jul. 23, 1991.

Widera et al., *Transgenic Mice Selectively Lacking MHC Class II (I–E) Antigen Expression on B Cells: An i vivo Approach to Investigate Ia Gene Function*, Cell, vol. 51, pp. 175–187, Oct. 23, 1987.

Bergstrom, et al., *Cloning and sequencing of human K–casein cDNA*, J. DNA Sequencing and mapping, vol. 3, pp. 245–246, 1992.

Fiat, et al., *Caseins of various origins and biologically active casein peptides and oligosacchardies: Structural and physiological aspects*, Molecular and Cellular Biochemistry, vol. 87, pp. 5–30, 1989.

Jolles, et al., *Immunostimulating Substances from Human Casein*, Journal of Immunopharmacology, vol. 3, pp. 363–369, 1981–1982.

Aniansson, et al., *Anti–adhesive activity of human casein against Streptococcus pneumoniae and Haemophilus influenzae*, Microbial Pathogenesis, vol. 8, pp. 315–323, 1990.

Axelsson, et al., *Bovine $\beta$–Lactoglobulin in the Human Milk*, Acta Paediatr Scand, vol. 75, pp. 702–707, 1986.

Azuma, et al., *Bifidus Growth–promoting Activity of a Glycomacropeptide Derived from Huamn k–Casein*, Agric. Biol. Chem., vol. 48(8), pp. 2159–2162, 1984.

Bezkorovainy, et al., *Isolation of a glycopolypeptide fraction with Lactobacillus bifidus subspecies pennsylvanicus growth–promoting activity from whole human milk casein*, The American Journal of Clinical Nutrition, vol. 32, pp. 1428–1432, Jul. 1979.

Chiba, et al., *Opioid antagonist peptides dervied from K–casein*, J. Dairy Res., vol. 56, pp. 363–366, 1989.

Fiat, et al., *Localisation and Importance of the Sugar Part of Human Casein*, Eur. J. Biochem, vol. 111, pp. 333–339, 1980.

Fitzgerald, et al., *Bindings of Ions and Hydrophobic Probes to $\alpha$–Lactalbumin and k–Casein as Determined by Analytical Affinity Chromatography*, Archives of Biochemistry and Biophysics, vol. 268, No. 1, pp. 239–248, 1989.

Hall, et al., *Organization and sequence of the human $\alpha$–lactalbumin gene*, Biochem. J., vol. 242, pp. 735–742, 1987.

Hambr↑us, et al., *Nutritional Aspects of Breast Milk Versus Cow's Milk Formula*, Food and Immunology, Almquist and Wiksell, pp. 116–124, 1977.

Hammer, et al., *Production of transgenic rabbits, sheep and pigs by microinjection*, Nature, vol. 315, pp. 680–683, Jun. 20, 1985.

Jollès, et al., *Analogy between fibrinogen and casein*, Eur. J. Biochem., vol. 158, pp. 379–382, 1986.

Lönnerdal, et al., *Cloning and sequencing of cDNA encoding human milk $\beta$–casein*, Febs, vol. 269, No. 1, pp. 153–156, Aug. 1990.

Maruyama, et al., *Studies on the Active Site and Antihypertensive Activity of Angiotension I–Converting Enzyme Inhibitors Derived from Casein*, Agric. Biol. Chem., vol. 51, No. 6, pp. 1581–1586, 1987.

Menon, et al., *Human $\beta$–casein: partial cDNA sequence and apparent polymorphism*, Nucleic Acids Research, vol. 17, No. 7, pp. 2869, 1989.

Miller, et al., *Casein: A Milk Protein with Diverse Biologic Consequences*, Proc. Soc. Exp. Biol. Med., vol. 195, pp. 143–159, 1990.

Newport, et al., *Evaluation of the Neonatal Pig As a Model for Infant Nutrition: Effects of Different Proportions of Casein and Whey Protein in Milk on Nitrogen Metabolism and Compostion of Digesta in the Stomach*, Pediatric Research, vol. 18, No. 7, pp. 658–662, 1984.

Nilsson, et al., *cDNA cloning of human–milk bile–saltstimulated lipase and evidence for its identity to pancreatic carboxylic ester hydrolase*, Eur. J. Biochem., vol. 192, pp. 543–550, 1990.

Powell, et al., *Nucleotide sequence of human lactogerrin cDNA*, Nucleic Acids Research, vol. 18, No. 13, p. 4013, 1990.

Stan, et al., *Formation of a Peptide Inhibitor of Gastric Secretion*, Bull Exp. Biol. Med., vol. 94, pp. 1087–1089, 1982.

Yvon, et al., *Characterization and Kinetics of Evacuation of Peptide Resulting from Casein Hydrolysis in the Stomach of the Calf*, J. Agric. Food Chem., vol. 35, pp. 148–156, 1987.

* cited by examiner pS459 subclones 1 kb pS 460 subclones

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 857 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (vi) ORIGINAL SOURCE:
      (A) ORGANISM: Homo sapiens (ix) FEATURE:
      (A) NAME/KEY: CDS
      (B) LOCATION: 45..593

(ix) FEATURE:
      (A) NAME/KEY: mat_peptide
      (B) LOCATION: 45..593

(ix) FEATURE:
      (A) NAME/KEY: sig_peptide
      (B) LOCATION: 45..104

(ix) FEATURE:
      (A) NAME/KEY: 5'UTR
      (B) LOCATION: 13..44

(ix) FEATURE:
      (A) NAME/KEY: 3'UTR
      (B) LOCATION: 594..848

(xi) SEQUENCE DESCRIPTION: SEQ ID NO: 1:

```
GAATTCCGAG AGAAGACCTG ACTGGCACGA GGAAAGGTGC AATA ATG AAG AGT TTT        56
                                              Met Lys Ser Phe
                                                1

CTT CTA GTT GTC AAT GCC CTG GCA TTA ACC CTG CCT TTT TTG GCT GTG       104
Leu Leu Val Val Asn Ala Leu Ala Leu Thr Leu Pro Phe Leu Ala Val
 5              10              15              20

GAG GTT CAA AAC CAG AAA CAA CCA GCA TGC CAT GAG AAT GAT GAA AGA       152
Glu Val Gln Asn Gln Lys Gln Pro Ala Cys His Glu Asn Asp Glu Arg
             25              30              35

CCA TTC TAT CAG AAA ACA GCT CCA TAT GTC CCA ATG TAT TAT GTG CCA       200
Pro Phe Tyr Gln Lys Thr Ala Pro Tyr Val Pro Met Tyr Tyr Val Pro
         40              45              50

AAT AGC TAT CCT TAT TAT GGA ACC AAT TTG TAC CAA CGT AGA CCA GCT       248
Asn Ser Tyr Pro Tyr Tyr Gly Thr Asn Leu Tyr Gln Arg Arg Pro Ala
     55              60              65

ATA GCA ATT AAT AAT CCA TAT GTG CCT CGC ACA TAT TAT GCA AAC CCA       296
Ile Ala Ile Asn Asn Pro Tyr Val Pro Arg Thr Tyr Tyr Ala Asn Pro
 70              75              80

GCT GTA GTT AGG CCA CAT GCC CAA ATT CCT CAG CGG CAA TAC CTG CCA       344
Ala Val Val Arg Pro His Ala Gln Ile Pro Gln Arg Gln Tyr Leu Pro
 85              90              95             100
```

```
AAT AGC CAC CCA CCC ACT GTG GTA CGT CGC CCA AAC CTG CAT CCA TCA       392
Asn Ser His Pro Pro Thr Val Val Arg Arg Pro Asn Leu His Pro Ser
            105                     110                 115

TTT ATT GCC ATC CCC CCA AAG AAA ATT CAG GAT AAA ATA ATC ATC CCT       440
Phe Ile Ala Ile Pro Pro Lys Lys Ile Gln Asp Lys Ile Ile Ile Pro
        120                 125                 130

ACC ATC AAT ACC ATT GCT ACT GTT GAA CCT ACA CCA GCT CCT GCC ACT       488
Thr Ile Asn Thr Ile Ala Thr Val Glu Pro Thr Pro Ala Pro Ala Thr
            135                 140                 145

GAA CCA ACG GTG GAC AGT GTA GTC ACT CCA GAA GCT TTT TCA GAG TCC       536
Glu Pro Thr Val Asp Ser Val Val Thr Pro Glu Ala Phe Ser Glu Ser
        150                 155                 160

ATC ATC ACG AGC ACC CCT GAG ACA ACC ACA GTT GCA GTT ACT CCA CCT       584
Ile Ile Thr Ser Thr Pro Glu Thr Thr Thr Val Ala Val Thr Pro Pro
165             170                 175                 180

ACG GCA TAAAACACC AAGGAAATAT CAAAGAACAC AACGCAGGAC TTGCTGAAAC         640
Thr Ala

CAAATTACTA CTTCACACTC TCCTTCAGCC ATTTGTCTGC CTTCAGTCAA CAGAAAATGT    700

GATTTTCACA GATTCAGCTC TTCTCTCCTT ACATTTTACA TTCATGCCAC ATTCAATATT    760

TTGATTCTTG CACAATAAAG CCAACTGATT GCAAAAAAAA AAAAAAAAAA AAAAAAAAA     820

AAAAAAAAAA AAAAAAAAAA AAAAAAACC GGAATTC                              857

(2) INFORMATION FOR SEQ ID NO: 2:

(i) SEQUENCE CHARACTERISTICS:
        (A) LENGTH: 182 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Ser Phe Leu Leu Val Val Asn Ala Leu Ala Leu Thr Leu Pro
 1               5                  10                  15

Phe Leu Ala Val Glu Val Gln Asn Gln Lys Gln Pro Ala Cys His Glu
            20                  25                  30

Asn Asp Glu Arg Pro Phe Tyr Gln Lys Thr Ala Pro Tyr Val Pro Met
        35                  40                  45

Tyr Tyr Val Pro Asn Ser Tyr Pro Tyr Tyr Gly Thr Asn Leu Tyr Gln
    50                  55                  60

Arg Arg Pro Ala Ile Ala Ile Asn Asn Pro Tyr Val Pro Arg Thr Tyr
65                  70                  75                  80

Tyr Ala Asn Pro Ala Val Val Arg Pro His Ala Gln Ile Pro Gln Arg
                85                  90                  95

Gln Tyr Leu Pro Asn Ser His Pro Pro Thr Val Val Arg Arg Pro Asn
            100                 105                 110

Leu His Pro Ser Phe Ile Ala Ile Pro Pro Lys Lys Ile Gln Asp Lys
        115                 120                 125

Ile Ile Ile Pro Thr Ile Asn Thr Ile Ala Thr Val Glu Pro Thr Pro
    130                 135                 140

Ala Pro Ala Thr Glu Pro Thr Val Asp Ser Val Val Thr Pro Glu Ala
145                 150                 155                 160

Phe Ser Glu Ser Ile Ile Thr Ser Thr Pro Glu Thr Thr Thr Val Ala
                165                 170                 175

Val Thr Pro Pro Thr Ala
            180
```

(2) INFORMATION FOR SEQ ID NO: 3:

(i) SEQUENCE CHARACTERISTICS:
        (A) LENGTH: 2241 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:
        (B) CLONE: ps460

(ix) FEATURE:
        (A) NAME/KEY: intron
        (B) LOCATION: 46..2186

(ix) FEATURE:
        (A) NAME/KEY: exon
        (B) LOCATION: 1..45

(ix) FEATURE:
        (A) NAME/KEY: exon
        (B) LOCATION: 2187..2241

(xi) SEQUENCE DESCRIPTION: SEQ ID NO: 3:

```
CAGCTCAACC TACTGCCAAC CAAGACCTGA CTGGCACGAG GAAAGGTAAT GCTGCTGAAA     60

CACTTGGAGA AAGTGATCCT TTTCACAGTA GTTAGTTGGG ACATCACCAT AGTTATTTCA    120

GAATCACATT TTCTTCCTTT TAGTTATTGT TAAGTTTGAA TATGACCTAG CATCACTTTA    180

AAATTAATTT CTAACCTAAA CCTAAGTTCT GGATGGTGTT ATGTTCAAAT TTATTTTTAA    240

CTTTACTTTG GGTTCCAGTC AAATTCTGAT ACCAACTAAA TCATAGCAGC CATTGTGAAT    300

TCCGAACAAG AAGGCGTTTA ACGTATTCCT ACAGACAAAT GTTGAGAGTT AACTCTACAG    360

GAAGTTGGGC TCATGATAAT AATCGCAATT AACCCCTTAA TTACTTTCAA ATTTTATTTC    420

TATAAAAGTC ATAATTTTAT TTGTTATGGA ATAATTATTT TTTTAAAACA TGTTTTTCAA    480

ATATTCATGA AAGCTGGATA ATTCTACCAT TTCACGAATT ATTTCTTCTT ACCAAGTGAT    540

GAGGGCAAAT GCAAATGTAG CTGATACGCA AAGTATGGTC TTATCTCTGT GATTTTTGTT    600

TGTGCCAAAA GGAAATTACT ATCATTTTAT AGAATATTTT CTTTTGTTTA CATATCATTT    660

TACTGTGTGA ACTGATAAGG GGTCTGTGAT TCATCATAAA AACATTTTCA GTCTATAATC    720

CTAAAAGATC ACTAGCAAGT GAAGCATTAA TAAGGAGCTT CATCCCACTT AAAGAAATAT    780

GAGTGTGCTT AGATTGTTCA AATTGATTCC AAATGAGTTC CATCAAATGG AAATTTGATG    840

ACATCGTATG GGCAGTTTTG AAGTCACTTT AGTAGACAGC CTTCCTAATC ATTATTGCCT    900

GAGAATCAGA CGCTAATGGA GTCCAGTGGG CTTTCCATCC CCTATCTGAG GCTTTAATTC    960

TGTGAATCTT TTTTGCGAAG TTCAACTTTG TAGTGATTCA AGTTTATATG AGTGTGTCAA   1020

TAACAATAGC TGCAACAAGA TGAAGTTAGT AATTACTTCC TAAACATAAT ATATACTTAA   1080

ATATAAAAGT TTGGGTATCA TATATTATTA GTCTAAAAGA TGATTTATTA AAAATCAAAT   1140

AAGCAGTATG ACACTGTATA TACTCTTTTA GAAAAATAAG GCTAATGTAT TTCTTTAAAT   1200

ATTTTAGTCA AAGCCACTGT AATTGTGATC TCTATACTTC TTATTAAAAC AATCAAGGTT   1260

AATCATATCA GGTTATGATT ACTGGAGAAG TATGTTATAA AGAAACAGT CTCATAACCC    1320

TCCACTTCCC ATTCCATCCT ACATACTTCT GTTGGATTGA TCATGGAATT ATAGAATTTT   1380

AGAAATCTCT AAGTTCAAAC CCTGGTTTTA CAGGTAAGAA AATGTAAAGC CCAGGAAAGG   1440
```

```
AAATCACTTG ATCAAAGTTA CAGAGGTAGA GATAAGGCCT GGTCTAGAAT TCAGTCCTCC      1500

AAAAAATGTA TAGTCATACA CTTTCTAGTC CAAAAACACT CAATTGTTTT CTGTTGTTTA      1560

TAAAGCCATG CCTAGCTTTT TAACCCATCA TTATCTTAAA GGTGTCTACT TTTTCTGCTC      1620

TAAACTTTCC TTCCAATCTT ATATTTCCCT TCTCATACAA GATTCCAATC AAATGTTCAT      1680

GGCGATTCTC AAGACTTTCT CCTCTACTTG AAATATTTCT CTCCCTGTTA AATACTGCAT      1740

AGGCAAGCCT CATCTATATG TCATTTTTTC CACACAAAGA CTGCTGCTTC TCTTAACTGA      1800

AACTTTTATT AATAGAAAAC CACTTTTGTG CATTTTCTAC TTTTTTTCCC TCTTACAGTT      1860

GTTTTTCAGT ATATGTTTCA ACGCTCTTCC TAAAATTGAT GCTACTCATT GCAAGGCCTG      1920

TATCATATTT ACATTGATAA TCTCAACATT TGACATAGTA ATGATAATTT GATAATTCCG      1980

TTAATATTGT CAAAAATTAA ATTCAGAAAT TTTTACTCCA AGTTTGAGTT TTTACATTCT      2040

TTTGTTAAAA TAAATTTTTC ACATCGGCTA AATCTACCTG TAAATCTGGC TTTTTTTCTT      2100

AATCAAGGAA ACATTGTATT CAAGTCACTC CTAAATTTCT AGTAACAAAT TCTTTTAAAT      2160

TAATTTTTTT TTAAATTTAT CTTTAGGTGC AATAATGAAG AGTTTTCTTC TAGTTGTCAA      2220

TGCCCTGGCA TTAACCCTGC C                                                 2241

(2) INFORMATION FOR SEQ ID NO: 4:

(i) SEQUENCE CHARACTERISTICS:
        (A) LENGTH: 13104 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:
        (B) CLONE: ps459

(ix) FEATURE:
        (A) NAME/KEY: intron
        (B) LOCATION: 1..8834

(ix) FEATURE:
        (A) NAME/KEY: intron
        (B) LOCATION: 8868..10014

(ix) FEATURE:
        (A) NAME/KEY: intron
        (B) LOCATION: 10511..12277

(ix) FEATURE:
        (A) NAME/KEY: exon
        (B) LOCATION: 8835..8867

(ix) FEATURE:
        (A) NAME/KEY: exon
        (B) LOCATION: 10015..10510

(ix) FEATURE:
        (A) NAME/KEY: exon
        (B) LOCATION: 12278..12443

(xi) SEQUENCE DESCRIPTION: SEQ ID NO: 4:

GATCTCTTCA AATTCTTGAT GGTCACCTTG GACAAGAGAC TTCACTTGTA TATGTGGATA        60

GTGACAAATG GGAGGACAAT ATCCATTGCT TTTTCTATTT TTTTTTTTTT TTTTCGGGAT       120

GGAGTTTCAC TCGTGTTGCC CAGGCTGGAG TGCAATGGTG CAATCTCGGC TCACTGCAAC       180

CTCTGCCTCC CGGGTTCAAG CAACTCTCCT GCCTCAGCCT CCTGAGTAGC TGGGATTACA       240
```

-continued

```
GGCGCCTGCA CCATGCCTGG CTAATTTTTT GTATTTTTAG TAAGGATGGA GTTTCACCAT     300

GTTGGCCAGG CTGGTCTGGA ACTCCTGACC TCAGATGATC CACCCGCCTC GGCCTCCCAA     360

AATGCTGGGA TTACAGGCGT GAGCCACTAC GTCCGGCCTG CTCTTTCTTT GACTGATGAG     420

CTTTCTTTTT TTGCCATTGG ACATAATTCA GATAATTCCA TCTCTAAAGT GTCCTTCAAG     480

GGCACTTAGT TCAATCTGAC AGCTATCACT TTTCTTTTCA TTGACAAATG TAATGTTCAT     540

ATTCCTTATA ATAATTTGAA TGAATTTGAA AGGATTACAG ATCTTAATTA AATTTTGTAT     600

ATCATCAATA TTTCAAAATA ATAATGAAGC TTTTCCTTAG GAATACACAG ATATTGCTCT     660

ACTGATCTTA ATAATCATTC TTAAAATTTA ATAAAATTGC TAGTGAATCA TTTTAACCTC     720

TTTTTAAGGT TGAATTTTTG TTTTTAAATG TATAAACTTT GTTAGTACAT TATATATTTC     780

ACGTAGCCCT TGCAATTTTC AATTAAGACA TTCAAGTAGG TGTTTAGCAA GATCTAGCCT     840

TTTTTGAAGC CAATAATGAT CCCTCAAAAT ATTTTCAAAG TAAGCATAAT TCATAGCATA     900

GTTTTAAATC TAGTTTTTAG CTAATAAACT CTGTAAAATT CTTGCGCAGT TAACCCACTT     960

TAGGATGAAA GAGCAGGGAG AGGTCTCCTG AACCCATTTC TTCACCAAAA GCTATAAAGA    1020

GAAGGAGTTA TACAGGTTTG AATGTTATTG GAGTCACTTT TTAAAAATAA CAACCTTTTT    1080

GTGGAATGCA GATTCACAGG CAAACCTTTA TATGATGAAC TTTTTCTCTG AATAAATATT    1140

ATTTGAATCT CAAGATTTTC AGAAAGAGCT TGATGTAAAG CCTTTACACT TTCTTGTCAT    1200

TGTAGCTGTA CTATCAGTAC ATGAACTTGG ACATTCAAAA TCTGACTTCA GAGTTTAACT    1260

GTGTATAGAA TTCATACACT ATAAAGTTTA TACATTTAAT TGTGTACACT TATTTTGTGC    1320

AGTGCTTTCA GAATCTATTT TGACATGTTT ATTTACTTCT TTGAATGTTT CATCCCCAAC    1380

AAATTGGTTT GGTTCTTCTT TGTAAGACAG ATGATATTAT TCCAAGCATT TCTGGTCAGG    1440

GTTTCTAACT GGTGCCATCA ACCACACCCA GTTACTAACG TCTGTGATAC TAATATCCAG    1500

TACGCACAAC CCTGAGAGAG GGGGAAGAAA GGAGAGAAAA TGCTAAGATA AGTTTTTAGT    1560

AAGCTGGAGG CTGGGAACTC AATGTTCAGG AGCCTATTCC AGAAGCCAAA AGAGTCATCA    1620

AAGAAAGTGG GAAAGGGGTC TGACTGGAAG GGACCAGGAA CAGGCTGGTC AGGAGGCAGG    1680

GAAAGCCTAG AGATGACCTG AGCTCCAACA GAGCAGAAGA CAAGAGGAGG CTTCTTGGAA    1740

AACAACTGCT GTTTGGCTGA GGCTAAAGGT CAAGCCACAT TTTGAATCAC CCATCTGGAG    1800

GTCACCTTGC TCCATTCTTC ATCTTAAAGT GATGTAGACC AGCTCTCCAA GAGAGGAAGG    1860

GAAGCTCCTG ACACAGGCCT AAGCCATTCT TTCCAACAGG GTGGGAGTTC ATGGAGGGGA    1920

AGAGAAATTC ATCAGGGACA TGGGGATTGG AAAAGAGGGG GATAGAGGAT TCTGATAGAG    1980

CCCACTGCTG CTTTAGACAC AGATGGCTTA GGTGTTGCTT TAGCATTCTA CTTCCTTACT    2040

TTCACTCCAT TCATTCTTCA AATGCTCTCA GCCAACTTCT CCCCTCCACC CAATTCTCGA    2100

CCCCAGCTAT GATGTTACAG GATATCTTTT CTGACTACCT GCTTACTTTT ATGAGGACAA    2160

GTTAGTGTGA GTGTGTATCA GTATGTGCAA GTATTCTCAT GACTTTCCAA CCCCTCTCTC    2220

ACCTTGGCTT GCGGCACTCA CCTCTGTTGT AACAACTATC ATGCTGCATT TGATTCTTTT    2280

AAGGATCAAT AGCTCTCTCT AGGCTGAGAG CTTTTGAAGA TCAGTATCTT TGTCTTATTC    2340

ATTTTGGTAT CCTCTGGATT AACATTGTTC TAAAAAAATT TTGATAGAAT CTTAGTAAAT    2400

TCTGCATGGT CCCAGAATTC TAACAAAGGC TTATACTTCA CACGGTTAAG GGAAATGGAA    2460

TTCCATGAAA TGAAAGAAGC TAATCTTGTT AAGAATAAAT CACAGGCTCA TTGACTCTCA    2520

GGCTTATAGC ATTTATTCAT AACCACCACC ACCACCACCA CAATTACCAT CACCCTCACA    2580

ACTAAGGTTT GCAGGACAAA TCTCTTTCCC AAGTAATCTC CCCAGGTGTA CCAAGGTACA    2640
```

```
GCACTCCCAC ACTCACCTGA TCTCATACTG CCTCGGCCAG TATGGACTCA AGTTTGAGAC    2700

CATAGTCAAT CAAGAGCTTG ATTAAGTTTA AGAAATCCTC TTGAGGCATC AGAATAAAAA    2760

AGAAAACTTT AAAATGAAAA AAAGGGAAAG AAAACTAGAA TTCAGCAACA GGAGTACTTC    2820

CATGAAGAAG TTTAAAATAC TTCTGTGATG TCAATTGTGA TTGGAGGTTA CTTTACACTG    2880

TGAGACGAAT TTCCTTCTTA CTTAGGGCTC ATTTATTCTG GCAAACTGCA CTCTCTCTAG    2940

AGGGCATGAT TATAAGTAGC AGTGAGTTAG AATGAAAGGT CTTTTTATTT TGGTTTGGAG    3000

TTTTACGCGT CTTTTTCTCT CTCTTTTCTC CCGGTTCCCT CTGTTTCGTG CTTTCTACCT    3060

GCAGTTCATA AAAGTGTGGT GAATGGGTCT TCTCTTGGGC GTTGAATGC CAGTCAATTC     3120

CAACTCCTTG GGGGAACTA TGGGCTTAAA TAATATTAAA TAACATCTAT GTAAACAATA     3180

CCTACTAAAT TATTATCCAA TCAGGATTAA TTGGCTTTCT ACTCTCTACA CCATTTAAAA    3240

AGAAGATTCT TCTGTGTTCA TCTTGAAAAT GTCTCTCCCT TCATCTTTAT TTTTCCCCTT    3300

AGACTACAAG GCTTTTGAAG AAGCAGCTGA ACACTTCCAG CCTTACATCA AATTCTTTGC    3360

CACCTTTGAC AAAGGGGTAA GTACCTATGA AACCCCAATT TGAACAGTTT TGTAGGCATG    3420

AAGAATTAAA GTTTGAACTC TCACCACTCT TTCTTTTCTT TTAGCAACAT TAACCATCCT    3480

CCCTTGCCTC TTTCTCTAGA AGGGTTAAGA ATTATATCAC TAAATCACTA TTGGATTTAA    3540

GATGAGTACA AAGATGACTA AGTCAGAGGA TGTAAGGATA TTTATGAAAA CATCCAAGGA    3600

AAAGTGATGA CCCACCATTA TCTTCTTATA CACTGAGATG GGAAACGTGT GGGCCCAGAG    3660

TGTCCCAGCC CACTGAGCCC ACTGCCTTCC TTTTTCCCTT AGGGGTATC CTCTCCCTTC     3720

CTGGGGTTGC ATACTTCCCC TTCTACTGCG TCAGGATGGG AAGTAGAATG GAACTCCTC     3780

TGTGATTAGT TCAAGCAAGT GTTCTGCGAA AAACAAGAGG AAGTCAGTGA CGTGAAGCAG    3840

GGAAGGGACG TGGTGGGATG AGATTGCATT CAGTTCATGT ATATGATGAA CCACTTCTGT    3900

AGACATGGCC CAGTCTTCAA GCCTATGATC CAGAAGAGTG CTCTATAATC CAAGTAACAT    3960

AATCTAAACT TGAAGAATGT TTATCCTAAT TAGTTGTATT ACAGTTGGGA GGGATCTTGA    4020

GCAAGAATAA TCAAAAAGC TATCATGTAT TAAGTGTCTA TTATGGGCCA GGTGCTGTGC     4080

TCACACCTGT AATCCCAACA CTTTGGGAGG CTGACGGGGG TGGATTGCAT GAGCCTTGGA    4140

GTTGGAGACC AGCCTGGGCA ACATGGTGAG ACCCCATCTC TACAAAAAAT ACAAAAATTA    4200

GCTGGGTGTG GTGGCACACA CTTGTAGTCC GAACTACTTG GGAGGCTTGA GGTGGGAGGA    4260

TCACTTGAGC CCAGGAGGTT GAAGCTGCAG TGAGCTGTGA TGCATACCAT TGTACTCCAA    4320

CCTGGGCAAT GGAGTGAGTC CTCTCTCAAA AATAAAAAT ATAAAAAATA ATAAATTCAA     4380

AAAAATTTTT ATGTGCCAGA GTCTGTGCTA AGAAGTCTCT TTGTGCCAGA GTGTGTGCTA    4440

AGAAGTTAAC ATGGATTTTC TCACTTCATC CTTTCAACAC TCCCATAAGG GAGGAATTAG    4500

TATCCTCATT CTACAGAGGA TGAAACTGAG GTGCTGAAAG ATTAAGTGAT TTTTTCATGA    4560

TCATGTAGTT ACTGAATTGA GAAGCTTGCT ATAATCTCAG ACCAGCCTGA CTTCAAAGTC    4620

AATGCTCTGT CCTACTTTAC TCCAGAGAAA GAAGCAATAT ATGCAAACTG CCTAGCTGGT    4680

TTTTGGCACA CAGGAAGCAT TCAGTAATAG TTAGCCAGCT ATGAGCACCA TTGTTCATAA    4740

GAAAGCAATC ATCTAGGCCC AGGAAGTGGA GGATTGGATA GGATATTAGT AGAGAAAGGG    4800

AGGAACAGAG AAGCCGAAAC TGAATCCATT ACTGACATAT GGTTCTGATG GACCATTTGG    4860

TTCTAATGGA CTAGGTGTGG CTAAAGAGGC TCCTGGGTAA GAATCCAGCT GAAAGGAATA    4920

GAGAGGCAGG CCAATTAATT TGTCCAGCAA CAAAGCCTTA GTTTTTAGAG GGGTGGTTCA    4980
```

-continued

```
ACGTTGAGCT CAGGGTAGTA TTTGTTTGTA GAAGTGCCTC CTAGTGCAAC TGTATAGCTT    5040

CATGCCTGTG GTCCATGAAA AAGGTGAGGT CAGGCTATGA TTAAAAATTC AGAGAGATGC    5100

TTTATTCAAA TTCTGTAGGA CACTGAGTCA TAAGTGCCAG TGTTCATGTA GCCTTGTTGG    5160

ATTTCAGAAT ATTTAAAGAG ACAAAGGTAC ACAGAGGGGA GAGCACTGAG AGGACTCTGA    5220

TGCCATTTGG TGCTTAAGAA CTTGCATCCA TCAGTTGGGG TTGAGGGGGT GTCCAAGGGG    5280

AGATGGTGGA GTCCAGAAGG CATGACTGCA CCTGGTAGAG CCTCAGTGGT TTCCAGCAGG    5340

GAGTGCTAGG ACAGAAGAGG AGAAAAGTAA TAAATGTGAA GTGGCTGAAA GGACCTGTTT    5400

GTACAACACA TCCTAGGGAA TCTCAGAGGG ACCTGGAGGT GCTTTGTTGA GGTCTGAAAC    5460

CAGGAGAGGC AAGGGACAAG AAAGCACTAA TGCGGTCACA AAAATGCAAA AACAACTGG    5520

CACTAGTAAA AGTGGATATA ACAAGAAGAT CTGGCCATTG ATGAGATGAT GAGAGAAGGC    5580

CTCAAAATAA CTTAAGATAG CAAGTCTTGG CGTTAAGACA GCAAAAATTA TGAAGCTACT    5640

GAAAACATTA GGAAATCCAG GAAGAAGAAT CTATTGAGGA ACAAGAGATG GGGTTATGAG    5700

TTCTATTTTC TAAAAGTTGG GGAAACATTC AACTGGAAAT GTCCTTAATT AATTAATTAA    5760

TTAATTCAGT CATTCACTCA ACAAGTATTT ATTGAGTGCC CTTTATTGGC CAGGCACTCT    5820

TCTTAGTGCC AGGGACACAA CATTGAGCAA AGCAGATTCC TGCCCTTTAG AATTTAAAGT    5880

TTATTGTGGG AAAGAGAAGA TGGAAAGACA GAAAGTTCAA AAGTAAACAA ACCAATAAAT    5940

ACATCATATG AGTTGCAAGA CTGTAAAGAG GGTGAGATGT CATGGCTGCT GATGTAAATT    6000

TGTCAGTCAG TAGTTCCCAA CCACTATCCA TATTAGTATC CTCCAACAAG CTTTTAAAAC    6060

CATTGGTCTC TGGGCCCCAG CCTGGAAATT TTAATTTTTT AGGGTTGTGG CAGTGTCTGG    6120

GAATCTGCAT TTTCAAAAGC CACCCAAGGA ATTTTAAAGG GTGTGGAGGT TTAGGACCAG    6180

TACTGATCTA TTAATACTAA TCCTAAATCA AGCCACACGA AGGCCCAACC TCTCTGAAGA    6240

AGCAGTTAGA ACAAGAAAGT GTCAGAGGGC CAAGGATGGT TCCACTCTGC TGCACCTCAC    6300

AGCCTGAAAA ATATCAGTTC TTAAAATCCC ATGTCCCCGC CCACTGACCT GTTCCTCTCT    6360

CTGTCTGAGT GAACAATGAG ACGAAAAATC ACTTTCTTTT TTAAATCACA CTGGAGCCAA    6420

AGGGTGCTGT GACTAAACAA AGTTAGTGGA GAAGATAGAT GTTGGGAAGA CCTAAATTTA    6480

GTAATGGCAA AAACCATTAC TTTTGGCAAA AACTGGCGAT TACTTTTGCA CCAACCTAAT    6540

ACTTGAGTTG GTTTCATTGG CAACAACTAA AATGACTTGC TAACTGGAGG AAAAATGATT    6600

TGTATCAAAA TTCATATACA TGCACATGTC AGAAAATTGG CATTGTACTT TGTAGTTTTC    6660

TTATCTTTGT TGAAATCTAT TCCAACTAGT TAACAGATAA AAGCATGAAA GAATTCATTT    6720

TTATGGACCC ATTTGGTTCT TAATAATATA ATTCATTCTT ATATAATGCT AATACCCATG    6780

AACCAGATCT CCTCCTGGAA TAATGCCTTG GGTTCAGTAG GCCCCACTAA ATACTTACTG    6840

AATAAATGAA TGAATAAAAG CTTCAACCAA TCAAATCCCT TCAGTCCTTA CCATCCAAGA    6900

TAGGAATAAT AAGAATGAAA GAGGGGGTCG GGCGCAGTGG CTCACGCCTG TAATCCCAGC    6960

ACTTTGGGAG GCCGAGGGGG GAGGTGGATC ACCTGAGGTC AGTAGTTCAA GACCAGCCTG    7020

GCCAACATGG CGAAACCCCA TCTCTACTAA AAATACAAAA ATTAGCTGGG TGTGGTGCCT    7080

GTGCCCATAA TCCCAGCTAC TCGGGAGGCT GAGGCAGGAG AATCGCTCGA ACCTGGGAAG    7140

CGGAGATTGC AGTGAGCCGA GACTGTGCCA TTGAACCCCA GCCTGGGCAA CAAGAGCAAA    7200

ACTCTGTCTC ACCAAAAAAA AAAAAAAAA AAAAAAAAA AGAATGAAAG AGAGGGATTC    7260

TCTGAGATAC AAGATGAGAG CACTCCATGA TGGTGGTAGG TAGACAGTGA AGAGATCCCT    7320

GGGAAATTTT TACTTAGCAT TTCCAAGACT TAAATTAAGG ACACGACAAT CCAATTTTTA    7380
```

-continued

```
CATTCTTAGA CAGCACTGTG GACCCAGACA TTGGCATTCA GAGACGAGAC TATCACCACC       7440

ACCAGGCGGG TTTGACTTCT GGCTCTGCTC CCTCCAGATA TATGATCCTG ACAAATTTCT       7500

TACCCAAATT GTGCCTCAGG TTCATCATTT GTAAAATAAC TATGATAATC ATTCTTACCA       7560

CATACAATCA AAGTGAGAAT TAAACAAAGA ATCAACCTAA AACACCTGGC AGCAGGCCTG       7620

GCACGTGATA AGCACTCCAT ATGTTTGTTA TTATTACTGT TTTCATTCTG ATCACTTCTC       7680

CTTTCATGGA AACAGTCTTC TGGTTCCTAG AATACATAGT AAGTGAACTC AGAAAACCAG       7740

AATTCAATGT CATTTTCTTG CCCACTCTGG CTCCCTGCCT CATCACCTCA TCATCTACAT       7800

CACCCCCCTA CCCCTGAGAA GAGGGAAAAA CAGTTAGAAA AAACTCCACA TCTCCCTCTC       7860

TTAAAATTAA CCTGACAATA AAATCTCCCT TGACTGACTA TAGCTGTCAA CATGGCCTGT       7920

TTTCTTGATC CACCCACCTC TGCCTCCCAA AGTGCTGGGA TTACAGGGTG AGACATGTGC       7980

CCGGCCTCAT ATTACTTCTT TACATTTTAA ACTAATGATT AATATATTT AAAGAAAAGC       8040

AAGTCTTTGT CTCAAAGCAA GGAAACTTTA TTACCTTCTC AATTTTCTGA TTTTCTATAC       8100

TCACACCTTC CAAAAGGTTT CTAGAGTCAT TTTATACCCA AGGAATACAT GTGTAATGTC       8160

CTAAAACAGA ACTGTCAATT TAAAAATATT TAATATTATA CCTCCTTTCA AAGTTTCTA       8220

AAAGCTTTGG AGTTTTTAGT TTTATAAATA TGTGTCCATA AAAATTGTTT TCTCACTCCT       8280

GATTCTCTAA ATATGTCACA ATCCAAAACT AAGAAAAGCA CTATAAAAAC AAATGAAAGA       8340

TGGTATTAAA AACACTATTA TTTATATGTT AAGTTTATGC AAGAGGCAAT ATTTTAAATC       8400

TTCTAAGTAA ACCTTATGAA TCATCTTAGT ATGAGAGCAG AGAAAGGAAA AAAGGCTCAA       8460

TGCTCCTCTA ATTTTTAACA ATCTAACAAT GTATATTTAA TAAAAACTAA ATAGAAATTA       8520

TTCATATTTT TCATTTAAGC ATATTTGTTG GCATGGGAGT CAGATGACTA GATTTTTCCC       8580

ACAGTGACTT TTTCATTCTA GGTGGTGATG TTTAAAGACA ATATAAACAT GCAGTTTATT       8640

ATTACTAATC AGTTAGACTA CTGTTGCTTC TTAAGTAGTC CATAGGCCTC ATAGATCACT       8700

CATGAAAAAT GTTTTAAAAA ATAAAAAGAA AACATATTTT GTCTTTAACA CAAAAGATTT       8760

TTTTAACTGA TTTAAGTACT TTTTTTTTCT TTTTTAACTT ATTTCTCATT ATTTCTTCTT       8820

CTGGAACTCC CCAGGCTGTG GAGGTTCAAA ACCAGAAACA ACCAGCAGTA AGTCTATTTT       8880

AATTACTTCT GTTACAGGCA TGAACTACAA AATATATTCT GCAAAGGTCA ATTGTATTAT       8940

AGATGCCTTC TGTCTAAAAC CTAAATATTT CATTTCCATA AAACAATCTA ATAATATTTG       9000

CAAGAAAATA ATTTCAGCCA ACAGGTGATA TGAATCAACA TTGATGTTCA TCTGAAAGTT       9060

TTATTTCTT ATATAACCCA AATCATGTAT CTTTGGTTTT CATGTATATT TAGCAATATG       9120

AGAAAACTCT TTCAACATTT CATATTGGAA AAAAATGAAA ACATAAGTAA AGCTTAATAT       9180

TTCCCCTTTC CACTTTTTAA GACAAGGGAA GATCCTTTTC TGACCCATCT TTGAATACTT       9240

CTCATACATC TATATTTACT TCCCCTTTCG TTTCCCAAAT ATGTTTGAAT ACATTAAAT       9300

GTGTCTCGTT TTAGGAGAAA TGTTTGCTTT GTAGTATAAT TTTGTCAATT TATTTCTATT       9360

CATATGGAAA GGTCTACTGA CAAATTTTTA AACAGAGGCA CATAGATATA GACAATTCTT       9420

TATCTAATCT TTTGTGAAGA AAATTAAACC AAAAAAAATC CAAAATCTAA ATCCAGGAAT       9480

CTCTCCACAT CACATTATGT TACTATTCTG CTATAGTTTG GAAAAAATAA ATGTGCTCTT       9540

GGGCTAATTT TTAAATGAAT AAAATTTGAG ACCAATTACA AATATGTGGT GAGAATACAT       9600

ACGTGTGTGT GCGCCATTCT GTGTGTGTCT GCATGTTGTG CTTGTGTATA ACATGTCAAA       9660

GTTCTCAATG AGATTTTTCT CTGTGTTGTA CCTACAATAG CTAACATATA AGATCACTTT       9720
```

```
CCATATATGC CAATCTCTGG GCAATATGGT TTACATTATG AATAAACTCA TCTAATTTCT    9780
TGAAACAAAT ATTATATTAA TATTATCAAA ATAATATTTA TAATATTGAA ATCATAAAG    9840
TGGAAAGGCA ATGTACAAAT CAACATCTTA TAAAATAATA TTGCTGCTGG GTTCCATACT    9900
TCTAATATCT TACTCAATGG TAAATACTAT ATTATTTCAA AAAATGCAGA TTTAAGGTAT    9960
TTCCACATTT GGGTCTATAA TAATAATATT CTGTATAATT TATTTTTTTT GCAGTGCCAT   10020
GAGAATGATG AAAGACCATT CTATCAGAAA ACAGCTCCAT ATGTCCCAAT GTATTATGTG   10080
CCAAATAGCT ATCCTTATTA TGGAACCAAT TTGTACCAAC GTAGACCAGC TATAGCAATT   10140
AATAATCCAT ATGTGCCTCG CACATATTAT GCAAACCCAG CTGTAGTTAG GCCACATGCC   10200
CAAATTCCTC AGCGGCAATA CCTGCCAAAT AGCCACCCAC CCACTGTGGT ACGTCTCCCA   10260
AACCTGCATC CATCATTTAT TGCCATCCCC CCAAAGAAAA TTCAGGATAA AATAATCATC   10320
CCTACCATCA ATACCATTGC TACTGTTGAA CCTACACCAG CTCCTGCCAC TGAACCAACG   10380
GTGGACAGTG TAGTCACTCC AGAAGCTTTT TCAGAGTCCA TCATCACGAG CACCCCTGAG   10440
ACAACCACAG TTGCAGTTAC TCCACCTACG GCATAAAAAC ACCAAGGAAA TATCAAAGAA   10500
CACAACGCAG GTAAATTAAC AGTATATAAA ATGAGTAATT CCGACAAGAA GCATGGATTT   10560
ATGAATACAA CCATAAATTC TAAAATAGTA CAAATAGATA AACTAAGTGT GTTACAGAAG   10620
CAGACAAAAC AGGGTACTTA CAGTTTTACC TTGGTAAACC CATAGCATTG ATACACCAGA   10680
TTCTGTTCCA ACTAGAAATT TAAAATAATT TTATTTGACA AAGTGAAAAT AATTGGCAAC   10740
TTCATTATCA AACTTTTTTC TGACAATTGG GACACTCTTA GAATGTAATA GTTTTATTTC   10800
ATCCTTATTC ACACACAAAC TATGACAGTA GAGTAAAACA GCAAGTAACA TTTTCATGAT   10860
ATTTCAAAAA TAATTTTTAG AAGAAGTTAT ATAGAATATG AGTTTGAGTA AATTTTAATT   10920
CTGTAACAAT TCTCTTGCAC TCTCATTGTA GTATGAACAG AGTAAAAGGA AATGATATGC   10980
TTCCATGCAT TTCTTTATTT CAGACATCAT TTCCAAAATG ATTCATGAAG TTAAGCCTCT   11040
CAAATTTCTC CTATTCTAAG ATAAACCCAT GGAAGAATTA TAATGCTTAA CTTGAAAAAC   11100
ACATAAATAT TAAAAGGATA CTTTCAGAAC ACAATGTGAT GCAAAGTGTT ACTATTTATT   11160
ACTTGGACCA ATGGATAATG GCAGAATATA AAATAATTTG AAACTTATGA GAAGAATTTA   11220
AACAAAGAGA ATGATTAATA AAGTGGAAAA TATCCAAAGA GTGTAAAATA ATTTGGGGAG   11280
AAAGTTGCAA AATGTGGAGT TTCTTTACAA CAAATATTTT CAGTCCATCA GATGTCTACA   11340
TGTTTTATGA TCTAAAATAC CAGACAATGG TCTGTGATAT CATGGGACTA CCATTAGCCC   11400
AGAAAAGGTT GCTTCTTTCA TCTGCTTGCC TAATGACCAT AGGCTAGTCA TTACTTTCTC   11460
TGAACTTTTA TTTTCTCATA ATTCTGGTTG CTATAAGACT CAAGAGAGAA TGCACATGGG   11520
AAAGGATTTT AAAAACTGAT CAATCTGTAA AATGTCATGT ATTGGAAAAG ATAAAGTAAA   11580
ATTCATACCA GTATCCTAAG TCTCCACTAA ATGATAAAAA CCGTACATAA TTATGTCTGT   11640
TGATTCCCAT AGTAACCATA TGAAACAGAT ATTATTCCTA TCTCAAATTT AGGGATAAAA   11700
ACCAGTAGGA CTGAGGACAT TAAGTAAATT ATCACAGCTA GAAATTGCAA ATGGGAGGCA   11760
AACCAAACCT GTTTATTTCA GATAGTGGGG TTTAATTACT ATGTCATTTA TTTTTATATG   11820
GGCTGTCTAA CTTGCTGAAA AACAGGGAAA ATACACTGTG ATTTCCTTAG ACTAGCATAT   11880
GGGTAAATTG TGTTGTTTAG TTGCTGTTCA ACAGGATATC CATTAAGAAA AAGAGAACAA   11940
GAGCTGGTTA AACAGCTGGC TTATTATATT TTGGAGAACA AAATAAGAAA ATTAATAAAG   12000
ACAACATGAA AGCAAGTTAT TTAATAAGTA GTTACATATT TTACTGATGC AAAACATAAA   12060
GAAGCATGTA AAAGAGTTTT TTCTGTAAAT ATTACATAAT GTCTATTATT TTCAGTTTAC   12120
```

```
TATATGCCTA TTTTAAATAT TTAAGTTTAA ATATGTAATC TGATTGACTT ATTGGATACA    12180

GACATGAAAG AAAAATTGTG GAAGCTAAAT AAATATATAT CATGAGAACT GTTAACATAC    12240

TATGAATAAA TTTCTAAACT ATCATTATTT TTTATAGGAC TTGCTGAAAC CAAATTACTA    12300

CTTCACACTC TCCTTCAGCC ATTTGTCTGC CTTCAGTCAA CAGAAAATGT GATTTTCACA    12360

GATTCAGCTC TTCTCTCCTT ACATTTTACA TTCATGCCAC ATTCAATATT TTGATTCTTG    12420

CACAATAAAG CCAACTGATT GCAACTGATT CTTTGAGAGG AGTTTGCAAA GGTACCTCAG    12480

GGATCTCTGA AACTTTGAAA CGCTATGACA AATTTAGTGT GAGTTAGAGT ACACAAATTT    12540

ACCTAAAGGC AGTGCTCATA GTTTCATCAG GTTCTCAAAG TGGTTCATGG TCTGACACTA    12600

AGAATTTCTC CTCTAGGATG ACACTGGGAC CAGAGAAAAG CCAAGCCATA GTGTTCCAAT    12660

CCAGGGGACC ACAGAGTGAC TCTTGAGAGC CATGGGAACT CTAGATTATT CCTGAGAGCA    12720

AATTCTGGGC ACAGGCAAAC TACAAATGTC CAGAACTACA AACACAGATA CGTTGCAAAA    12780

TTATAGATGT TGACAGAGAC TCTAAACATG CATGACCAGA TTTCCCCACA CTGGACTCCA    12840

CAGTCTCACA TCTGTTCAAA CACACACACA CCCCCACACC ACCCACCCAC CCACACACAC    12900

ACACACACAT CACACACCAG AAAGCTTCTG GAATTCAGGT ATTCCAGTTT GGAAAAACTC    12960

GTGAATATTC AAGGTCCAAG GATAGGACAT AGTTGTTTTC TTAAACAAAT ATTGCAAGGA    13020

AAATCAGGTC ACCTTTGTGC TTGGTCCATA TTTAACACAT CATGCCAGAA AAAATAAAAT    13080

TCACTCAGCC CTTACAAAAT GTTT                                          13104

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

GTTGGGTAAC GCCAGGGTTT TC                                              22

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

CAGGAAACAG CTATGAC                                                    17

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

TTCCGGCTCG TATGTTGTGT GG                                              22
```

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 8:

ATCCCGGGCA GGGTTAATGC CAGGGC                                          26

(2) INFORMATION FOR SEQ ID NO: 9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 9:

CGAAGCTTCA GCTCAACCTA CTGCCAAC                                        28

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

CTGGTTGTTT CTGGTTTTGA ACCTCCA                                         27

(2) INFORMATION FOR SEQ ID NO: 11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

TATGGAGGTT CAAAACCAGA AACAACCAGC ATG                                  33

(2) INFORMATION FOR SEQ ID NO: 12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

TATGCAGAGG TTCAAAACCA GAAACAACCA GCATG                                35

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single -continued (D) TOPOLOGY: linear (ii) MOLECULE TYPE: DNA (xi) SEQUENCE DESCRIPTION: SEQ ID NO: 13:

CTGGTTGTTT CTGGTTTTGA ACCTCTGCA                                      29

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

GGGGTCGACT GGTGTTTTTA TGCCGTAGGT                                     30

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GAGAGAAGAT CTGACTGGCA CGAGGAAAGG                                     30

(2) INFORMATION FOR SEQ ID NO: 16:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

CGTCGACGTA C                                                         11

(2) INFORMATION FOR SEQ ID NO: 17:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

GTCGACGGTA C                                                         11

(2) INFORMATION FOR SEQ ID NO: 18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

GGTGGTACCA TGAAGAGTTT TCTTCTAGTT G                                   31

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

CTGTGTGGCA AGAAGGAAGT GTTGT                                          25

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GGTTTGGGCG ACGTACCACA                                                20

(2) INFORMATION FOR SEQ ID NO: 21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

AATTCCCCTG GCATTAACCC TGCCTTTTTT G                                   31

(2) INFORMATION FOR SEQ ID NO: 22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

AAAAAAGGCA GGGTTAATGC CAGGGG                                         26

(2) INFORMATION FOR SEQ ID NO: 23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

CCGGTACCAA GACCTGACTG GCACGAGGA                                      29

```
(2) INFORMATION FOR SEQ ID NO: 24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

ATTCTAGACC AGGCCTTATC T                                                 21

(2) INFORMATION FOR SEQ ID NO: 25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

CCGGTACCAT GAAGAGTTTT CTTCTAGTT                                         29

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

TTAAGCTTTA CTTATGTTTT CATT                                              24
```

TRANSGENIC NON-HUMAN MAMMAL EXPRESSING THE DNA SEQUENCE ENCODING KAPPA CASEIN MAMMARY GLAND AND MILK

The present invention relates to a DNA sequence (SEQ ID NO:1) encoding the human milk protein ϵ-casein or encoding an analogue or variant of said protein. In a particular embodiment, the DNA sequence encodes a polypeptide having the amino acid sequence shown in SEQ ID NO:2 below. The DNA sequence is advantageously used in the production of recombinant human ϵ-casein or an analogue or variant thereof, either by means of a prokaryotic or an eukaryotic production system, or more advantageously by means of production in transgenic non-human mammals such as bovine species, e.g. cow. One main use of the recombinant human ϵ-casein is as a constituent of infant formulae used for feeding infants as a substitute for human milk. When used as a constituent of infant formulae, it is contemplated that the recombinant human ϵ-casein provides a substantial improvement of the nutritional and biological value of the formulae in that a closer similarity to human milk is obtained. It is contemplated that the recombinant proteins can also be used in a number of other embodiments due to the advantageous properties of human ϵ-casein and can be used e.g. as pharmaceuticals.

BACKGROUND OF THE INVENTION

It is well known that human milk-feeding is considered superior to formula-feeding for infants. Not only does human milk provide a well-balanced supply of nutrients, but it is also easily digested by the infant. Thus, several biologically active components which are known to have physiological functions in the infant are either a constituent of human milk or produced during the digestion thereof, including components involved in the defense against infection and components facilitating the uptake of nutrients from human milk.

In spite of the great efforts which have been invested in preparing infant formulae, it has not been possible to produce a formula which to substantial extent has all the advantageous properties of human milk. Thus, infant formula, often prepared on the basis of cow milk, is generally incompletely digested by the infant and is lacking substance known to have effect on the physiological functions of the infant. In order to obtain an infant formula with a nutritional value similar to human milk, a number of additives including proteins, protein fragments, vitamins, minerals etc., which are normally formed or taken up during the infant's digestion of human milk, are included in the formula with the consequent risk of posing an increased strain on and possible long-term damage of important organs such as liver and kidney. Another disadvantage associated with the use of cow milk-based formulae is the increased risk for inducing allergy in the infant against bovine proteins.

As an alternative to cow milk-based infant formulae, human milk obtainable from so-called milk banks has been used. However, feeding newborn infants with human milk from milk banks has in the recent years to an increasing extent been avoided, because of the fear for the presence of infective agents such as HIV and CMV in human milk. In order to destroy the infective agents in human milk it has become necessary to pasteurize the milk before use. However, by pasteurization the nutritional value and the biological effects of the milk components are decreased or abolished. Hence, human milk is used to a still lesser extent.

Presently, commercially available human infant formula used to replace mother's milk is based primarily upon the protein constituents of cow's milk. These infant formula compositions have led to difficulties in terms of nutrient balance, bioavailability of nutrients and sensitivity of human infants to non-human/animal protein. Specifically, allergic reactions to the non-human animal protein used with these infant formulas caused a change in the protein component of the commercially available formula to soy-protein based formulas, although many infants that are allergic to cow's milk are also allergic to soy-based milks (Am. Acad. of Pediatrics Comm. on Nutrition, *Pediatrics* 72, 359–363 (1983)).

Additionally, many of the problems with the use of cow's milk protein are associated with difficulties in digestibility because of bovine casein content and structure (L. Hambraeus, E. Forsum and B. Lonnerdal, In: "Food and Immunology", pp. 116–124 (Eds. L. Hambraeus, L. A. Hanson and H. McFarlane) Almquist and Wiksell (1977)).

This has led to the production of infant formulas which contain a greater proportion of whey protein, since it is more readily digested by human infants (M. J. Newport and M. J. Henschel, *Pediatric Res.* 18, 658–662 (1984)), and little or no bovine casein. However, the major protein in whey of cow's milk is β-lactoglobulin. This protein is essentially absent from human milk and has been determined to be on of the main causes of cow's milk allergy in infants (I. Axelsson, I. Jakobsson, T. Lindberg and B. Benediktsson, *Acta Pediatrica Scand.* 75, 702–707 (1986)). The extent of the problems with allergies to formulas based on cow's milk may be appreciated from the fact that soy-based formulas now comprise a large portion of the human infant formula market in the United States.

Soy-protein formulas, although different in carbohydrate and protein source, are similar in composition to cow's milk protein formulas following the American Academy of Pediatrics, Committee on Nutrition recommendations for nutrient levels in infant formulas. Differences include a slightly higher protein level and slightly lower carbohydrate content. The protein source is generally soy-protein; the fat is a blend of vegetable oils; and the source of carbohydrate is usually sucrose, corn syrup solids, or a mixture of both. However, the use of soy formulas tends to raise serum alkaline phosphatase and blood urea levels in infants in addition to causing the allergic and digestibility problems encountered with the use of bovine-based protein infant formulas.

Human milk differs markedly from that of other mammalian species, including cows, in that it contains a lower over-all protein content and lower ratio of casein/whey as well as a different protein composition. For instance, the casein subclasses of human milk comprises only β-casein and ϵ-casein, whereas the bovine casein subclasses are α-casein, β-casein, and ϵ-casein (Miller et al., 1990). Also the amino acid compositions of human milk protein differ from that of other mammalian milk proteins. ϵ-casein is a glycosylated protein which is present in milk of several species including man. Human ϵ-casein has been shown to contain several (up to 10) prosthetic sugar groups distributed throughout the peptide chain instead of 0–5 as in the case of cow and sheep ϵ-casein.

A number of different biological activities have been suggested for ϵ-casein and ϵ-casein peptides. For a review see e.g. Miller et al. 1990 and Fiat and Jollés 1989. ϵ-casein has been shown to have a calcium binding site (Fitzgerald and Swaisgood, 1989). Examples of other functions of ε-casein or fragments thereof released during digestion are inhibition of gastrin secretion and thus acid secretion in the stomach (Stan et al. 1982), a regulatory effect on gastrointestinal hormones and thus on release of enzymes from exocrine pancreas (Yvon et al, 1987), growth promoting effects on *Lactobacillus bifidus pennsylvanicus* (Bezkorovainy et al, 1979) and *Bifidus infantis* (Azuma et al, 1984), opioid-antagonist activity (Chiba et al., 1989), inhibition of angiotensin 1-converting enzyme (ACE) (Marayama et al, 1987), inhibition of platelet aggregation (Jolles et al., 1986), immunostimulatory properties (Jollés et al, 1982) and various antimicrobial effects (Miller et al, 1990). A digestion product (ε-caseinoglycopeptide) of human ε-casein has been found to inhibit the adhesion of certain bacteria. *Streptococcus pneumoniae* and *Haemophilus influenzae,* to human respiratory tract epithelial cells (Aniansson et al. 1990).

It would be desirable to be able to prepare an infant formula with a composition closer to that of human milk and thus avoid the above disadvantages associated with bovine milk-based infant formula, e.g. a formula comprising human milk proteins. However, this would require that human milk proteins are obtainable in large quantities. Although human milk proteins may be purified directly from human milk, this is not a realistic and sufficiently economical way to obtain the large quantities needed for large scale formula production, and other methods must be developed before an infant formula comprising human milk proteins may be prepared.

Chobert et al. in 1976 isolated the so called caseinomacropeptide, the glycosylated C-terminal part of human ε-casein, and determined part of its amino acid sequence. The complete sequence of the C-terminal part of human ε-casein was determined by Fiat et al. 1980. The sequence of the para-ε-casein, the N-terminal part of ε-casein, was later determined by Brignon et al. 1985. The complete sequence of the native human ε-casein was reported to contain 158 amino acids.

Several milk protein genes, primarily from rodents or dairy animals, have been cloned and sequenced, but knowledge of the genes encoding human milk proteins is still sparse. Hall et al. 1987 published the sequence of the human α-lactalbumin gene. Menon and Ham 1989 disclosed the isolation and sequencing of a partial cDNA clone encoding human β-casein, the complete cDNA sequence was later determined by Lönnerdal et al. 1990. In WO 91/08675 is described human infant formulas containing recombinant human α-lactalbumin and β-casein. The sequence of the human lactoferrin cDNA was published by Powell and Ogden 1990. The cDNA cloning of human milk bile salt-stimulated lipase was published by Nilsson et al. 1990. Menon et al., 1991 disclosed a mRNA from which a part of amino acid sequence (3'-end) of the human ε-casein can be deduced.

BRIEF DESCRIPTION OF THE INVENTION

It is an object of the present invention to provide a means for producing recombinant human ε-casein in a high yield.

Accordingly, in one aspect the present invention relates to an expression system comprising a DNA sequence encoding a polypeptide having the amino acid sequence SEQ ID NO:2 or an analogue or variant thereof which has a biological activity of human ε-casein, the system comprising a 5'-flanking sequence capable of mediating expression of said DNA sequence.

A transgenic cell or animal contains one or more transgenes within its genome. A transgene is a DNA sequence integrated at a locus of a genome, wherein the transgenic DNA sequence is not otherwise normally found at that locus in that genome. Transgenes may be made up of heterologous DNA sequences (sequences normally found in the genome of other species) or homologous DNA sequences (sequences derived from the genome of the same species). Transgenic animals have been reported. For example, U.S. Pat. No. 4,736,866 discloses a transgenic mouse containing a c-myc oncogene. Other reports of transgenic animals include PCT Publication No. WO 82/04443 (rabbit β-globin gene DNA fragment injected into the pronucleus of a mouse zygote); EPO Publication No. 0 264 166 (Hepatitus B surface antigen and Tissue Plasminogen Activator genes under control of the whey acid protein promoter for mammary tissue specific expression); EPO Publication No. 0 247 494 (transgenic mice containing heterologous DNA encoding various forms of insulin); PCT Publication No. WO 88/00239 (tissue specific expression of DNA encoding factor IX under control of a whey protein promoter); PCT Publication No. WO 88/01648 (transgenic mammal having mammary secretory cells incorporating a recombinant expression system comprising a mammary lactogen-inducible regulatory region and a structural region encoding a heterologous protein); EPO Publication No. 0 279 582 (tissue specific expression of chloramphenicol acetyl-transferase under control of rat β-casein promoter in transgenic mice); WO 91/08216 (production of recombinant polypeptides by bovine species and transgenic methods).

As used herein, a "recombinant polypeptide" (or the recombinant DNA sequence encoding the same) is a "heterologous polypeptide". Heterologous polypeptides are polypeptides which are not normally produced by the transgenic animal. Examples of heterologous polypeptides include human milk proteins such as human ε-casein.

Each of the heterologous or homologous polypeptides are characterized by specific amino acid and nucleic acid sequences. It is to be understood, however, the such sequences include naturally occurring allelic variations thereof and variants produced by recombinant methods wherein such nucleic acid and polypeptide sequences have been modified by the substitution, insertion and/or deletion of one or more nucleotides in such nucleic acids to cause the substitution, insertion or deletion of one or more amino acid residues in the recombinant polypeptide. When the term DNA is used in the following, it should be understood that for the number of purposes where DNA can be substituted with RNA, the term DNA should be read to include RNA embodiments which will be apparent for the man skilled in the art.

In one aspect the present invention relates to a DNA sequence encoding a polypeptide comprising the amino acid sequence shown in SEQ ID NO:2 or an analogue of said DNA sequence which 1) hybridizes with the DNA sequence shown in SEQ ID NO: 1 or a specific part thereof under the stringent hybridization conditions or 2) encodes a polypeptide, the amino acid sequence of which is at least 85% homologous with the amino acid sequence shown in SEQ ID NO:2, or 3) constitutes an effective subsequence of said DNA sequence, which encodes a polypeptide having a biological activity of human ε-casein.

One DNA sequence of the invention was determined on the basis of a cDNA clone isolated from a human mammary gland cDNA library. The procedure used for isolating the human ε-casein cDNA sequence is outlined in Example 3.

The stringent hybridization conditions referred to above are to be understood in their conventional meaning, i.e., that hybridization is carried out at 67° C. in 2×SSC and final washing at 67° C. in 1×SSC using the method specified in the "Definition" part of the Examples below.

The term "homologous" is used here to illustrate the degree of identity between the amino acid sequence of a given polypeptide and the amino acid sequence shown in SEQ ID NO:2. The amino acid sequence to be compared with the amino acid sequence shown in SEQ ID NO:2 may be deduced from a DNA sequence, e.g. obtained by hybridization as defined above, or may be obtained by conventional amino acid sequencing methods. The degree of homology is preferably determined on the amino acid sequence of a mature polypeptide, i.e. without taking any leader sequence into consideration. It is preferred that the degree of homology is at least 85%, such as at least 90%, preferably at least 95% or even 98% with the amino acid sequence shown in SEQ ID NO:2.

The term "effective subsequence" as used above refers to a subsequence which encodes a peptide being at least partially functional with respect to the activities of human ∈-casein as defined in the following. The subsequence may be the result of a truncation at either end of the DNA sequence or of the removal of one or more nucleotides or nucleotide sequences within DNA sequence. Preferably, when encoding a peptide having a biological activity of human ∈-casein, the effective subsequence comprises at least 15 nucleotides such as at least 20 nucleotides.

Subsequences having a biological activity of human ∈-casein may also be larger and comprise e.g. at least 50 nucleotides such as at least 75, 100 or 125 nucleotides, e.g. 150 nucleotides.

The term "a biological activity" of human ∈-casein should be understood to include, but not be limited to, one or a combination of two or more of the reported activities of human ∈-casein such as "antimicrobial activity", "opioid activity", "immunostimulatory activity", "calcium binding activity" and "micellar formation activity" of human ∈-casein and/or peptides derived from human ∈-casein.

The term "antimicrobial activity" denotes the capability of ∈-casein to inhibit adhesion, colonization or growth of pathogens such as bacteria, virus, or parasites. The "antimicrobial activity" can be determined as disclosed by Anianson et al., 1990.

The term "opioid activity" denotes the ∈-casein derived peptide's capability to bind to opiate receptors (opiate receptor affinity). The "opioid activity" can be determined as disclosed by Chiba et al., 1989.

The term "immunostimulatory activity" denotes the capability of human ∈-casein to stimulate immunological reactions as phagocytosis by macrophages and differentiation of B- and T-cells.

The term "calcium binding activity" denotes the capability of human ∈-casein to bind, transport and deliver calcium ions whereas the term "micellar formation activity" denotes the capability of human ∈-casein to form micelles by itself or together with other milk proteins. These micelles may have an important function in the transport and delivery of ions, vitamins, lipids, peptides, polypeptides, minerals, trace elements and growth factors.

In this connection, it should be noted that the terms "opioid activity", "antimicrobial activity", "immunostimulatory activity", "calcium binding activity", "micellar formation activity" and related terms should be understood to be qualitative and/or quantitative that is, relating first of all to the nature of the activity, such as the nature of the biological activity, and/or to the level of activity of the polypeptide as determined with reference to human ∈-casein. Concerning the digestive fragments of human ∈-casein, the biological activity of these are also of the same quantitative/ qualitative nature as ascribed in the literature to digestive fragments of human ∈-casein having e.g. antimicrobial or opioid activity, respectively.

In this connection the term "digestive fragment" refers to the peptide fragment(s) which, in nature, are generated during the digestion of human ∈-casein by the infant fed on human milk. Such fragments may be prepared, e.g. by cleavage of recombinant human ∈-casein, by expression from DNA sequences encoding such fragments, or by use of conventional peptide synthesis.

In another aspect the present invention relates to a polypeptide produced by a DNA sequence of the invention, preferably a recombinant polypeptide comprising a subsequence of the amino acid sequence shown in SEQ ID NO:2 or a variant or analogue of said amino acid sequence, the resulting polypeptide having a biological activity of human ∈-casein as defined above. In a particular embodiment, the invention also relates to a recombinant polypeptide having the amino acid sequence SEQ ID NO:2 or an analogue or variant thereof. The variant and the subsequence is further defined above and in the following.

In yet a further aspect, the present invention relates to a method of producing a transgenic non-human mammal capable of expressing a recombinant polypeptide of the invention, comprising injecting a mammalian expression system as defined above into a fertilized egg or a cell of an embryo of a mammal so as to incorporate the expression system into the germline of the mammal and developing the resulting injected fertilized egg or embryo into an adult female mammal.

In further aspects, the present invention relates to a DNA sequence encoding a polypeptide as defined herein, a replicable expression vector which carries and is capable of expressing such DNA sequence, a cell harbouring such a vector, a method for producing the polypeptide, a method for producing a transgenic non-human animal capable of expressing the polypeptide, such a transgenic animal per se, milk from such a transgenic animal, an infant formula comprising a polypeptide as defined herein, a method of isolating a polypeptide as defined herein, and the polypeptide proper.

DETAILED DESCRIPTION OF THE PRESENT INVENTION

The expression system according to the invention may be an expression system comprising a 5'-flanking sequence from a milk protein gene of a mammal and a DNA sequence encoding a polypeptide having the amino acid sequence SEQ ID NO:2 or an analogue or variant thereof which has a biological activity of human ∈-casein, the flanking sequence being capable of mediating expression of the polypeptide.

As discussed in detail in the following, the expression system according to the invention is, for many purposes, preferably an expression system in which the DNA sequence contains at least one intron sequence, and, preferably, contains at least one permissive RNA splice signal. In particular, the present invention relates to an expression system, wherein the intron sequence or sequences is/are selected from the intron sequences presented in SEQ ID NO:3 and/or SEQ ID NO:4 such as an expression system which encodes a polypeptide comprising or being the amino acid sequence of SEQ ID NO:2.

In a preferred embodiment, the mammalian expression system according to the invention is one in which the DNA sequence is combined with regulatory element of a gene encoding a milk protein of a mammal so as to form a hybrid gene which is expressible in the mammary gland of an adult female of a non-human mammal harboring said hybrid gene so that the polypeptide encoded by the DNA sequence is produced when the hybrid gene is expressed. As an example, the gene encoding the milk protein may be one selected from casein genes or whey acidic protein (WAP) genes. The present invention also comprises the hybrid gene as such.

As mentioned above, the expression system is preferably one wherein the analogue or variant of the polypeptide encoded is at least 85% homologous with the amino acid sequence SEQ ID NO:2. Another way of expressing the close structural relationship with the DNA sequence SEQ ID NO:2 is to refer to hybridization: The expression system is preferably such that the DNA sequence encoding the polypeptide is one which hybridizes with the DNA sequence SEQ ID NO: 1 or a part thereof under stringent hybridization conditions.

The amino acid sequence deduced from the nucleotide sequence shown in SEQ ID NO:1 is different at eight positions compared to the published sequence determined by amino acid sequencing (Brignon et al. 1985). Based on the proposed signal peptidase cleavage site, it is suggested that the peptide chain contain four additional amino acid residues than previously published (Brignon et al., 1985). If so, the amino acid sequence of the N-terminal is identical to that of rat and very similar to those reported for other species, with the following amino acid sequence Glu-Val-Gln-Asn (residues 21–24 of SEQ ID NO:2). Menon et al., 1991, has disclosed a mRNA sequence from which a part of the human ε-casein amino acid sequence (3'-end) can be deduced.

An interesting DNA sequence translatable into a human ε-casein polypeptide is a sequence comprising a human ε-casein gene or a part thereof capable of expressing human ε-casein. Accordingly, in a further aspect, the present invention relates to a DNA sequence comprising substantially the DNA sequence shown in SEQ ID NO:3 and the DNA sequence shown in SEQ ID NO:4 and which optionally further comprises a DNA sequence linking SEQ ID NO:3 and SEQ ID NO:4. This can be done e.g. as described in Example 7.

An interesting embodiment comprises a modified DNA sequence which differs from the DNA sequence defined above in that at least one nucleotide has been deleted, substituted or modified or at least one additional nucleotide has been inserted so as to result in a DNA sequence which encodes a polypeptide having a biological activity of human ε-casein.

In another aspect, the present invention relates to a DNA sequence comprising a human ε-casein gene or an effective subsequence thereof containing elements capable of expressing a polypeptide having the activity of human ε-casein or a digestive fragment thereof, or an analogue of said DNA sequence which 1) hybridizes with the DNA sequence shown in SEQ ID NO:1 or a specific part thereof under stringent hybridization conditions or
2) encodes a polypeptide, the amino acid sequence of which is at least 85% homologous with the amino acid sequence shown in SEQ ID NO:2, or
3) constitutes an effective subsequence of said DNA sequence, which encodes a polypeptide having a biological activity of human ε-casein.

This aspect of the invention relates, inter alia, to a DNA sequence encoding a polypeptide having the amino acid sequence SEQ ID NO:2 or an analogue or variant thereof which has a biological activity of human ε-casein. In one embodiment the DNA sequence comprises at least one intron sequence; in another embodiment the DNA sequence contains at lest one permissive RNA splice signal.

In a preferred embodiment, the DNA sequence comprises substantially the DNA sequence shown in SEQ ID NO:1. Alternatively, the DNA sequence may be a modified DNA sequence which differs from a DNA sequence as defined above in that at least one nucleotide has been deleted, substituted or modified or at least one additional nucleotide has been inserted so as to result in a DNA sequence which encodes a polypeptide having a biological activity which is similar to, increased or decreased as compared to a biological activity of human ε-casein.

In the present context, the term "gene" is used to indicate a DNA sequence which is involved in producing a polypeptide chain and which includes regions preceding and following the coding region (5'-upstream and 3'-downstream sequences) as well as intervening sequences, the so-called introns, which are placed between individual coding segments (so-called exons) or in the 5'-upstream or 3'-downstream region. The 5'-upstream region comprises a regulatory sequence which controls the expression of the gene, typically a promoter. The 3'-downstream region comprises sequences which are involved in termination of transcription of the gene and optionally sequences responsible for polyadenylation of the transcript and the 3' untranslated region.

The above mentioned regulatory or expression regulation sequences in addition to controlling transcription also contribute to RNA stability and processing, at least to the extent they are also transcribed.

Such expression regulation sequences are chosen to produce tissue-specific or cell type-specific expression of the recombinant DNA. Once a tissue or cell type is chosen for expression, 5' and optional. 3' expression regulation sequences are chosen. Generally, such expression regulation sequences are derived from genes that are expressed primarily in the tissue or cell type chosen. Preferably, the genes from which these expression regulation sequences are obtained are expressed substantially only in the tissue or cell type chosen, although secondary expression in other tissue and/or cell types is acceptable if expression of the recombinant DNA in the transgene in such tissue or cell type is not detrimental to the transgenic animal. Particularly preferred expression regulation sequences are those endogenous to the species of animal to be manipulated. However, expression regulation sequences from other species such as those from human genes may also be used. In some instances, the expression regulation sequences and the structural DNA sequences (either genomic or cDNA) are from the same species, e.g. each from bovine species or from a human source. In such cases, the expression regulation sequence and the DNA sequence are homologous to each other. Alternatively, the expression regulation sequences and DNA sequences (either cDNA or genomic) are obtained from different species, e.g. and expression regulation sequence from bovine species and a DNA sequence from a human source. In such cases, the expression regulation and DNA sequence are heterologous to each other. The following defines expression regulation sequences from endogenous genes. Such definitions are also applicable to expression regulation sequences from non-endogenous, heterologous genes.

In general, the 5' expression regulation sequence includes the transcribed portion of the endogenous gene upstream from the translation initiation sequence (the 5' untranslated region or 5' UTR) and those flanking sequences upstream therefrom which comprise a functional promoter. As used herein, a "functional promoter" includes those necessary untranscribed DNA sequences which direct the binding of RNA polymerase to the endogenous gene to promote transcription. Such sequences typically comprise a TATA sequence or box located generally about 25 to 30 nucleotides from the transcription initiation site. The TATA box is also sometimes referred to as the proximal signal. In many instances, the promoter further comprises one or more distal signals located upstream from the proximal signal (TATA box) which are necessary to initiate transcription. Such promoter sequences are generally contained within the first 100 to 200 nucleotides located upstream from the transcription initiation site, but may extend up to 500 to 600 nucleotides or more from the transcription initiation site. Such sequences are either readily apparent to those skilled in the art or readily identifiable by standard methods. Such promoter sequences alone or in combination with the 5' untranslated region are referred to herein as "proximal 5' expression regulation sequences".

In addition to such proximal 5' expression regulation sequences, it is preferred that additional 5' flanking sequences (referred to herein as "distal 5' expression regulation sequences") also be included in the transgene. Such distal 5' expression regulation sequences are believed to contain one or more enhancer and/or other sequences which facilitate expression of the endogenous gene and as a consequence facilitate the expression of the structural DNA sequence operably linked to the distal and proximal 5' expression regulation sequences. These 5'expression regulation sequences regulate the spatial and temporal distribution of gene expression. The amount of distal 5' expression regulation sequences depends upon the endogenous gene from which the expression regulation sequences are derived. In general, however, such sequences comprise 5' flanking regions of approximately 1 kb, more preferably 16 kb and most preferably about 30 kb of 5' flanking sequence. The determination of the optimal amount of distal 5' expression regulation sequences used from any particular endogenous gene is readily determined by varying the amount of distal 5' expression regulation sequence to obtain maximal expression. In general, the distal 5' expression regulation sequence will not be so large as to extend into an adjacent gene and will not include DNA sequences which adversely effect the level of transgene expression.

In addition, it is preferred that 3' expression regulation sequences also be included to supplement tissue or cell-type specific expression. Such 3' expression regulation sequences include 3' proximal and 3' distal expression regulation sequences from an appropriate endogenous gene. The 3' proximal expression regulation sequences include transcribed but untranslated DNA positioned downstream from the translation stop signal in the recombinant DNA sequence (also referred to as the 3' untranslated region or 3' UTR). Such sequences generally terminate at a polyadenylation sequence (either from the endogenous gene or from other sources such as SV40) and sequences that may affect RNA stability. Generally, 3' UTR's comprise about 100 to 1000 nucleotides or more downstream from the translation stop signal in the gene from which the 3' regulation sequence is derive. Distal 3' expression regulation sequences include flanking DNA sequences downstream from the proximal 3' expression regulation sequence. Some of these distal sequences are transcribed, but do not form part of the mRNA while other sequences in this 3' distal expression regulation sequence are not transcribed at all. Such distal 3' expression regulation sequences are believed to contain enhancer and/or other sequences which enhance expression. Such sequences are believed to be necessary for efficient polyadenylation and contain transcription termination sequences. Preferably, such sequences comprise about 2 kb, more preferably 8 kb and most preferably about 15 kb of 3' flanking sequence.

Although the use of both 5' and 3' expression regulation sequences are preferred, in some embodiments of the invention, endogenous 3' regulation sequences are not used. In such cases, the 3' proximal expression regulation sequences normally associated with the genomic DNA encoded by the recombinant DNA sequence are used to direct polyadenylation. In addition, distal 3' regulation sequences from the genomic DNA encoding the recombinant polypeptide may also be employed preferably in the same amounts as set forth for endogenous 3' expression regulation sequences. In such cases, it is to be understood that the recombinant polypeptide encoded by the transgene may comprise either genomic DNA or a double stranded DNA derived from cDNA. As with the 5' expression regulation sequences, the optimal amount of 3' expression regulation sequence may be readily determined by varying the amount of 3' flanking sequence to obtain maximal expression of the recombinant polypeptide. In general, the distal 3' regulation sequence, be it from an endogenous gene or a heterologous gene, will not extend into the adjacent gene from which it is derived and will exclude any sequences which adversely effect the level of transgene expression.

In addition to the 5' and 3' expression regulation sequences and the recombinant DNA (either genomic or derived from cDNA) the transgenes of the invention preferably also comprise an intron sequence which interrupts the transcribed region of the transgene. Recombinant intervening sequences may, however, also comprise a "hybrid intervening sequence". Such hybrid intervening sequences comprise a 5' RNA splice signal and 3' RNA splice signal from intervening sequences from heterologous or homologous sources.

Such hybrid intervening sequences containing permissive RNA splice signals are preferably used when the recombinant DNA corresponds to a cDNA sequence.

Based on the foregoing, it is apparent that preferred transgenes include large amounts of 5' and 3' expression regulation sequences. Further, the recombinant DNA is preferably derived from genomic clones which may be tens to hundreds of kilobases in length. Based on the present technology for cloning and manipulating DNA, the construction and microinjection of transgenes is practically limited to linearized DNA having a length not greater than about 50 kb. However, the transgenes of the invention, especially those having a length greater than about 50 kb, may be readily generated by introducing two or more overlapping fragments of the desired transgene into an embryonal target cell. When so introduced, the overlapping fragments undergo homologous recombination which results in integration of the fully reconstituted transgene in the genome of the target cell. In general, it is preferred that such overlapping transgene fragments have 100% homology in those regions which overlap. However, lower sequence homology may be tolerated provided efficient homologous recombination occurs. If non-homology does exist between the homologous sequence portions, it is preferred that the non-homology not be spread throughout the homologous sequence portion but rather be located in discrete areas.

Although as few as 14 base pairs at 100% homology are sufficient for homologous recombination in mammalian cells (Rubnitz, J. and Subramani, S. (1984) *Mol. Cell. Biol.* 4, 2253–2258), longer homologous sequence portions are preferred, e.g. 500 bp, more preferably 1000 bp, next most preferably 2000 bp and most preferably greater than 2000 bp for each homologous sequence portion.

When the transgene of the invention encodes a recombinant polypeptide that is encoded by recombinant DNA derived from or corresponding to genomic DNA (or comprised substantially of such genomic sequences. e.g. greater than about 50%, more preferably grater than about 75%, most preferably greater than 90% of the codons encoding the recombinant polypeptide are from genomic sequences), the molar concentrations and protein levels in bovine transgenic milk are the same as for cDNA or higher. In general, the molar concentration of the recombinant polypeptide in such transgenic milk is preferably greater than about 50 $\mu$M, more preferably greater than about 150 $\mu$M, most preferably greater than about 500 $\mu$M. When viewed from the level of protein in the transgenic milk, the levels are preferably greater than about 1 mg/ml, more preferably greater than about 2.5 mg/ml, most preferably greater than 5 mg/ml.

The foregoing molar concentration and protein levels in bovine transgenic milk will vary depending upon the molecular weight of the particular recombinant polypeptide. A particular advantage of producing a recombinant polypeptide in bovine transgenic milk is that relatively large molecular weight polypeptides may be so produced which are otherwise difficult to produce in large quantities in other systems such as prokaryotic expression systems.

The mouse, however, normally produces between 55 to 80 milligrams of protein per ml of milk. A cow, on the other hand, normally produces between 30 to 34 milligrams of protein per ml. Since exceptionally high levels of recombinant polypeptide production may adversely affect the production of endogenous milk protein and/or have adverse effects upon the mammary secretory gland, it is preferred that the recombinant polypeptide concentration be between about 1 and 50% of the normal bovine milk protein concentration (i.e., between about 0.3 and 17 milligrams of recombinant polypeptide per ml of transgenic milk), more preferably between 10 to 20% (i.e., between 3 to about 7 milligrams per ml) and most preferably between 10 and 15% (i.e., between about 3 and 5 milligrams per ml) of the normal amount of protein produced in bovine milk. Such preferred ranges also provide a preferred maximum limit to the aforementioned levels of protein produced in transgenic bovine milk.

The term "effective subsequence" of the gene is to be understood in the same manner as defined above in connection with the DNA sequence. The hybridization may be carried out as described in the "Definition"part of the Examples below, preferably on the basis of a probe comprising the coding part of the DNA sequence shown in the SEQ ID NO:1 below. The terms "homologous" and "effective subsequences" are used in a similar manner as that defined above.

Preferably, the polypeptide encodes by the analogue of the DNA sequence is at least 90% homologous, such as at least 95% or even 98% homologous with the amino acid sequence shown in SEQ ID NO:2.

Examples of specific analogues of the DNA sequence of the invention are DNA sequences which comprises an essential part of or the complete DNA sequence shown in SEQ ID NO:1 particularly adapted for expression in a bacteria as *E. coli,* yeast, a mammalian cell system or a transgenic animal. This DNA sequence is one which, when inserted in the expression system together with suitable regulatory sequences, results in the expression of a polypeptide having the amino acid sequence shown in SEQ ID NO:2 or an analogue or a subsequence thereof.

As mentioned above, the DNA sequence shown in SEQ ID NO:1 encodes a polypeptide comprising the functional domain/domains of human $\epsilon$-casein as well as the signal peptide naturally associated therewith. While the presence of a signal peptide in most cases is a prerequisite for allowing the polypeptide expressed from the DNA sequence to be transported out of the cell in which it is produced, the nature and origin of the particular signal peptide to be used may vary and need not be the signal peptide naturally associated with the human $\epsilon$-casein.

In accordance herewith, a particularly interesting DNA sequence of the invention is a DNA sequence which encodes a polypeptide comprising amino acids 21–182 in SEQ ID NO:2, i.e. the amino acids corresponding to the mature human $\epsilon$-casein.

Human $\epsilon$-casein is highly glycosylated at serine and threonine residues in the C-terminal part, and this glycosylated part of $\epsilon$-casein is believed to give the molecule its antimicrobial effect.

The glycosylation of a recombinant polypeptide is dependent of the selected expression system. It is well known that eukaryotic cells of different species and/or tissue origin shown variation in the glycosylation machinery. Thus, to achieve the glycosylation modifications of interest, it is critical to select a host organism for the production of the recombinant molecule, which have the capacity to perform the appropriate post-translational glycosylation modifications.

However, there are methods available that allow the modification of the glycosylation machinery of a host organism. This can be done by altering the genome of the host organism, for example a host cell or a transgenic animal, by introduction of recombinant genetic elements. These genetic elements can either encode additional or modified glycosyltransferases or other involved enzymes, and mediate their expression, or inhibit the function of endogenous glycosyltransferases or other involved enzymes. Inhibition can be achieved by knocking-out endogenous glycosyltransferase gene functions or by introduction of vectors encoding RNA sequences which are complementary to endogenous glycosyltransferase mRNA species, thereby function as antisense RNA.

The polypeptide encoded by the modified DNA sequence has normally an amino acid sequence which is different from the amino acid sequence of the human $\epsilon$-casein. It will be understood that a modified DNA sequence of the invention will be of importance in the preparation of novel polypeptides having a modified activity as compared to human $\epsilon$-casein or digestive fragments thereof or other similarly important activities.

When "substitution" is performed, one or more nucleotides in the full nucleotide sequence are replaced with one or more different nucleotides; when "addition" is performed, one or more nucleotides are added at either end of the full nucleotide sequence; when "insertion" is performed one or more nucleotides within the full nucleotide sequence is inserted; and when "deletion" is performed one or more nucleotides are deleted from the full nucleotide sequence whether at either end of the sequence or at any suitable point within it.

A modified DNA sequence may be obtained by well-known methods, e.g., by use of site-directed mutagenesis.

An example of an important modified DNA sequence of the invention is a DNA sequence in which additional codons encoding serine or threonine residues have been inserted so as to result in a modified DNA sequence encoding a polypeptide having an increased number or residues to be glycosylated and/or phosphorylated. The additional residues may be inserted either by being added at either end or within a DNA sequence of the invention or by replacing one or more non-serine or non-threonine codons present in a DNA sequence of the invention. A polypeptide encoded by such a modified DNA sequence is contemplated to have a higher degree of glycosylation and/or phosphorylation. The polypeptide produced from such a modified DNA sequence may be used as a nutrition supplement and/or as a pharmaceutical e.g. combined with a pharmaceutically acceptable carrier or vehicle by methods well known within the art.

Another example of an interesting modified DNA sequence is a DNA sequence which encodes the amino acid sequence of a naturally-occurring human ε-casein variant having an amino acid sequence different from the one shown in SEQ ID NO:2. For this purpose, site-directed mutagenesis would be carried out using specific oligonucleotide probes conferring an exchange/removal of the relevant amino acids residues.

Another important use of a DNA sequence of the invention as defined above is in the preparation of a fusion protein comprising on the one hand a polypeptide comprising the amino acid sequence shown in ID SEQ NO:2 or an analogue or subsequence thereof as defined above and on the other hand a polypeptide of another origin, e.g. a polypeptide or peptide part of another milk protein, e.g. a human milk protein such α-lactalbumin, or a milk protein such as a bovine or ovine milk protein such as bovine ε-casein. The fusion protein may be prepared by fusing a DNA sequence of the invention with a DNA sequence encoding the other part of the fusion protein and the proper regulatory sequences in a manner which allows the expression of the fusion protein to occur.

The DNA sequences of the invention explained herein may comprise natural as well as synthetic DNA sequences, the natural sequence typically being derived directly from cDNA or genomic DNA, normally of mammalian origin, e.g. as described below. A synthetic sequence may be prepared by conventional methods for synthetically preparing DNA molecules. Of course, also the DNA sequence may be of mixed cDNA and genomic, mixed cDNA and synthetic and mixed genomic and synthetic origin. Also RNA sequences may be used as described above.

The terms "sequence", "subsequence", "analogue" and "polypeptide" as used herein with respect to sequences, subsequences, analogues and polypeptides according to the invention should of course be understood as not comprising these phenomena in their natural environment, but rather, e.g., in isolated, purified, in vitro or recombinant form. When reference is made to a DNA sequence of the invention this should be understood to include "analogues", "subsequences" and "modified sequences" as define above. Similarly, when reference is made to "a polypeptide of the invention" this should be understood to include any of the polypeptides defined in the following.

In another important aspect, the present invention relates to a polypeptide encoded by a DNA sequence of the invention as defined above. A particularly interesting polypeptide of the invention is a recombinant human ε-casein polypeptide comprising the amino acid sequence shown in ID SEQ NO:2 or a subsequence thereof having a biological activity of human ε-casein. An example of an important polypeptide comprising an important subsequence of said amino acid sequence is a polypeptide comprising amino acid residues 21–182 of the amino acid sequence shown in ID SEQ NO:2 corresponding to the mature recombinant human ε-casein without a signal peptide.

As it will be apparent from the above disclosure, another interesting polypeptide of the present invention is one which differs from a polypeptide comprising the amino acid sequence shown in SEQ ID NO:2 in that at least one amino acid residue has been substituted with a different amino acid residue and/or in that at least one amino acid residue has been deleted or added so as to result in a polypeptide comprising an amino acid sequence being different from the amino acid sequence shown in SEQ ID NO:2 and having a similar or increased biological activity as compared to the activity of human ε-casein. Examples of a strategy for designing and preparing modified polypeptides of the invention are apparent from the above disclosure.

Yet another interesting polypeptide of the present invention is one in which at least one amino acid residue has been modified by posttranslational modification such as glycosylation, phosphorylation, acetylation or methylation. Evidently, the polypeptide can be subjected to more than one type of posttranslational modification. In certain presently preferred embodiment, the polypeptides of the invention are preferably in glycosylated form. Normally, glycosylation is achieved when the polypeptide is expressed by a cell of a higher organism such as yeast or preferably a mammal as described above.

Glycosylation is normally found in connection with amino acid residues Asn, Ser, Thr or hydroxylysine.

In a further aspect, the present invention relates to a replicable expression vector which carries and is capable of mediating the expression of a DNA sequence encoding human ε-casein.

In the present context, the term "replicable" means that the vector is able to replicate in a given type of host cell into which it has been introduced. Immediately upstream of the human ε-casein DNA sequence there may be provided a sequence coding for a signal peptide, the presence of which ensures secretion of the human ε-casein expressed by host cells harboring the vector. The signal sequence may be the one naturally associated with the human ε-casein DNA sequence or of another origin.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated. Examples of suitable vectors are bacterial expression vectors e.g. as exemplified in Example 5, and expression vectors designed for expression in mammalian cell systems, e.g. as exemplified in Example 6. The vector of the invention may carry any of the DNA sequences of the invention as defined above and be used for the expression of any of the polypeptides of the invention defined above.

The present invention thus also relates to a replicable expression vector selected from the group consisting of the expression vectors designated pS 330, 339, 415 and 425 and which have been deposited on Jan. 20, 1993 with the collection of Deutsche Sammlung von Mikroorganismen und Zellkulturen GmbH (DSM) under the accession numbers DSM 7410, DSM 7411, DSM 7412 and DSM 7413, in accordance with provisions of the Budapest Treaty, and expression vectors expressing DNA sequences which differ from the DNA sequences of the said deposited expression vectors, but which code for the same polypeptide or an analogue or variant thereof which has a biological activity of human κ-casein as well as a replicable expression as defined above, wherein the DNA sequence expressed is one which differs from the DNA sequence of the deposited vector in that at least one nucleotide has been deleted, substituted or modified or at least one additional nucleotide has been inserted so as to result in a DNA sequence which encodes a polypeptide having a biological activity of κ-casein.

Furthermore, the present invention relates to a plasmid selected from the group consisting of the plasmid designated pS 270, which has been deposited on Jan. 20, 1992 with the collection of Deutsche Sammlung von Mikroorganismen und Zellkulturen GmbH (DSM) under the accession number DSM 6878 in accordance with the provisions of the Budapest Treaty, the plasmids designated pS 459 and 460 which have been deposited on Jan. 20, 1993 with the collection of Deutsche Sammlung von Mikroorganismen und Zellkulturen GmbH (DSM) under the accession numbers DSM 7414 and DSM 7415, in accordance with the provisions of the Budapest Treaty, and plasmids having a DNA sequence which differs from the DNA sequence shown in SEQ ID NO:1, but which codes for the polypeptide shown in SEQ ID NO:2 or an analogue or variant thereof which has a biological activity of human κ-casein, or which hybridizes with the DNA sequence SEQ ID NO:1 or a part thereof under stringent hybridization conditions.

The present invention further relates to a cell harboring a replicable expression vector as defined above. In principle, this cell may be of any type of cell, i.e. a prokaryotic cell such as a bacterium, e.g. *E. coli*, a unicellular eukaryotic organism, a fungus or yeast, e.g. *Saccharomyces cerevisiae* or a cell derived from a multicellular organism, e.g. a mammal. The mammalian cells are especially suitable for the purpose and are further discussed below.

In another important aspect, the invention relates to a method of producing recombinant human κ-casein, in which a DNA sequence encoding human κ-casein is inserted in a vector which is able to replicate in a specific host cell, the resulting recombinant vector is introduced into a host cell which is grown in or on an appropriate culture medium under appropriate conditions for expression of human κ-casein and the human κ-casein is recovered. The medium used to grow the cells may be any conventional medium suitable for the purpose. A suitable vector may be any of the vectors described above, and an appropriate host cell may be any of the cell types listed above. The methods employed to construct the vector and affect introduction thereof into the host cell may be any methods known for such purposes within the field of recombinant DNA, examples of which are given in Examples 5 and 6. The recombinant human κ-casein expressed by the cells may be secreted, i.e. exported through the cell membrane, dependent on the type of cell and the composition of the vector. The method outlined above is equally useful for the production of any of the polypeptides of the invention as defined above, i.e. on the basis of a DNA sequence of the invention.

If the human κ-casein is produced intracellularly by the recombinant host, that is, is not secreted by the cell, it may be recovered by standard procedures comprising cell disrupture by mechanical means, e.g. sonication or homogenization, or by enzymatic or chemical means followed by purification.

In order to be secreted, the DNA sequence encoding human κ-casein should be preceded by a sequence coding for a signal peptide, the presence of which ensures secretion of human κ-casein from the cells so that at least a significant proportion of the human κ-casein expressed is secreted into the culture medium and recovered.

In a further aspect, the present invention thus relates to a method of producing a polypeptide of the invention comprising inserting a DNA sequence as defined above in a vector which is able to replicate in a specific host cell, introducing the resulting recombinant vector into a host cell and growing the resulting cell in or on an appropriate culture medium under appropriate conditions for expression of the polypeptide and recovering the polypeptide.

In a specific embodiment, the present invention thus relates to a method of isolating a recombinant polypeptide having the amino acid sequence SEQ ID NO:2 or an analogue or variant thereof which has a biological activity of human κ-casein from mammalian, bacterial or yeast cells in which it is substantially intracellularly produced, comprising separating the cells harboring the recombinant polypeptide from the culture medium, rupturing the separated cells so as to release their content of recombinant polypeptide, optionally removing cell debris from the mixture of ruptured cells, and isolating the polypeptide. In another embodiment, the present invention relates to a method wherein the human κ-casein is isolated from a culture of bacterial, mammalian or yeast cells and wherein the human κ-casein is substantially extracellularly produced; then the method can be performed essentially as outlined above, the separation and the rupturing steps being replaced by a step wherein the bacterial, mammalian or yeast cells are removed from the culture medium.

The present invention also relates to a recombinant polypeptide having the amino acid sequence 21–182 in SEQ ID NO:2 or an analogue or variant thereof which has a biological activity of human κ-casein as such as well as to a recombinant polypeptide having a subsequence of the amino acid sequence SEQ ID NO:2 or an analogue or variant of said amino acid sequence, the resulting polypeptide having a biological activity of human κ-casein. Moreover, the present invention relates to a polypeptide according to the invention wherein at least one amino acid residue has been substituted with a different amino acid residue and/or in which at least one amino acid residue has been deleted or added so as to result in a polypeptide comprising an amino acid sequence being different from the amino acid sequence shown in SEQ ID NO:2 and having a biological activity of human κ-casein.

In particular, the present invention relates to a recombinant polypeptide according to the invention in which at least one amino acid residue has been modified by post-translational modification such as glycosylation.

Although recombinant production of human κ-casein as disclosed above and described in Examples 5 or 6 using lower organisms such as bacteria or yeast or mammalian cell lines as production organisms for some purposes is satisfactory, e.g. when moderate yields of human κ-casein are sufficient, when a short-term production is desirable or when human κ-casein of a high purity substantially free from other mammalian derived substances such as proteins, in particular milk proteins, are desirable, the presently preferred method of producing recombinant human κ-casein of the invention is by use of transgenic non-human mammals capable of excreting the human κ-casein into their milk. The use of transgenic non-human mammals has the advantage that large yields of recombinant human κ-casein are obtainable at reasonable costs and, especially when the non-human mammal is a cow, goat, sheep, lama, camel, mouse, rat, rabbit, or pig, that the recombinant human κ-casein is produced in milk which is the normal constituent of, e.g., infant formulae so that no extensive purification is needed when the recombinant human κ-casein is to be used as a nutrient supplement in milk-based products. Furthermore, production in a higher organism such as a non-human mammal normally leads to the correct processing of the mammalian protein, e.g. with respect to post-translational processing as discussed above and proper folding. Also large quantities of substantially pure human κ-casein may be obtained.

Accordingly, in a further important aspect, the present invention relates to a mammalian expression system comprising a DNA sequence encoding human κ-casein inserted into a gene encoding a milk protein of a mammal so as to form a hybrid gene which is expressible in the mammary gland of an adult female of a non-human mammal harboring said hybrid gene.

The DNA sequence encoding human κ-casein is preferably a DNA sequence as defined above encoding a polypeptide comprising the amino acid sequence shown in SEQ ID NO:2 or a human κ-casein gene or an analogue or effective subsequence thereof.

The mammary gland as a tissue of expression and genes encoding milk proteins are generally considered to be particularly suitable for use in the production of heterologous proteins in transgenic non-human mammals as milk proteins are naturally produced at high expression levels in the mammary gland. Also, milk is readily collected and available in large quantities. In the present connection the use of milk protein genes in the production of recombinant human κ-casein has the further advantage that it is produced under conditions similar to the its natural production conditions in terms of regulation of expression and production location (the mammary gland). In the present context the term "hybrid gene" denotes a DNA sequence comprising on the one hand a DNA sequence encoding human κ-casein as defined above and on the other hand a DNA sequence of the milk protein gene which is capable of mediating the expression of the hybrid gene product. The term "gene encoding a milk protein" or "milk protein gene" denotes an entire gene as well as an effective subsequence thereof capable of mediating and targeting the expression of the hybrid gene to the tissue of interest, i.e. the mammary gland. The milk protein gene may be the gene for β-lactoglobulin, α-lactalbumin or a casein, but the whey acid protein gene is particularly preferred. Normally, the effective subsequence is one which at least harbours one or more of a promoter region, a transcriptional start site, 3' and 5' non-coding regions and structural sequences. The DNA sequence encoding human κ-casein is preferably substantially free from prokaryotic sequences, such as vector sequences, which may be associated with the DNA sequence after, e.g., cloning thereof.

The hybrid gene is preferably formed by inserting in vitro the DNA sequence encoding human κ-casein into the milk protein gene by use of techniques known in the art. Alternatively, the DNA sequence encoding human κ-casein can be inserted in vivo by homologous recombination.

Normally, the DNA sequence encoding human κ-casein will be inserted in one of the first exons of the milk protein gene of choice or an effective subsequence thereof comprising the first exons and preferably a substantial part of the 5' flanking sequence which is believed to be of regulatory importance.

The hybrid gene preferably comprises a sequence encoding a signal peptide so as to enable the hybrid gene product to be secreted correctly into the mammary gland. The signal peptide will typically be the one normally found in the milk protein gene in question or one associated with the DNA sequence encoding human κ-casein. However, also other signal sequences capable of mediating the secretion of the hybrid gene product to the mammary gland are relevant. Of course, the various elements of the hybrid gene should be fused in such a manner as to allow for correct expression and processing of the gene product. Thus, normally the DNA sequence encoding the signal peptide of choice should be precisely fused to the N-terminal part of the DNA sequence encoding human κ-casein. In the hybrid gene, the DNA sequence encoding human κ-casein will normally comprise its stop codon, but not its own message cleavance and polyadenylation site. Downstream of the DNA sequence encoding human κ-casein, the mRNA processing sequences of the milk protein gene will normally be retained.

A number of factors are contemplated to be responsible for the actual expression level of a particular hybrid gene. The capability of the promoter as well of other regulatory sequences as mentioned above, the integration site of the expression system in the genome of the mammal, the integration site of the DNA sequence encoding human κ-casein in the milk protein encoding gene, elements conferring post-transcriptional regulation and other similar factors may be of vital importance for the expression level obtained. On the basis of the knowledge of the various factors influencing the expression level of the hybrid gene, the person skilled in the art would know how to design an expression system useful for the present purpose.

A variety of different milk proteins are secreted by the mammary gland. Two main groups of milk proteins exist, namely the caseins and the whey proteins. The composition of milk from different species varies qualitatively as well as quantitatively with respect to these proteins. Most non-human mammals produces 3 different types of casein, namely α-casein, β-casein and κ-casein. The most common bovine whey proteins are α-lactalbumin and β-lactoglobulin. The composition of milk of various origins are further disclosed in Clark et al. 1987.

The milk protein gene to be used may be derived from the same species as the one in which the expression system is to be inserted, or it may be derived from another species. In this connection it has been shown that the regulatory elements that target gene expression to the mammary gland are functional across species boundaries (which may be due to a possible common ancestor) (Hennighausen et al. 1990).

Examples of suitable genes encoding a milk protein or effective subsequences thereof to be used in the construction of an expression system of the invention are normally found among whey proteins of various mammalian origins, e.g. a whey acidic protein (WAP) gene, preferably of murine origin, and a β-lactoglobulin gene, preferably of ovine origin. Also casein genes of various origins may be found to be suitable for the transgenic production of human κ-casein, e.g. bovine aS1-casein and rabbit β-casein. The presently preferred gene is a murine WAP gene as this has been found to be capable of providing a high level expression of a number of foreign human proteins in milk of different transgenic animals (Hennighausen et al. 1990).

Another sequence preferably associated with the expression system of the invention is a so-called expression stabilizing sequence capable of mediating high-level expression. Strong indications exist that such stabilizing sequences are found in the vicinity of and upstream of milk protein genes.

The DNA sequence encoding a human κ-casein to be inserted in the expression system of the invention may be of cDNA, genomic or synthetic origin or any combination thereof. While some expression systems have been found to function best when cDNA encoding a desirable protein is used, others have been found to require the presence of introns and other regulatory regions in order to obtain a satisfactory expression (Hennighausen et al. 1990). In some cases it may be advantageous to introduce genomic structures in vector constructs compared to cDNA elements (Brinster et al. 1988). The intron and exon structure may result in higher steady state mRNA levels than obtained when cDNA based vectors are used.

In the specification, the term "intron" includes the whole of any natural intron or part thereof.

In a further aspect, the present invention relates to a hybrid gene comprising a DNA sequence encoding human κ-casein inserted into a gene encoding a milk protein of a mammal, the DNA sequence being inserted in the milk protein gene in such a manner that it is expressible in the mammary gland of an adult female of a non-human mammal harboring the hybrid gene. The hybrid gene and its constituents have been discussed in detail above. The hybrid gene constitutes an important intermediate in the construction of an expression system of the invention as disclosed above.

In another aspect, the present invention relates to a non-human mammalian cell harboring an expression system as defined above. The mammalian cell is preferably an embryo cell or a pro-nucleus. The expression system is suitably inserted in the mammalian cell using a method as explained in the following.

In a further important aspect, the present invention relates to a method of producing a transgenic non-human mammal capable of expressing human κ-casein, comprising injecting an expression system of the invention as defined above into a fertilized egg or a cell of an embryo of a mammal so as to incorporate the expression system into the germline of the mammal and developing the resulting injected fertilized egg or embryo into an adult female mammal.

In a further important aspect, the present invention relates to a method of producing a transgenic non-human mammal capable of expressing a polypeptide having the amino acid sequence SEQ ID NO:2 or an analogue or variant thereof which has a biological activity of human κ-casein, said method comprising chromosomally incorporating a DNA sequence encoding the polypeptide into the genome of a non-human mammal.

In a further embodiment, the present invention relates to a further elaboration of the method described above comprising chromosomally incorporating a further DNA sequence encoding β-casein or an analogue, variant or subsequence thereof into the genome of a non-human mammal. This elaboration should not be limited to a DNA sequence encoding β-casein or an analogue, variant or subsequence thereof but could essentially comprise any suitable DNA sequence encoding a desired recombinant polypeptide.

The invention thus relates to a method comprising injecting an expression system encoding κ-casein or an analogue, variant or subsequence thereof and a further DNA encoding β-casein or an analogue, variant or subsequence thereof into a fertilized egg or a cell of an embryo of a mammal so as to incorporate the expression system into the germline of the mammal and developing the resulting injected fertilized egg or embryo into an adult female mammal.

In another important embodiment, the present invention relates to a method comprising 1) destroying the endogenous polypeptide expressing capability of the mammal so that substantially no endogenous polypeptide is expressed and inserting an expression system of the invention into the germline of the mammal in such a manner that the polypeptide having the amino acid sequence SEQ ID NO:2 or an analogue or variant thereof which as a biological activity of human κ-casein, is expressed in the mammal and/or 2) replacing the gene encoding the endogenous polypeptide or part thereof with an expression system of the invention thereby making said non-human mammal substantially incapable of expressing the corresponding endogenous polypeptide. In a further embodiment, the present invention relates to a method as defined above wherein the expression capability of more than one endogenous polypeptide has been destroyed. The endogenous polypeptide could be one or more caseins such as α, β or κ-casein, but are not limited to these polypeptides.

Evidently, the method of destroying the endogenous polypeptide expressing capability can be combined with the method of expressing more than one recombinant polypeptide.

The "non-human mammals" of the invention comprise all non-human mammals capable of producing a "transgenic non-human mammal" having a "desirable phenotype". Such mammals include non-human primates, murine species, bovine species, canine species, etc. Preferred non-human animals include bovine, porcine and ovine species, most preferably bovine species.

Desirable phenotypes for transgenic non-human mammals include, but are not limited to, the production of recombinant polypeptides in the milk of female transgenic non-human mammals.

The transgenic non-human mammals of the invention are produced by introducing a "transgene" into an embryonal target cell of the animal of choice. In one aspect of the invention, a transgene is a DNA sequence which is capable of producing a desirable phenotype when contained in the genome of cells of a transgenic non-human mammal. In specific embodiments, the transgene comprises a "recombinant DNA sequence" encoding a "recombinant polypeptide". In such cases, the transgene is capable of being expressed to produce the recombinant polypeptide.

The incorporation of the expression system into the germline of the mammal may be performed using any suitable technique, e.g. as described in Hogan B., Constantini, F. and Lacy, E. Manipulating the Mouse Embryo. A Laboratory Manual. Cold Spring Harbor Laboratory Press, 1986 or in WO91/08216.

Methods of introducing transgenes or overlapping transgene fragments into embryonal target cells include microinjection of the transgene into the pronuclei of fertilized oocytes or nuclei of ES cells of the non-human animal. Such methods for murine species are well known to those skilled in the art. Alternatively, the transgene may be introduced into an animal by infection of zygotes with a retrovirus containing the transgene (Jaenisch, R. (1976), *Proc. Natl. Acad. Sci.* USA, 73, 1260–1264). The preferred method is microinjection of the fertilized oocyte. In this preferred embodiment, the fertilized oocytes are first microinjected by standard techniques. They are thereafter cultured in vitro until a "pre-implantation embryo" is obtained. Such preimplantation embryos preferably contain approximately 16 to 150 cells. The 16 to 32 cell stage of an embryo is commonly referred to as a morula. Those pre-implantation embryos containing more than 32 cells are commonly referred to as blastocysts. They are generally characterized as demonstrating the development of a blastocoel cavity typically at the 64 cell stage. Methods for culturing fertilized oocytes to the pre-implantation stage include those described by Gordon et al. (1984), *Methods in Enzymology,* 101, 414; Hogan et al. (1986) in *Manipulating the Mouse Embryo,* Cold Spring Harbor Laboratory Press, Cold Spring Harbor, N.Y. (for the mouse embryo); and Hammer et al. (1985), *Nature,* 315, 680 (for rabbit and porcine embryos); Gandolfi et al. (1987) *J. Reprod. Fert.* 81, 23–28; Rexroad et al. (1988) *J. Anim. Sci.* 66, 947–953 (for ovine embryos); and Eyestone, W. H. et al. (1989) *J. Reprod. Fert.* 85, 715–720; Camous et al (1984) *J. Reprod. Fert.* 72, 779–785; and Heyman, Y. et al. (1987) *Theriogenology* 27, 5968 (for bovine embryos). Such pre-implantation embryos are thereafter transferred to an appropriate female by standard methods to permit the birth of a transgenic or chimeric animal depending upon the stage of development when the transgene is introduced. As is well known, mosaic animals can be bred to form true germline transgenic animals.

Since the frequency of transgene incorporation is often low, the detection of transgene integration in the pre-implantation embryo is highly desirable. In one aspect of the invention, methods are provided for identifying embryos wherein transgenesis has occurred and which permit implantation of transgenic embryos to form transgenic animals. In this method, one or more cells are removed from the pre-implantation embryo. When equal division is used, the embryo is preferably not cultivated past the morula stage (32 cells). Division of the pre-implantation embryo (reviewed by Williams et al. (1984) *Theriogenology* 22, 521–531) results in two "hemi-embryos" (hemi-morula or hemi-blastocyst) one of which is capable of subsequent development after implantation into the appropriate female to develop in utero to term. Although equal division of the pre-implantation embryo is preferred, it is to be understood that such an embryo may be unequally divided either intentionally or unintentionally into two hemi-embryos which are not necessarily of equal cell number. Essentially, all that is required is that one of the embryos which is not analyzed as hereinafter described be of sufficient cell number to develop to full term in utero. In a specific embodiment, the hemi-embryo which is not analyzed as described herein, if shown to be transgenic, is used to generate a clonal population of transgenic non-human animals.

One of each of the hemi-embryos formed by division of pre-implantation embryos is analyzed to determine if the transgene has been integrated into the genome of the organism. Each of the other hemi-embryos is maintained for subsequent implantation into a recipient female of the species.

The identification of the pre-implantation embryos containing the integrated transgene is achieved by analyzing the DNA from one of each of the hemi-embryos. Such DNA is typically obtained by lysing the hemi-embryo and analyzing the thus released DNA as described in Example 8. A polymerase chain reaction is performed to amplify all or part of the transgene. When the entire transgene is amplified, two extension primers each complementary to opposite strands at opposing ends of the transgene are used for amplification. Generally, the amplified DNA from the hemi-embryo is subjected to electrophoresis followed by hybridization with labeled probe complementary to the region of the transgene between the two extension primers. This facilitates the determination of the size of the amplified DNA sequences, if any, and provides an indication of whether the transgene has been integrated into the pre-implantation embryo from which the hemi-embryo was obtained (now called a "transgenic hemi-embryo"). If it has, the remaining untreated transgenic hemi-embryo is transplanted into a recipient parent. After in utero development, the transgenic non-human animal having the desired phenotype conferred by the integrated transgene is identified by an appropriate method in utero or after birth.

The above described methods for the detection of transgenesis in pre-implantation embryos provide economical and time saving methods for generating transgenic non-human animals since they significantly decrease the number of pregnancies required to produce a transgenic animal and substantially increase the likelihood that an implanted embryo will produce a transgenic non-human animal. Such methods are especially important for those animals for which very low or non-existent frequencies of transgenesis have been obtained, e.g. bovine species.

In an alternate embodiment, the above described method for detecting transgenesis in pre-implantation embryos is combined with embryonic cloning steps to generate a clonal population of transgenic embryos which may thereafter be implanted into recipient females to produce a clonal population of transgenic non-human animals also having the same genotype. In this regard, it is to be understood that transgenic embryos and/or non-human transgenic animals having the same "genotype" means that the genomic DNA is substantially identical between the individuals of the embryo and/or transgenic animal population. It is to be understood, however, that during mitosis various somatic mutations may occur which may produce variations in the genotype of one or more cells and/or animals. Thus, a population having the same genotype may demonstrate individual or subpopulation variations.

After a hemi-embryo is identified as a transgenic hemi-embryo, it is cloned. Such embryo cloning may be performed by several different approaches. In one cloning method, the transgenic hemi-embryo is cultured in the same or in a similar medium as used to culture individual oocytes to the pre-implantation stage. The "transgenic embryo" so formed (preferably a transgenic morula) is then divided into "transgenic hemi-embryos" which can then be implanted into a recipient female to form a clonal population of two transgenic non-human animals. Alternatively, the two transgenic hemi-embryos obtained may be again cultivated to the pre-implantation stage, divided, and recultivated to the transgenic embryo stage. This procedure is repeated until the desired number of clonal transgenic embryos having the same genotype are obtained. Such transgenic embryos may then be implanted into recipient females to produce a clonal population of transgenic non-human animals.

In a preferred cloning method, the transgenic embryo is cloned by nuclear transfer according to the techniques of Prather et al. (1987) *Biol. Reprod.* 37, 859–866; Roble et al. (1987) *J. Anim. Sci.* 64, 642–664. According to this method, nuclei of the transgenic embryo are transplanted into enucleated oocytes, each of which is thereafter cultured to the blastocyst stage. At this point, the transgenic embryos may be resubjected to another round of cloning by nuclear transplantation or may be transferred to a recipient parent for production of transgenic offspring having the same genotype.

In addition to the foregoing methods for detecting early transgenesis, other methods may be used to detect transgenesis. Such method include in utero and post partum analysis of tissue. In utero analysis is performed by several techniques. In one, transvaginal puncture of the amniotic cavity is performed under echoscopic guidance (Bongso et al. (1975) *Vet. Res.* 96, 124–126; Rumsey et al. (1974) *J. Anim.*

*Sci.* 39, 386–391). This involves recovering about 15 to 20 milliliters of amniotic fluid between about day 35 and day 100 of gestation. This volume of amniotic fluid contains about 1000 to 12,000 cells per ml originating from the urogenital tract, the skin and possibly the lungs of the developing embryo. Most of these cells are dead. Such cells, however, contain genomic DNA which is subjected to PCR analysis for the transgene as an indication of a successful transgenesis. Alternatively, fetal cells may be recovered by chorion puncture. This method may also be performed transvaginally and under echoscopic guidance. In this method, a needle is used to puncture the recipient animal's placenta, particularly the placentonal structures, which are fixed against the vaginal wall. Such sampling may be performed around day 60 of gestation in bovine species. Chorion cells, if necessary, are separated from maternal tissue and subjected to PCR analysis for the transgene as an indication of successful transgenesis.

Transgenesis may also be detected after birth. In such cases, transgene integration can be detected by taking an appropriate tissue biopsy such as from the ear or tail of the putative transgenic animal. About one to two centimeters of tail or about five to ten square millimeters of ear are obtained followed by souther blotting with a probe for the transgene according to the method of Hogan et al. (1986) *Manipulating the Mouse Embryo,* Cold Spring Harbor Laboratory.

Normally, not all of the injected eggs will develop into transgenic mammals capable of expressing human κ-casein. Transgenic founder animals can be identified e.g. as described in Example 8. About half of the mammals will form a statistically point of view be males. One the basis of the identified transgenic individuals—male and female— progeny can be established and stable lines of transgenic animals established.

Once integrated in the germ line, the DNA sequence encoding human κ-casein may be expressed at high levels to produce a correctly processed and functional human κ-casein. Transgenic females from which recombinant polypeptide can be harvested can thus be bred in the following generations.

Gene targeting refers to the directed modification of a selected chromosomal locus of an endogenous chromosome of a cell by homologous recombination with an exogenous DNA sequence having homology to the selected endogenous sequence. Gene targeting has been employed to enhance, modify and disrupt expression of endogenous genes (see Bollag et al. (1989) *Ann. Rev. Genet.* 23, 199–225 and WO92/03917 (homologous recombination in mammalian cells).

In a further aspect, the present invention relates to a transgenic non-human mammal prepared by a method as described above.

The DNA used to make transgenic cells and animals preferably comprises genomic DNA rather than cDNA. This is because the expression of transgenes is preferably limited to tissue-specific expression as well as temporal-specific expression. When the transgene is derived from genomic DNA, important cis-acting regulatory sequences such as enhancers and other regulatory elements, located either in introns or in regions distant from the structural gene, can be included. Such regulatory sequences are lost during transcription and RNA processing and accordingly are not generally available with cDNA-derived transgenes.

In a further aspect, the present invention relates to a transgenic non-human mammal prepared by a method as described above.

While the transgenic non-human mammal of the invention in its broadest aspect is not restricted to any particular type of mammal, the mammal will normally be selected from the group consisting of mice, rats, rabbits, sheep, pigs, goats and cattle. For large scale production of human κ-casein the larger animals such as sheep, goats, pigs and especially cattle are normally preferred due to their high milk production. However, also mice, rabbits and rats may be interesting due to the fact that the manipulation of these animals is more simple and results in transgenic animals more quickly than when, e.g. cattle, are concerned.

Also progeny of a transgenic mammal as defined above, capable of producing human κ-casein is within the scope of the present invention.

From the above explanation it will be clear that the present invention for the first time makes it possible to produce milk from a non-human mammal comprising human κ-casein, the importance and utility of which will be apparent from the present context. Thus, in a further aspects of the present invention includes milk from a non-human mammal comprising recombinant human κ-casein. Of particular interest is milk from a non-human mammal comprising a polypeptide of the invention as defined above comprising the amino acid sequence shown in SEQ ID NO:2 or a polypeptide encoded by a DNA sequence or an analogue or subsequence thereof as defined above. Typically, the milk of the invention will be obtained from a transgenic mammal of the invention as defined above.

From the above explanation it will be apparent that an important use of the polypeptide of the invention is as a nutrient supplement, in particular as a substituent of an infant formula. In particular, the present invention thus relates to an infant formula comprising a polypeptide of the invention.

In an important embodiment the present invention thus relates to a method for producing a human infant formula comprising a polypeptide having the amino acid sequence SEQ ID NO:2 or an analogue or variant thereof which has a biological activity of human κ-casein, together with at least one other infant formula constituent selected from other milk proteins, lipids, carbohydrates, vitamins, minerals and other nutrients essential to meet the nutritional requirements of a human infant, comprising introducing an expression system of the invention into the genome of non-human mammal in such a way that the DNA encoding the polypeptide having the amino acid sequence SEQ ID NO:2 or an analogue or variant thereof which has a biological activity of human κ-casein, is capable of being expressed in a mammary gland of the non-human mammal, obtaining expression of the polypeptide by said transgenic non-human mammal, harvesting and optionally purifying the polypeptide expressed by said transgenic non-human mammal, and formulating the human infant formula with said polypeptide.

In a still further aspect, the present invention relates to an infant formula comprising recombinant human κ-casein, in particular a polypeptide of the invention as defined above. In a specific embodiment, the human infant formula comprises recombinant human β-casein as well as recombinant human κ-casein. The infant formula may be prepared by adding the recombinant human κ-casein or polypeptide in a purified or partly purified form to the normal constituents of the infant formula. However, normally it is preferred that the infant formula is prepared from milk of the invention as defined above, especially when it is of bovine origin. The infant formula may be prepared using conventional procedures and contain any necessary additives such as minerals, vitamins, etc.

In another aspect, the present invention relates to a method of obtaining human κ-casein comprising collecting milk from a transgenic non-human mammal of the invention as defined above and recovering the human κ-casein from the milk. The milk may be collected in any suitable manner normally used in connection with the collection of milk from the mammal in question.

Preparation of infant formula

The formulation of infant formula based on bovine α-lactalbumin and casein has been defined (V. S. Packard, "Human Milk and Infant Formula", pp. 147–154. Academic Press (1982)). It is suggested that the whey proteins and caseins be in a ratio of 60:40 or 0.9 weight percent α-lactalbumin to 0.6 weight percent casein for a total of 1.5 g protein/100 ml of milk.

Calcium is preferably of a chemical form that is biologically compatible and commercially available, such as from SIGMA Chemical Co., and should preferably be present to a minimum of 50 mg/100 kcal. Minimum phosphorus level is 25 mg/100 kcal. Minimum and maximum amounts of sodium, potassium, and chloride must also be observed. These levels are met within the ranges 6–17, 14–34, and 11–29 milliequivalents (mEq), respectively, in a formula providing 670 kcal/liter. One milliequivalent is equal to the atomic weight (in milligrams) of the element divided by valence. Osmolarity—in moles of solute/liter—should not exceed 400 mOsm.

Caloric density of infant formulas of 670 kcal/liter appears nearly optimal for normal full-term infants. The formulation should provide a calcium-phosphorus ratio preferably of not less than 1.1:1.0 nor more than 2:1. Most preferably, the ratio is near 1.5:1, at least through most of the first year of life. By one year of age, the appropriate ratio is more nearly 1:1.

Infant formulas can vary in composition, but within fairly narrow and quite precise limits. In general, as a complete substitute for human milk, formula is preferably comprised of protein at 7–16% of calories, fat at 30–54% of calories, linoleic acid at 2–3% of calories, and the remaining calories from carbohydrate sources. The fat component of the formula is preferably comprised of various vegetable fats. Because many contaminants or pollutants of food are soluble in fat, specially refined vegetable fats and oils provide better control of formula contents. To prevent conversion of cis to trans fatty acids, and loss thereby of essential fatty acids, low- (or ultra-high) temperature treatment is preferably used throughout processing.

A representative list of ingredients follows:

Water
Lactose (corn syrup or sucrose could be used)
Human α-lactalbumin
Human β-casein
Coconut oil
Soybean oil
Modified corn starch
Mono- and diglycerides
Soy lecithin
Carrageenan
Vitamin sources
Vitamin A palmitate
Vitamin D3
α-tocopheryl acetate (vitamin E)
Phytonadione (vitamin K)
Ascorbic acid (vitamin C)
Thiamin chloride hydrochloride (vitamin B1)
Riboflavin
Cyanocobalamin (vitamin B12)
Niacinamide
Calcium pantothenate
Pyridoxine hydrochloride (vitamin B6)
Biotin
Folic acid
Choline chloride
Mineral sources
Calcium phosphate, tribasic
Cupric sulfate
Ferrous sulfate
Magnesium chloride
Potassium chloride
Potassium citrate
Potassium iodide
Zinc sulfate The amounts of each of the ingredients listed are adjusted to keep each nutritional component within the maximum and minimum guidelines recommended by the FDA (V. S. Packard, "Human Milk and Infant Formula", pp. 147–154. Academic Press (1982)) and by the American Academy of Pediatrics (Am. Acad. of Pediatrics Comm. on Nutrition *Pediatrics* 72, 359–363 (1983)), as disclosed below (modified from American Academy of Pediatrics, Committee on Nutrition: Commentary on Breast-Feeding and Infant Formulas, including proposed standards for formulas. *Pediatrics* 57, 278 (1976)).

Carbohydrates sources include lactose (or milk and whey products that contain lactose), sucrose, corn syrup solids (a source of glucose), and starch.

Appropriate thickening agents, emulsifiers, antioxidants, and compounds for adjusting pH may be used. In the United States, conditions of use of additives in infant formula are regulated under the *Code of Federal Regulations* (CFR), Title 21, Section 172.620 and Section 180. Vitamin additives for use in infant formulas are approved by the Food and Agricultural Organization (FAO). Processing requirements, availability, and/or stability in the specific food system will dictate which form(s) will serve best.

The FAO also approves mineral sources for infant formula. Suitability of any given mineral additive depends on composition and moisture level of the food product. Furthermore, each food imposes its own requirements for flavour and/or textural stability. Oxidative rancidity is an ever-present problem in iron and/or copper-fortified foods containing unsaturated fats. Gelation is a potential problem in concentrated liquid infant formulas. Reduced iron or electrolytic iron, which serve well in dry foods, will settle out as a sediment in liquid formula. FAO also recognizes the need for acids and bases for making pH adjustments; however, these must be accounted for in determining total content of any given mineral.

Certain mineral compounds, for instance calcium and phosphorus, are required in fairly large amounts in infant formula. Other mineral elements are required only in trace amounts. Thus, trace minerals in ingredients of infant formula must be considered, along with those that may be added in water supplies used to reconstitute various dry ingredients. Water supplies may or may not be treated for this purpose, depending upon the overall quality. Water quality should be monitored, however, along with the trace mineral content of finished formula.

When trace minerals are added to formula, sulfate salts are commonly used. Acceptable levels of sulfate ions, however, have not been specified (Anderson et al. (1982).

Because of the potential to cause methemoglobinemia, nitrate salts are usually not added to formula. A trace amount may occur in formula made up of vegetable products. Nitrates also occur and are occasionally found at high levels in some water supplies. Copper is another potentially toxic component of water. However, any biologically acceptable salt composition is contemplated for use in the present invention.

Minerals commonly added to formulas include calcium, phosphorus, magnesium, iron, copper, iodine, zinc, potassium, sodium, manganese, and chlorine (as chloride). Conventional infant formula compositions require the addition of bovine or soy protein sources which may have a significant amount of minerals carried along with the protein component. The presence of these minerals decreases the accuracy of determining the mineral components of the manufactured infant formula. Conventional methodologies, including electrodialysis, ion exchange and ultrafiltration, are commonly used to separate the proteins from the minerals and other contaminants associated with them. Use of the recombinant DNA-derived human proteins of the present invention in human infant formula reduces the amount of protein purification necessary, thus providing a more accurate determination of mineral content and reduced expenditures for protein processing.

Formulations for premature infants

For preterm or low-weight infants (under 2500 g), formulas are usually modified, with the evaluation of protein and mineral levels. Lactose level may preferably be lowered by one-third to one-half regular amounts, with the difference made up with more readily absorbable carbohydrates source such as corn syrup solids. Fat, calcium, and phosphorus must be available in readily utilizable form.

Caloric density is preferably raised to 800–1000 kcal/liter; with approximately 11% of the calories from protein and 50% from fat. In general, corn and soy oil appear reasonably well absorbed by premature infants. The polypeptides of the present invention are particularly well suited for infant formulae for premature infants as the casein proteins are more easily digested than whey proteins and thus constitute a very suitable protein source for premature infants as well as for other purposes where the abovestated advantageous properties of the human caseins are useful.

In addition to infant formulas, other food formulations may also be supplemented with recombinant polypeptides from transgenic bovine milk. For example, such recombinant polypeptides may be used to supplement common diet formulations.

Thus, the production of human κ-casein in the milk of transgenic bovine species provides a source of human κ-casein. Such human κ-casein may be purified from the transgenic milk for formulation purposes. Alternatively, the whole transgenic milk may be used, preferably after pasteurization, in either liquid or dried form.

LEGENDS TO FIGURES

FIG. 1 shows the plasmid pS 270 containing the full length cDNA fragment encoding human κ-casein obtained as described in Example 3.

Figure 2:
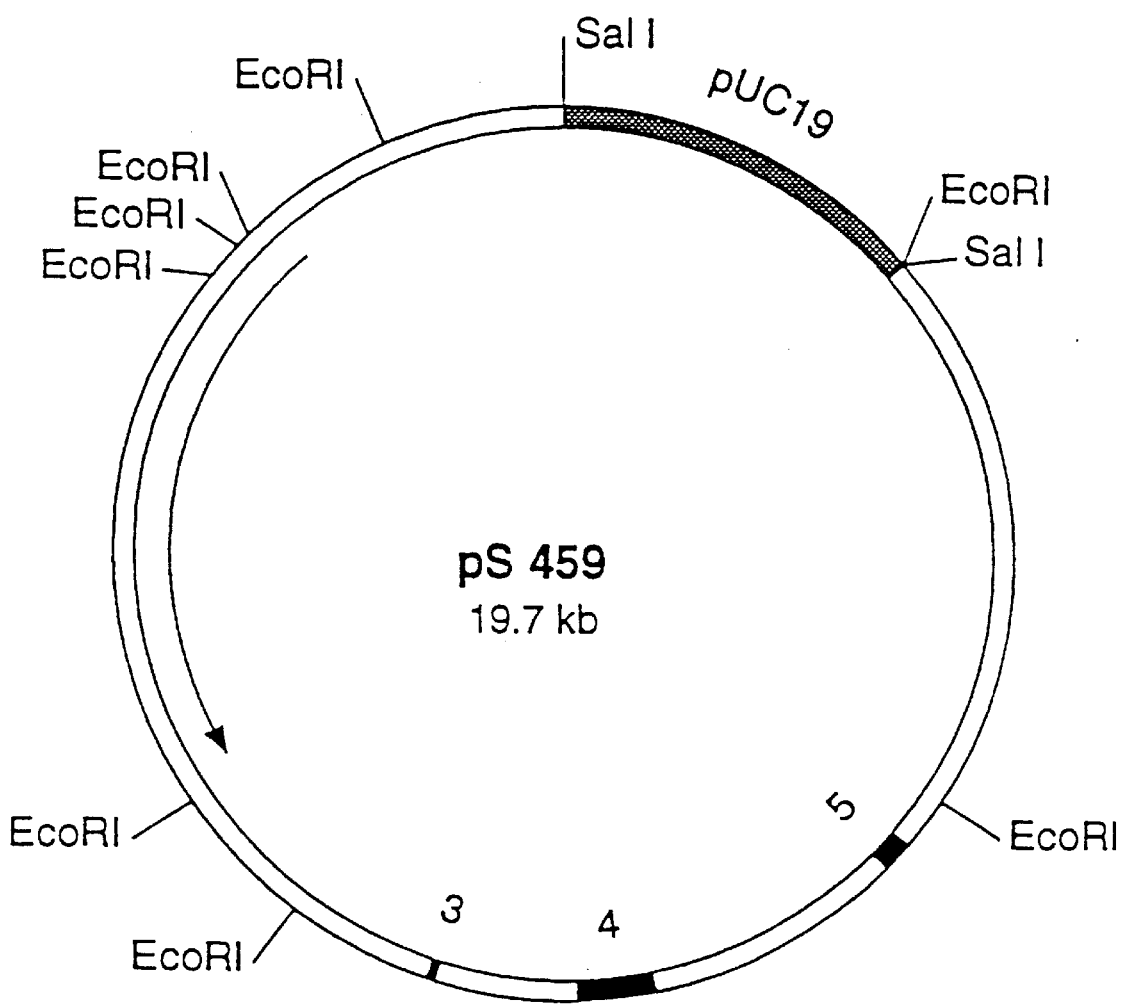

FIG. 2 shows a circular map of the plasmid pS459 which contains the human κ-casein genomic sequences derived from the purified λ phage isolate #42 cloned into SalI digested pUC19, as described in Example 4. EcoRI restriction sites are shown for orientation of the κ-casein gene fragment. The arrow dicates the transcriptional direction of the κ-casein gene. The exons are indicated as solid segments and the number indicate their position in the human κ-casein gene.

Figure 3:
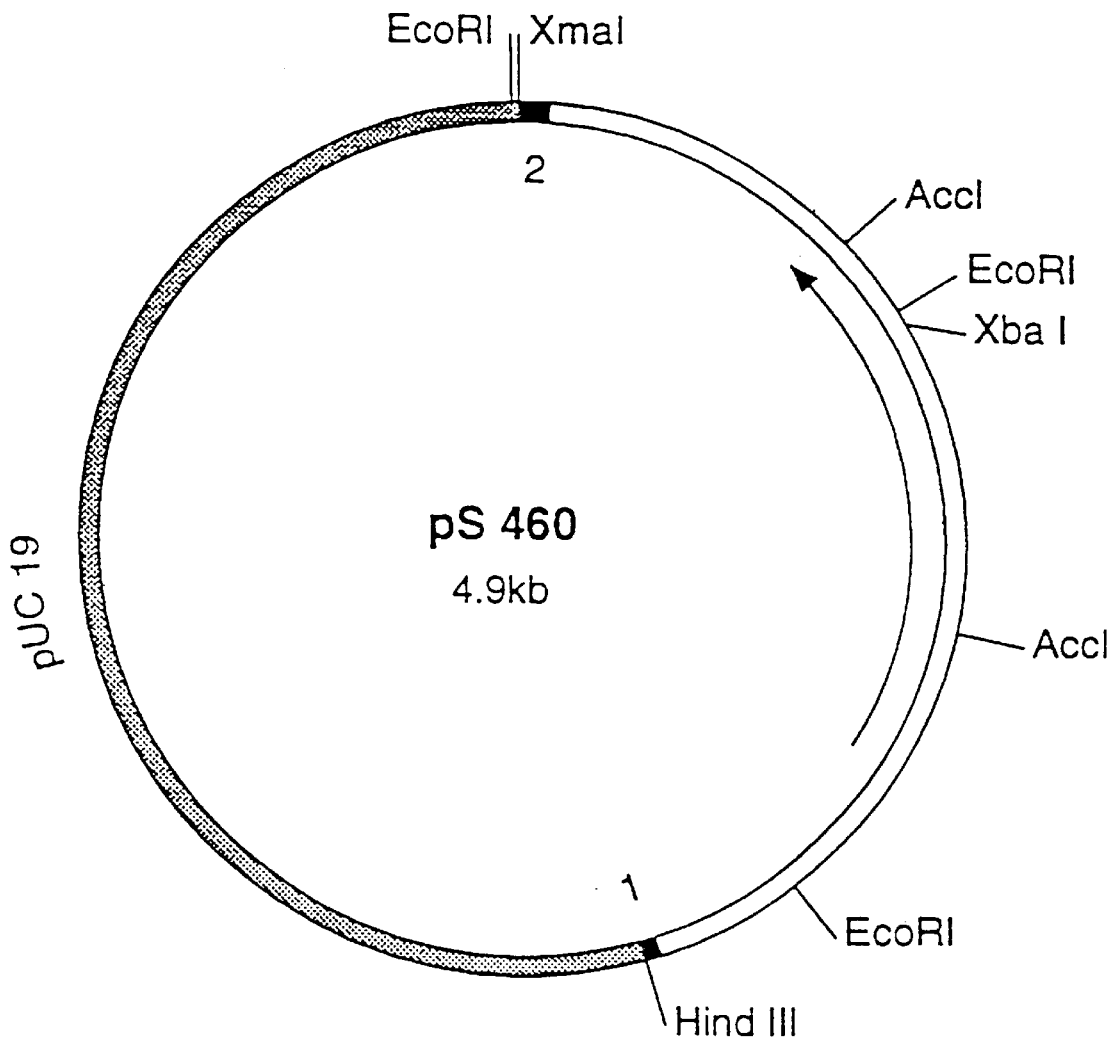

FIG. 3 shows a circular map of the plasmid pS460 which contains the genomic sequences derived from the PCR amplified region of the human κ-casein gene, cloned into XmaI and HindIII digested pUC19, as described in Example 4. Restriction sites are shown for orientation of the κ-casein gene fragment. The arrow indicates the transcriptional direction of the κ-casein gene. The exons are indicated as solid segments and the numbers indicate their position in the human κ-casein gene.

Figure 4:
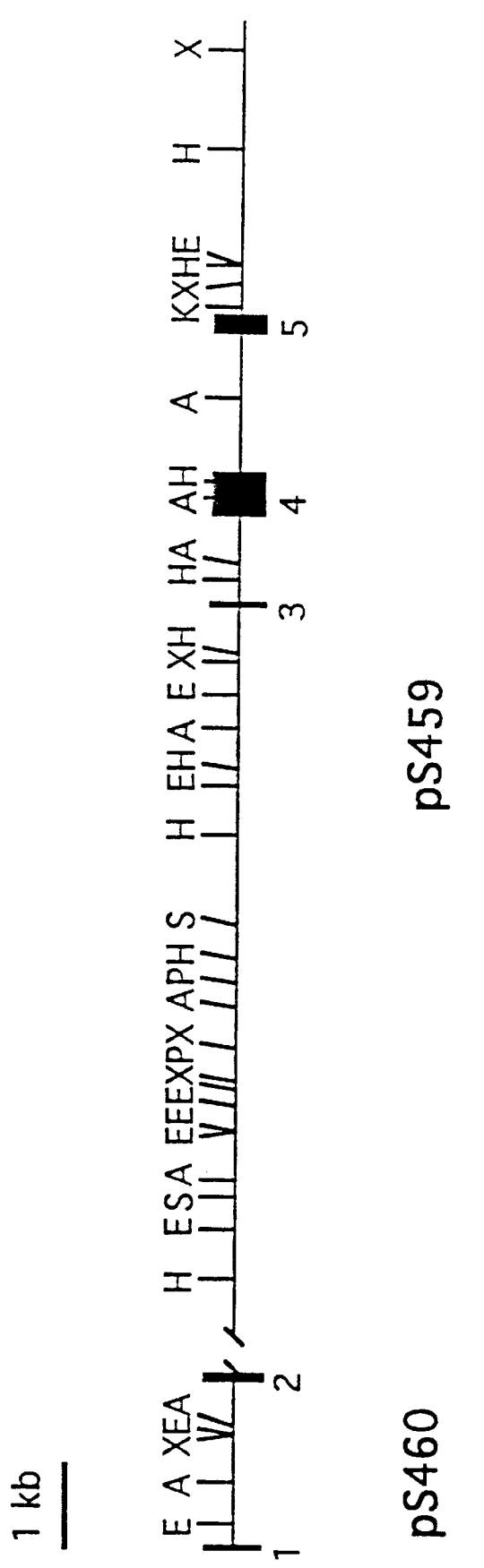

FIG. 4 shows a physical map of the human κ-casein gene locus. The exon and intron organization and position of restriction enzyme sites are shown. Exons are indicated as solid boxes number 1–5. Restriction enzymes indicated are E-EcoRI, A-AccI, X-XbaI, S-SacI, P-PstI, H-HindIII, K-KpnI. The plasmidial origin of the two genomic fragments is also indicated.

Figure 5:
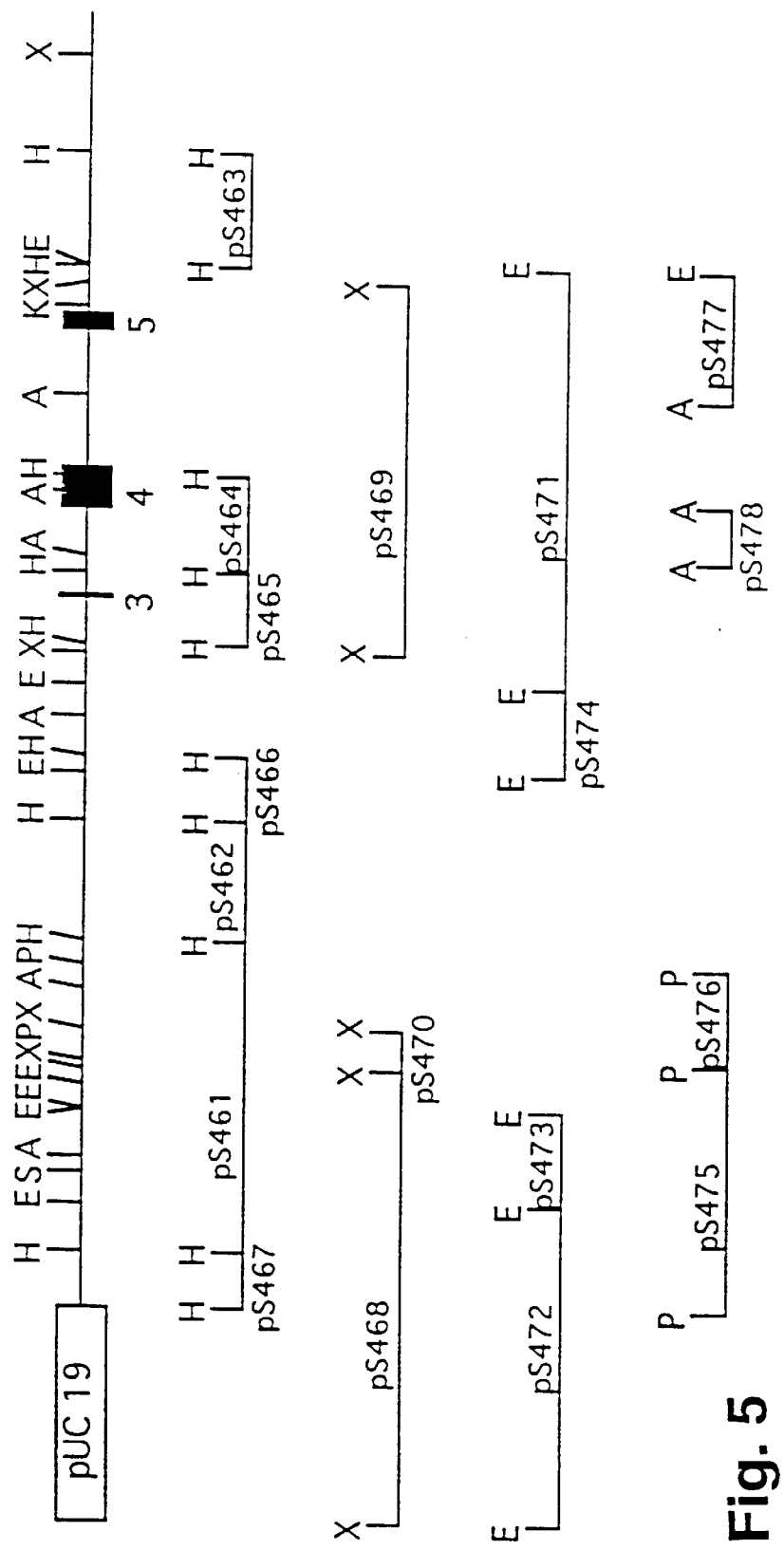

FIG. 5 shows the restriction map of pS459 and positions of the 18 different subclones, pS461–478, which were used for sequence analysis (Example 4). pS461–467 represent different HindIII fragments; pS468–470 represent different XbaI fragments: pS471–474 represent different EcoRI fragments; and pS475 and pS476 represent different PstI fragments; pS477 represents an AccI/EcoRI fragment; and pS478 represents an AccI fragment. All fragments were subcloned into pUC19. Key: H-HindIII, E-EcoRI, S-SacI, X-XbaI, P-PstI, A-AccI, K-KpnI.

Figure 6:
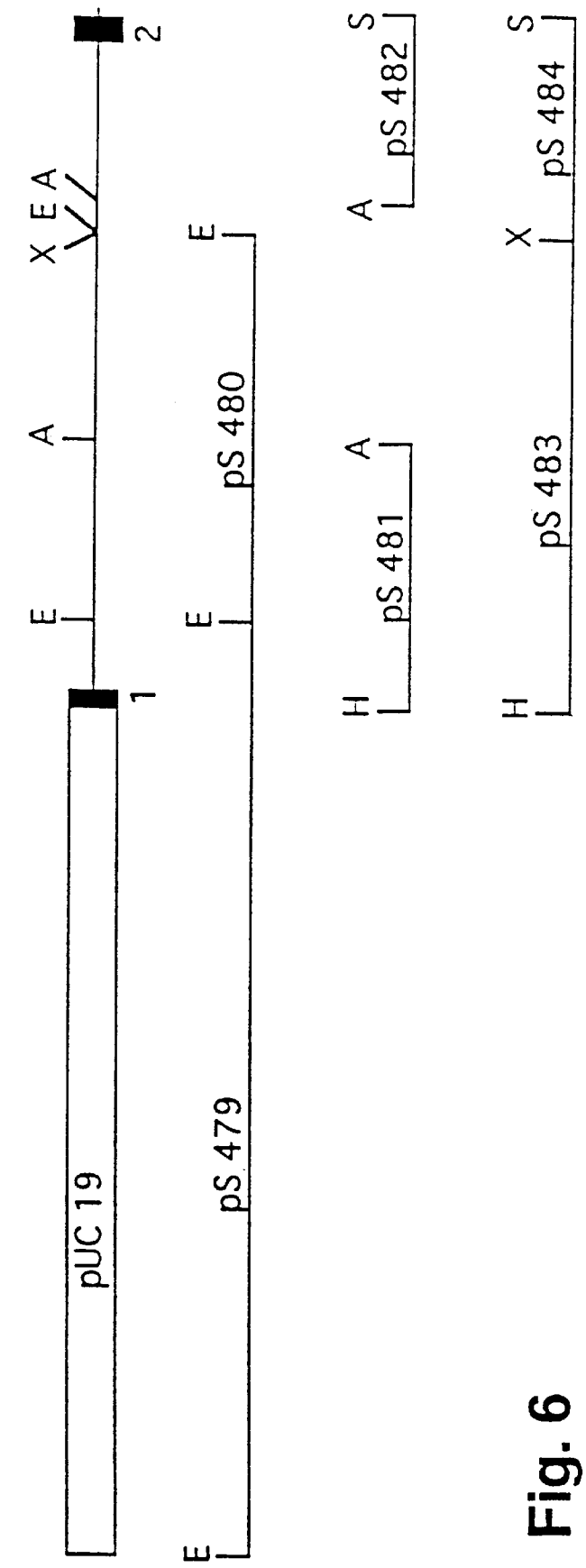

FIG. 6 shows the restriction map of pS460 and positions of the 6 different subclones, pS479–484, which were used for sequence analysis (Example 4). pS479 and pS480 represent two different EcoRI fragments; pS481 represents a HindIII/AccI fragment; pS482 represents an AccI/-SacI fragment; pS483 represents a HindIII/XbaI fragment; and pS484 represents a XbaI/SacI fragment. All fragments were subcloned into pUC19.

Key: E-EcoRI, A-AccI, X-XbaI, H-HindIII.

Figure 7:
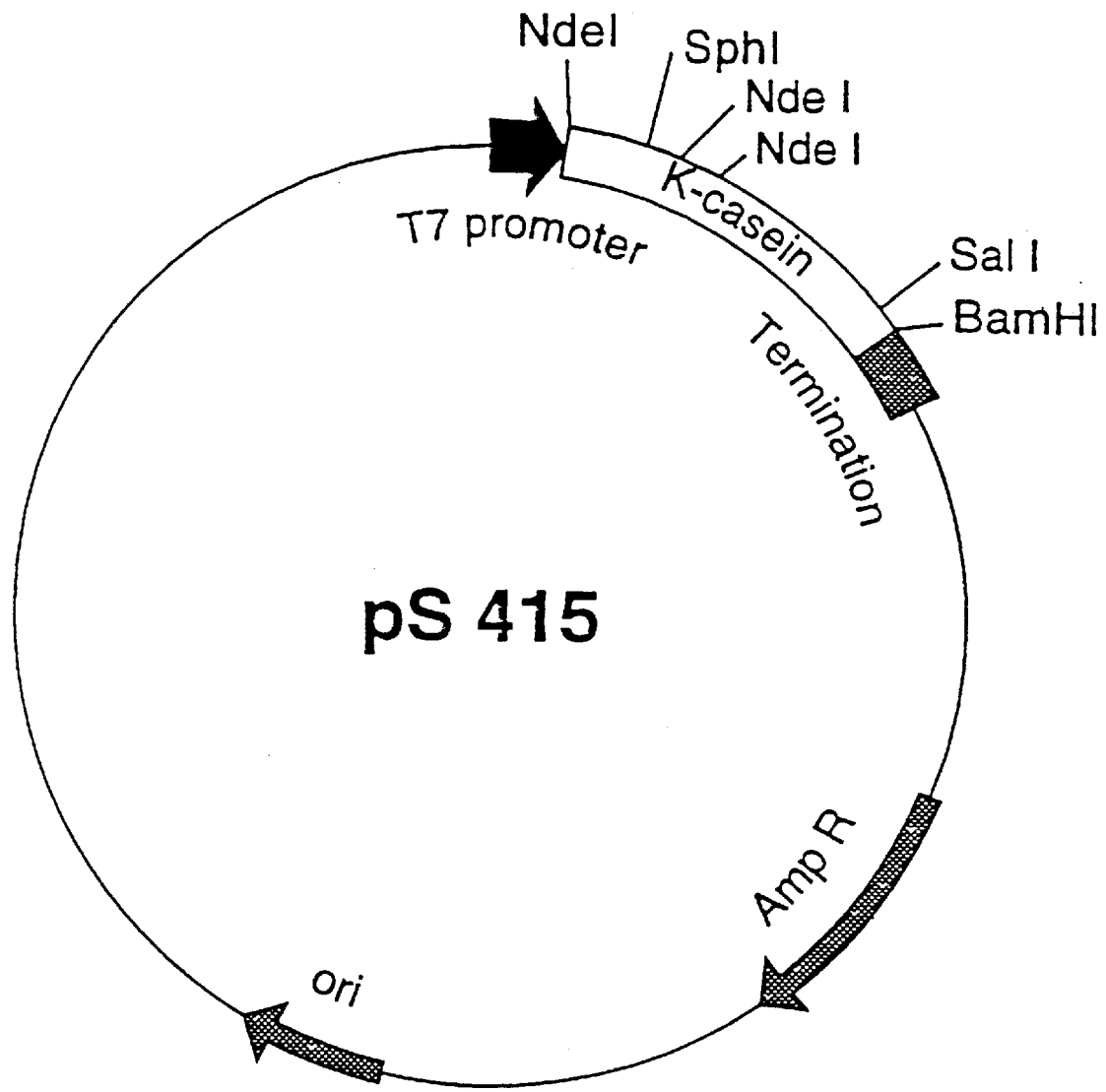

FIG. 7 shows a circular map of the expression vector pS415, constructed as described in Example 5. This expression vector mediates as described in Example 5. This expression vector mediates intracellular expression of recombinant human κ-casein in *E. coli*.

Figure 8:
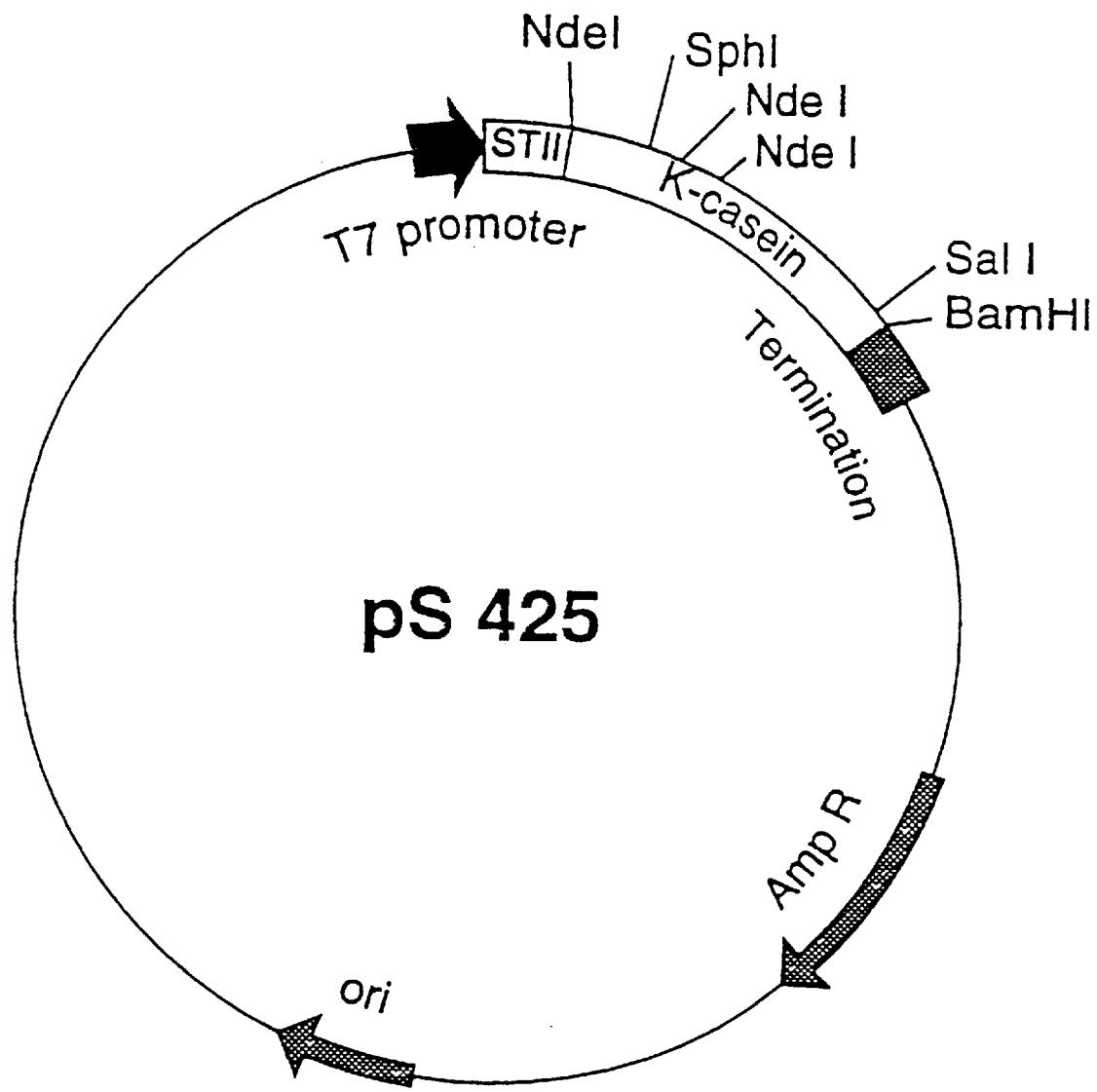

FIG. 8 shows a circular map of the expression vector pS425, constructed as described in Example 5. This expression vector mediates extracellular expression of recombinant human κ-casein in *E. coli*.

Figure 9:
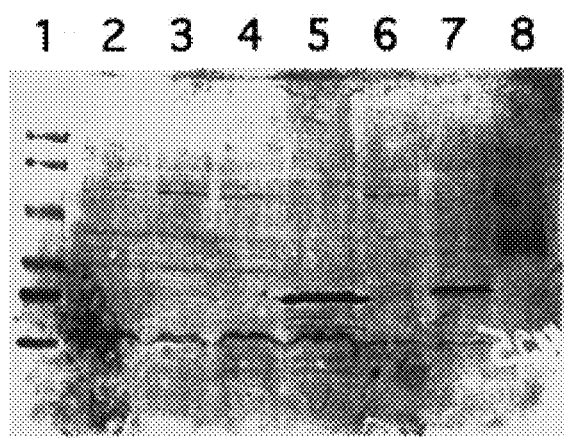

FIG. 9 shows the result of a SDS-PAGE and Western blot analysis of recombinant human κ-casein expressed in *E. coli* BL 21 (DE3) pLysS harboring the expression vectors pS14, pS415 and pS425, respectively. Bacterial cells were boiled in sample buffer and the proteins were separated. pS14 is identical to pS 415 except that it lacks κ-casein sequences and function as a negative control. The recombinant human κ-casein was visualized using alkaline labelled polyclonal rabbit antibodies raised against highly purified human κ-casein (Example 2). Culture conditions and induction methods were as described in Example 5.

Lane 1. Prestained molecular weight markers 106, 80, 49.5, 32.5, 27.5 and 18.5 kDa (BioRad).
Lane 2 Uninduced pS14
Lane 3 Induced pS14
Lane 4 Uninduced pS415
Lane 5 Induced pS415
Lane 6 Uninduced pS425
Lane 7 Induced pS425
Lane 8 Purified human κ-casein (5.00 ng)

Figure 10:
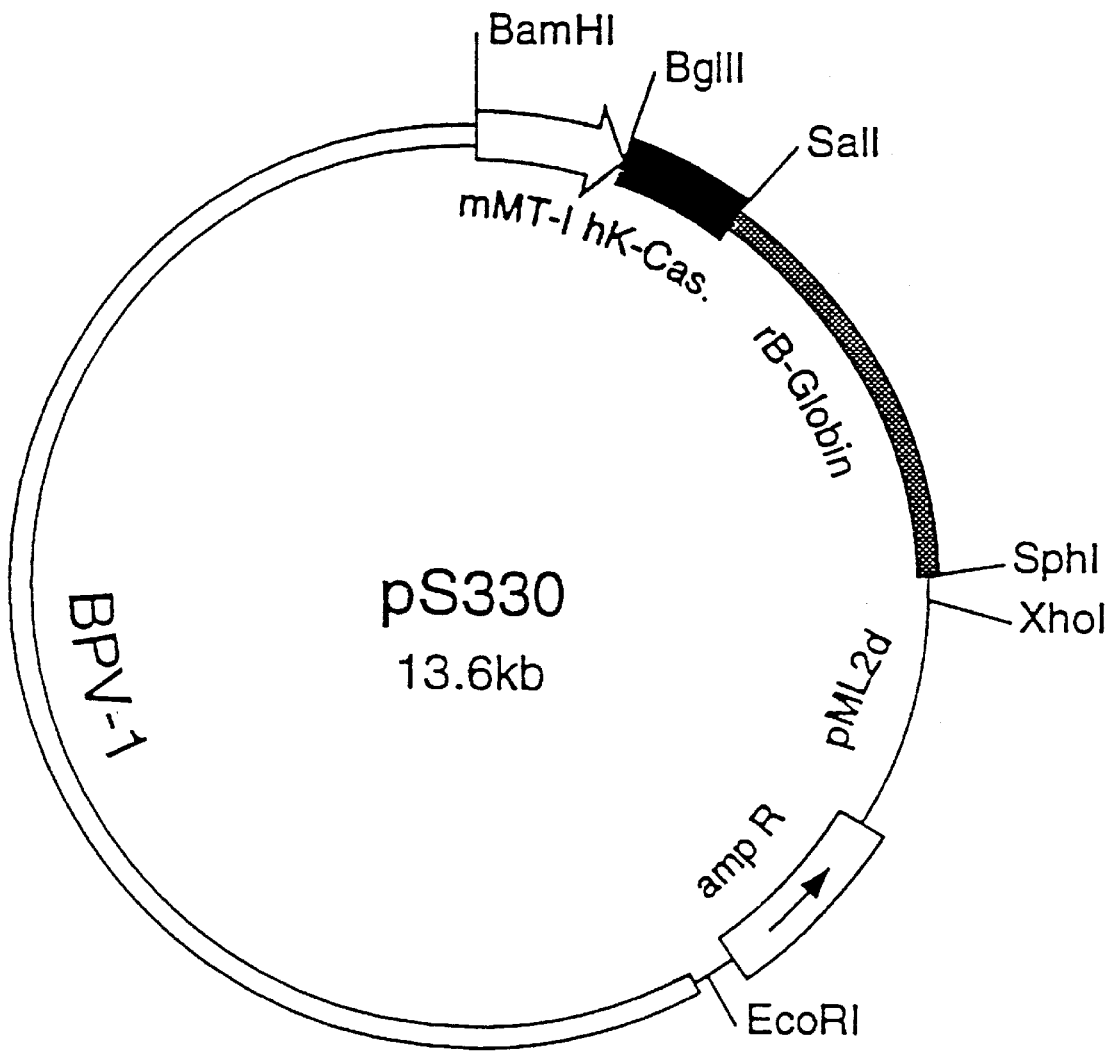

FIG. 10 shows a circular map of the expression vector pS330, constructed as described in Example 6. This expression vector mediates expression of recombinant human κ-casein in mammalian cells.

Figure 11:
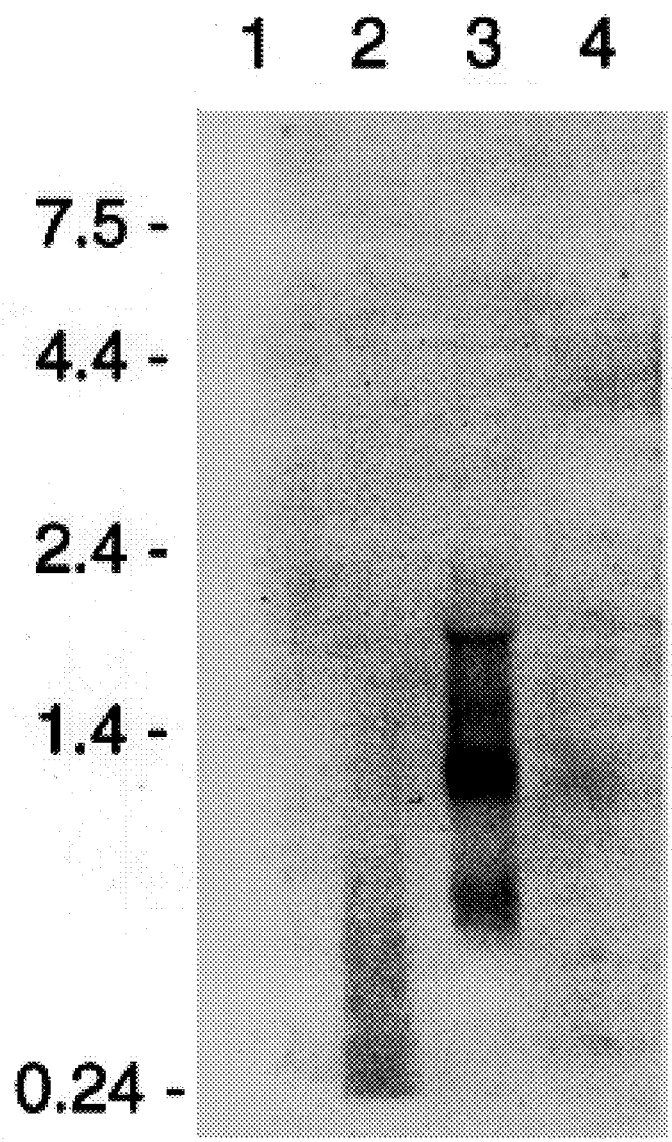

FIG. 11 shows analysis of expression of the recombinant κ-casein gene in mammalian cells. Total RNA was prepared from C127 cells and separated on a 1% Formaldehyde-agarose gel, transferred to nitrocellulose membrane and hybridized to a $^{32}$P-labelled κ-casein probe derived from pS270. Experimental procedures were according to Ausubel et al. 1991. Three different cell lines harboring the expression vector pS330 were isolated and analysed (Example 6). As a control a C217 cell line harboring the vector pS306 was used. pS306 is similar to pS330 except the absence of κ-casein encoding sequences.

Figure 12:
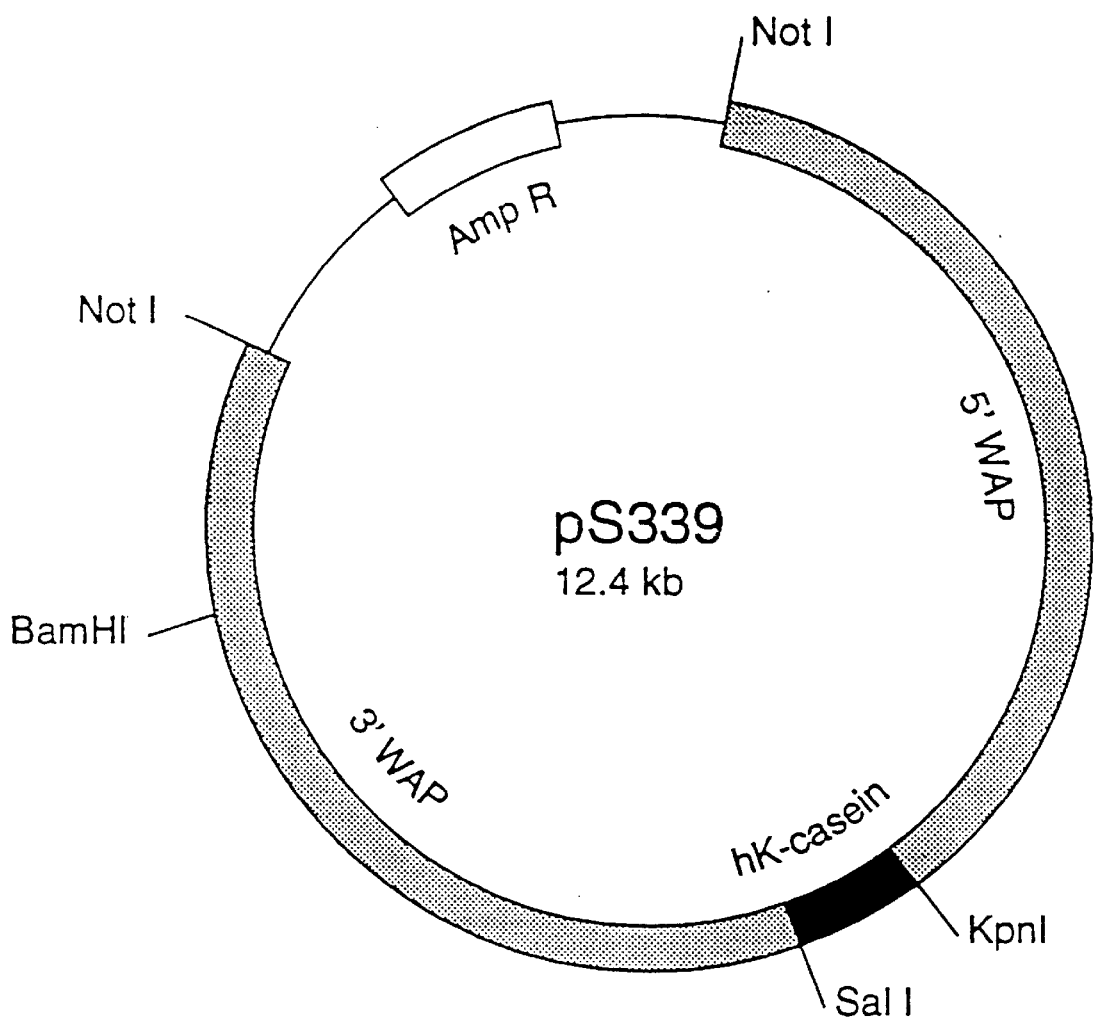

Lane 1 5 μg total RNA from pS306/C127 cells
Lane 2 5 μg total RNA from pS330/C127 cell line 9
Lane 3 5 μg total RNA from pS330/C127 cell line 14
Lane 4 5 μg total RNA from pS330/C127 cell line 20
Size markers are indicated to the left FIG. 12 shows a circular map of the expression vector pS339, constructed as described in Example 7. this expression vector mediates expression of recombinant human κ-casein in the mammary gland in transgenic animals.

Figure 13:
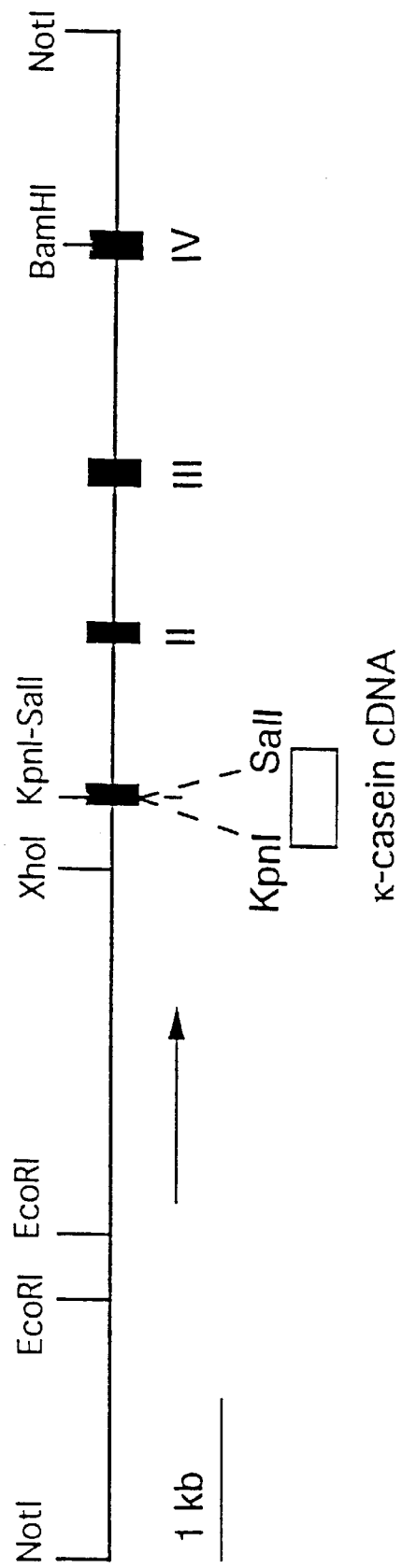

FIG. 13 shows the structure of the murine WAP/κ-casein recombinant gene in pS339. WAP exons are shown as solid boxes and numbered I–IV. The κ-casein cDNA is shown as an open box and the restriction sites used for insertion of the cDNA, KpnI and SalI, are shown. Restriction sites for orientation of the elements and for isolation of the recombinant gene are also indicated. The transcriptional direction of the recombinant gene is indicated by an arrow.

Figure 14:
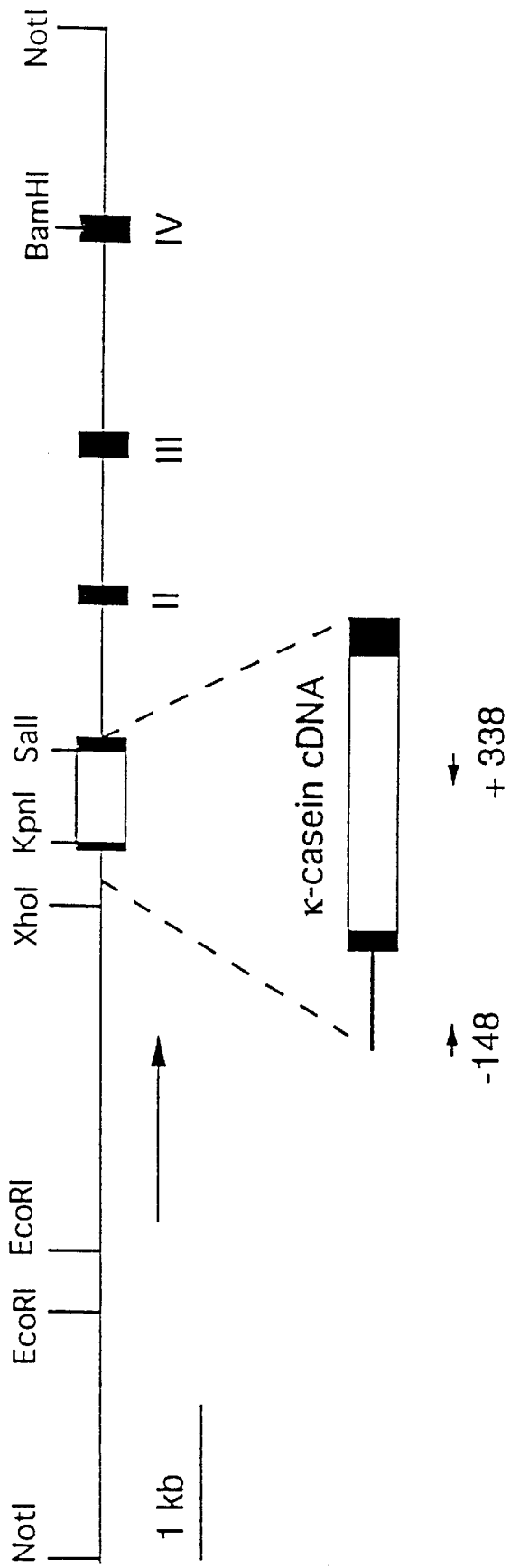

FIG. 14 is a schematic representation of the localization of the PCR primers used for identification of human κ-casein transgenic animals, as described in Example 7. The 5' primer is complementary to sequences within the murine WAP sequence starting at the position –148bp upstream of the fusion position between WAP and κ-casein cDNA. The 3' primer is complementary to κ-casein cDNA sequences ending 338 bp downstream of the fusion position.

Figure 15:

FIG. 15 is an agarose gel showing a PCR analysis of potential transgenic mice resulting from an experiment as described in Example 7. DNA was prepared from tail samples isolated from mice and used in PCR screening experiments with the primers described in Example 7 and FIG. 15. The resulting PCR amplified DNA samples were separated on 1% agarose gels and stained with ethidium-bromide M: molecular weight markers, sizes in kb are indicated to the left. Lane 1, positive control. PCR product generated from amplification using plasmid pS339 as template DNA. Lane 2, negative control, PCR analysis of DNA prepared from a non-transgenic mouse. Lanes 3–13. PCR screening of DNA samples prepared from different individual mice, representing potential transgenic founder animals. In lanes 7 and 13 a PCR generated band is clearly visible, demonstrating that biopsies used for DNA preparation were taken from transgenic animals in these samples. The expected size of the PCR amplified fragment, 486 bp, is indicated to the right.

Figure 16:
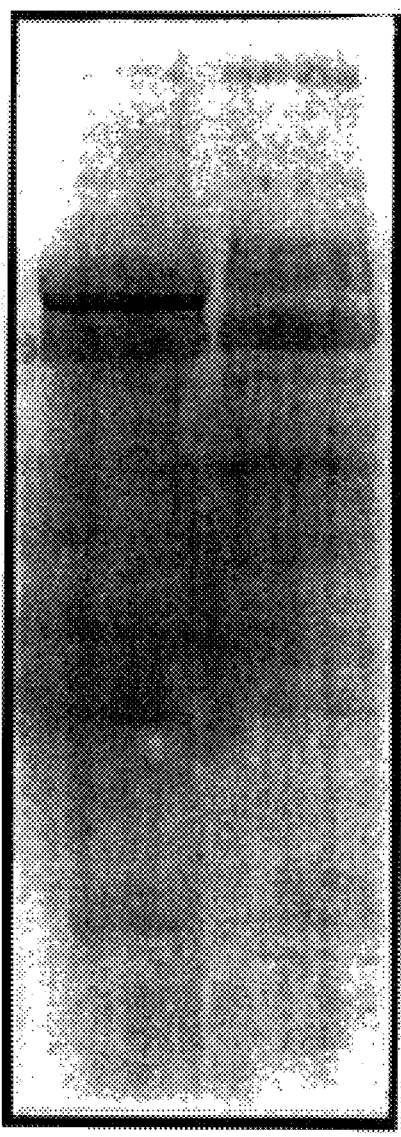

FIG. 16 shows the result of a Western blot analysis of milk samples derived from a non-transgenic mouse, and from a mouse transgenic for the recombinant WAP1 κ-casein gene of pS339, (line 11—11). The proteins are separated on SDS-PAGE and transferred to Immobilin membranes (Millipore), and visualised by alkaline phosphatase labelled polyclonal rabbit antibodies raised against highly purified human κ-casein (Examples 2).

Lane 1 2 μof milk derived from a pS339 transgenic mouse, line 11—11.

Lane 2 2 μof milk derived from a non-transgenic mouse.

Figure 17:
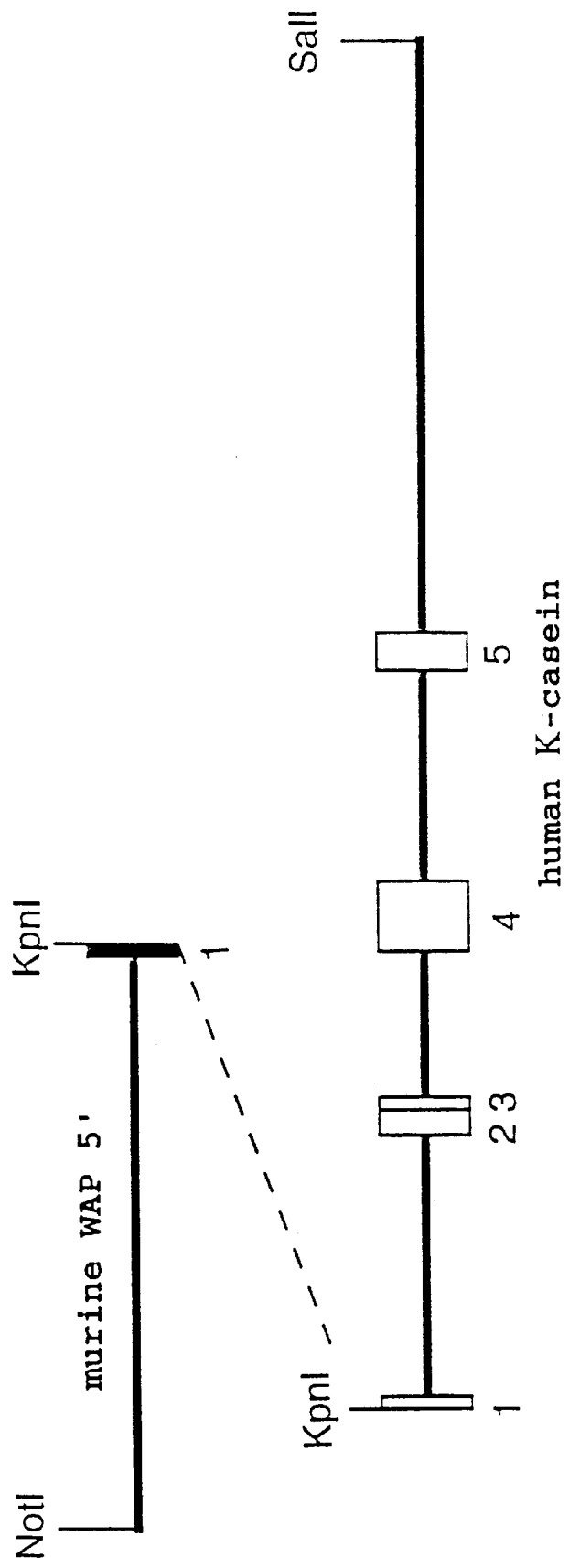

FIG. 17 shows the structure of the murine WAP/κ-casein recombinant minigene containing κ-casein intron sequences, as described in Example 7. WAP exon is shown as a solid box. κ-casein exons are shown as open boxes number 1–5. DNA fragments of human and murine origin are fused at indicated restriction sites.

Figure 18:
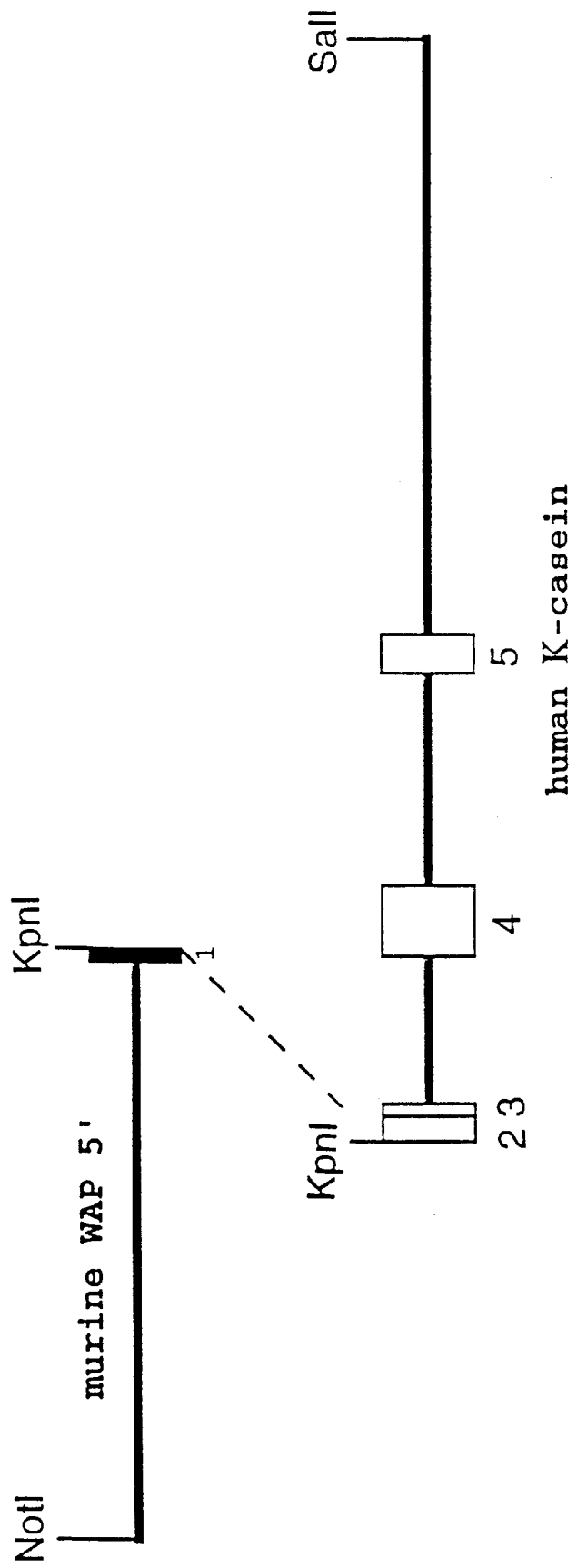

FIG. 18 shows the structure of the murine WAP/κ-casein recombinant minigene variant containing κ-casein intron sequences, as described in Example 7. WAP exon is shown as a solid box, κ-casein exons are shown as open boxes number 2–5. DNA fragments of human and murine origin are fused at indicated restriction sites.

REFERENCES

EPO Publication No. 0 247 494
EPO Publication No. 0 264 166 (Integrated Genetics, Inc.)
EPO Publication No. 0 279 582 (Bayer College of Medicine)
PCT Publication No. WO 82/04443 (Ohio University)
PCT Publication No. WO 88/00239 (Pharmaceutical Proteins Ltd.)
PCT Publication No. WO 88/01648 (Immunex Corporation
PCT Publication No. WO 91/03551 (Tsi-Mason Research Institute)
PCT Publicaiton No. WO 91/08216 (Genpharm International)
PCT Publication No. WO 92/03917 (Gen-Pharm International)
Alexander, L. J., Stewart, A. F. MacKinlay, A. G., Kapelinskaya, T. V., Tkach, T. M., Gorodetsky, S. I., Eur. J. Biochemistry, 178, 395–401, 1988.
American Academy of Pediatrics, Committee on Nutrition: Commentary on Breast-Feeding and Infant Formulas, including proposed standards for formulas, *Pediatrics* 57, 278–285 (1976).
American Academy of Pediatrics, Committee on Nutrition, *Pediatrics* 72, 359–363 (1983).
Anderson, S. A., Chinn, H. I., Fisher, K. D. History and current status of infant formula. Am. J. Clin. Nutr. 35, 381–397, 1982.
Aniansson, G., Anderson, B., Lindstedt, F. and Svanborg, C. Antiadhesive activity of human casein against Streptococcus pneumoniae and Haemophilus influenzae, Microbial Pathogenesis 8, 315–323, 1990.
Ausubel, F. M., Brent, R., Kingston, R. E., Moore, D. D., Seidman, J. G., Smith, J. A., Struhl, K. (eds.), Current Protocols in Molecular Biology, John Wiley & Sons, New York 1987.
Axelsson, I., Jakobsson, I., Lindberg T. and Benediktsson B. *Acta Pediatrica Scand.* 75, 702–707 (1986).
Azuma, N., Yamauchi, E., Mitsuoka, T. Bifidus growth-promoting activity of a glycomacropeptide derived from human κ-casein. Agric Biol. Chem. 48:2159–2162 (1984).
Betteridge, K. J. (1977) in: Embryo transfer in farm animals: a review of techniques and applications.
Bezkorovainy. A., Grohlich, J. D. Nichols, J. H. Isolation of a glycopeptide fraction with lactobacillus bifidus subspecies pennsylvanicus growth-promoting activity from whole human milk casein. Amer. J. Clin. Nutr. 32:14288–1432 (1979).

Bollag et al. (1989) *Ann. Rev. Genet.* 23, 199–225.

Bongso, T. A. & Basrur. P. K. (1975) *Vet. Rec.* 96, 124–126.

Brignon, G., Chtourou, A. and Ribadeau-Dumas, B. Preparation and amino acid sequence of human κ-casein, FEBS Lett. 188, 48–54, 1985.

Brinster, R. L. Allen, J. M., Behringer, R. R., Gelinas, R. E. and Palmiter, R. D. Introns increase transcriptional efficiency in transgenic mice. Proc. Natl. Acad. Sci USA 85, 836–840, 1988.

Camous et al. (1984) *J. Repod. Fert.* 72, 779–785 .

Campbell, S. M., Rosen, J. M., Henninghausen, L. G., Stretch-Jurk, U. and Sippel, A. E. Comparison of the whey acidic protein genes of the rat and mouse. Nucleic Acids Res. 12, 8685–8697, 1984.

Chiba, H., Tani, F. and Yoshikawa, M. Opioid antagonist peptides derived from κ-casein, J. Dairy Res. 56, 363–366, 1989.

Chobert, J. M., Mercier, J. C., Bahy, C. and Haze, G. FEBS Lett. 72, 173–178, 1976.

Clark, A. J., Simons, P., Wilmut, I. and Lathe, R. Pharmaceuticals from transgenic livestock, TIBTECH 5, 20–24, 1987.

Donahue, S. (1986) *Genetic Engineering of Animals*, ed. J. Warren Evans et al., Plenum.

EMBL DATABASE Jul. 23, 1996, Heidelberg, FRG: AC: M73628, Menon, R. S. et al, "Home sapiens kappa-casein mRNA, 3'end".

Eyestone, W. H. et al. (1989) *J. Reprod. Fert.* 85, 715–720.

Eyestone, W. H. (1989) "Factors affecting the development of early bovine embryos in vivo and in vitro." Ph.D. Thesis, University of Wisconsin.

Fiat, A. M. and Jolles, P. Caseins of various origins and biologically casein peptides and oligosaccharides: Structural and physiological aspects. Mol. Cell. Biochem 87, 5–30, 1989.

Fiat A. M. Jollès, J. Aubert, J. P., Loucheux-Lefebvre, M. H. and Jollès, P. Eur. J. Biochem 11, 333–339, 1980

Fitzgerald, R. J. and Swaisgood, H. E. Binding of ions and hydrophobic probes to alpha-lactalbumin and kappa-casein as determined by analytical affinity chromatography. Arch Biochem Biophys. 268, 239–48, 1989.

Furet, J. P., Mercier, J. C., Soulier, S., Gaye, P., Huedelahaie, D. and Vilotte, J. L. Nucleotide sequence of ovine κ-casein cDNA Nucleic Acids Res. 18, 5286, 1990.

Gandolfi et al. (1987) *J. Reprod. Fert* 81, 23–28.

Gordon et al. (1984), *Methods of Enzymology*, 101,414.

Graham, F. L., and Van der Eb. A. J., Virology 52, 456–467, 1973.

Hall, L., Emery, D. C., Davies, M. S., Parker, D. and Craig, R. K. Organisation and sequence of the human α-lactalbumin gene. Biochem. J. 242, 735–742, 1987.

Hambraeus, L., Forsum. E. and Lönnerdal, B. In: "Food and Immunology" pp. 116–124 (Eds. L. Hambraeus, L. A. Hanson and H. McFarlane) Almquist and Wiksell (1977).

Hammer et al. (1985), *Nature,* 315, 680.

Henninghausen, L. G., Ruiz, L. and Wall. R. Transgenic animals production of foreign proteins in milk. Curr. Opinions Biotechn. 1, 74–78, 1990.

Heyman, Y. et al. (1987) *Theriogenology* 27, 5968.

Higuchi, R. (1989) "Amplifications (a forum for PCR Users."2, 1–3.

Hogan B., Constantini, F. and Lacy, E. Manipulating and Mouse Embryo. A Laboratory Manual, Cold Spring Harbor Laboratory Press. 1986.

Jaenisch, R. (1976), *Proc. Natl. Acad. Sci. USA.* 73, 1260–1264.

Jolles, P., Parker, F., Floch, F., Migliore, S., Alliel, P., Zerial, A. and Weiner, G. H. Immunostimulating substances from human casein, J. Immunopharmacol, 3, 363–369, 1982.

Jolles P., Levy-Toledano, S., Fiat, A. M., Soria, C., Gillessen, D., Thomaidis, A., Dunn, F. W. Caen, J. P. Analog between fibrinogen and casein. Effect of an undecapeptide isolated from κ-casein on platelet function. Eur. J. Biochem. 158, 379–382, 1986.

King, D. et al, (1988) *Molecular Reproduction and Development* 1, 57–62.

Lönnerdal, B., Bergstrom. S. Andersson, Y., Hjalmarsson. K., Sundqvist, A. K., and Hernell, O. Cloning and sequencing of a cDNA encoding human milk β-casein. FEBS Lett. 269, 153–156, 1990.

Lusky, J., and Botchan, M. R., Cell 36, 391–401, 1984.

Marayama, S., Mitachi, H., Tanaka, H., Tomizuka, N., Suzuki, H. Studies on the active site and antihypertensive activity of angiotensin 1—converting enzyme inhibitors derived from casein. Agric. Biol. Chem. 51:1581–1586 (1987).

Menon, R. S. and Ham, R. G. Human β-casein: partial cDNA sequence and apparent polymorphism. Nucleic Acids Res. 17, 2869, 1989.

Miller. M. J. S., Witherly, S. A. and Clark, D. A. Casein: a milk protein with diverse biologic consequences, Proc. Soc. Exp. Biol. Med. 195, 143–159, 1990.

Mount, S. M. A catalogue of splice junction sequences. Nucleic Acid Research 10, 459–472, 1982.

Newport. M. J. and Henschel, M. J. *Pediatric Res.* 18, 658–662 (1984).

Nilsson, J., Blackberg, L., Carlsson, P., Enerback, S., Hernell, O. and Bjursell, G. cDNA cloning of human-milk bile-salt-stimulated lipase and evidence for its identity to pancreatic carboxylic ester hydrolase. Eur. J. Biochem. 192, 543–550, 1990.

Packard, V. S. "Human Milk and Infant Formula", pp. 147–154. Academic Press (1982).

Parrish et al. (1986) *Theriogenology* 25, 591–600.

Parrish et al. (1988) *Biol. Reprod.* 38, 1171–1180.

Pavlakis, G. N., and Hamer, D. H., Proc. Natl. Acad. Sci. USA 80, 397–401, 1983.

Picken, R. N., Mazaitis, A. J., Maas. W. K., Rey, M. and Heyneker, H. Nucleotide sequence of the gene for heat-stable enterotoxin II of *E. coli*, Infect. Immun. 42, 269–275, 1983.

Pratner et al. (1987) *Biol. Reprod.* 37, 859–866.

Rexroad et al. (1988) *J. Anim. Sci.* 66, 947 –953.

Roble et al. (1987) *J. Anim. Sci.* 64, 642–664.

Rowland, S. J. J. Dairy Res. 9, 47–57, 1938.

Rubnitz, J. and Subramani, S. (1984) *Mol. Cell. Biol.* 4, 2253–2258.

Rumsey et al. (1974) *J. Anim. Sci.* 39, 386–391.

Sambrook, J., Fritsch, E. F. and Maniatis, T. E. Molecular cloning, a laboratory manual, 2nd ed. Cold Spring Harbor Laboratory Press, 1989.

Sarver, N., Byrne, J. C., and Howell, P. M., Proc. Natl. Acad. Sci. USA 79, 7147–7151, 1982.

Sirard et al. (1988) *Biol. Reprod.* 39, 546–552.

Stan, E. Y., Chernikov, M. P. Formation of a peptide inhibitor of gastric secretion from rat milk proteins in vivo. Bull Exp. Biol. Med., 94:1087–89 (1982).

Studier, F. W., Rosenberg, A. H., Dunn, J. J. and Dubendorff, J. W. Use of T7RNA Polymerase to direct expression of cloned genes. In Methods in Enzymology, ed. David V. Goeddel, p. 60–89. Academic Press, 1990.

Wall et al. (1985) *Biol. Reprod.* 32, 645–651.

Williams et al. (1984) *Theriogenology* 22, 521–531.

Yvon, M., Pelissier, J. P., Characterization and kinetics of evacuation of peptides resulting from casein hydrolysis in the stomach of the calf. J. Agric. and Food Chem. 35:148–158 (1987).

EXAMPLES

The following examples are intended to illustrate but not to limit the present invention.

Construction of the expression systems of the invention, and the molecular biological characterization of it, employs standard methods generally known in the art of recombinant DNA. Unless otherwise stated, the methods used are those described by Sambrook et al., 1989; Ausubel et al. 1991.

DEFINITIONS

Hybridization of DNA

DNA, e.g. present on nitrocellulose filters, are wetted in 2×SSC [1×SSC: 0.15 M NaCl, 0.0015 M $Na_3$-citrate, pH 7.0]and placed in a heat-sealed plastic bag with pre-warmed (67° C.) prehybridization solution. Prehybridization takes place for 2 h at 67° C., the bag being gently shaken. The solution is exchanged with pre-warmed (67° C.) hybridization solution, a radioactive probe is added and hybridization is carried out at 67° C. for 18 h. The bag is gently shaken to ensure constant movement of the liquid over the nitrocellulose filters. After hybridization, a washing procedure is carried out.

The radioactive probe is prepared by use of known methods, e.g. as described by Sambrook et al., on the basis of the DNA sequence shown in SEQ ID NO:1 or a part thereof, especially a coding part such as the nucleotides corresponding to amino acids 1–210 or an effective subsequence of the DNA sequence as defined above.

The prehybridization and hybridization solutions used are: 10×Denhardt's, 4×SSC, 0.1% SDS, 10 μg/ml polyA, 50 μg/ml of denatured DNA to be analysed and the denatured (heat) radioactive probe. The filters are washed in pre-warmed (67° C.) solutions: 10×Denhardt, 2×SSC, 0.1% SDS for 2×15 min. and 1×SSC, 0.1% SDS for 4×15 min. The filters are air dried and covered with Vita-Warp, and X-ray film is exposed to the filters for 3 h to 3 weeks with and without intensifying screens.

EXAMPLE 1

Purification of native κ-casein from human milk

Human milk was centrifuged at 15,000×g for 45 min and the flotated fat layer was removed. The skimmed milk was acidified with HCl to pH 4.3 and incubated under stirring for 1 h at room temperature and thereafter centrifuged and 90 min at 18,000×g. The resulting pellet (the casein fraction) was dissolved in and dialyzed against 20 mM ethanolamine, 6 M urea, pH 9.5 and thereafter extracted several times by shaking with hexane. After extraction, the water phase was dialyzed against water and lyophilized.

The lyophilized casein fraction was dissolved in 50 mM imidazol-HCl pH 7.0, 0.5% SDS, 0.5% 2-mercaptoethanol, incubated at 37° C. for 1 h, and applied to a Sephadex G-200 column, 1.6×120 cm, equilibrated with the same buffer except that the 2-mercaptoethanol was 0.01%. The chromatography was performed at 37° C. to avoid complex formation which occurred at 4° C. as well as at room temperature. Fractions eluting where κ-casein was expected to elute were analyzed for carbohydrate content and the factions containing carbohydrate were pooled for further purification. The main impurity in this fraction was βcasein, which constituted about 90% of the protein in pool. The pool was first dialyzed against 40% methanol and thereafter against 20 mM potassium phosphate buffer pH 6.8, 0.1% Tween 20, 0.01% 2-mercaptoethanol.

To remove κ-casein from this impurity, the pool was run on a hydroxyapatit column, 1×6.5 cm, equilibrated with the same buffer as the pool was dialyzed against, and eluted with a gradient from 0.02–0.4 M potassium phosphate. Also in this case the chromatography had to be performed at 37° C. to avoid complex formation. Most of the κ-casein was not bound to the column while β-casein was close to completely bound. The unbound material was pooled, dialyzed against water and lyophilized, κ-casein was analyzed on SDS-PAGE and found as a diffuse faint band at 35–40 kDal, but stained weakly with Coomassie Brilliant Blue.

The identity of the protein was assayed by amino acid analysis where the high isoleucine/leucine ratio is one of the most characteristic properties of the protein. The protein also stained with Schiffs reagent as expected for such a highly glycosylated protein.

EXAMPLE 2

Production and purification of polyclonal antibodies reactive against κ-casein

The κ-casein purified as described in Example 1 was used for immunization of rabbits. When antiserum reactive against κ-casein was obtained, it crossreacted with both whey proteins and β-casein, as well as with *E. Coli* proteins when used for protein blotting. A number of methods was therefore used to increase the specificity of the antiserum.

First, the antiserum was incubated with a *E. coli* cell lysate to adsorb and precipitate the unspecific antibodies reacting with *E. coli* proteins. The antiserum was centrifuged (5000×g, 15 min) after one hour incubation and the pellet was discarded. To purify the antiserum further, highly purified recombinant β-casein was immobilized on to CNBr-activated Sepharose and the antiserum was secondly run through this column several times to adsorb antibodies reactive against β-casein. Thirdly, native κ-casein prepared from human milk as described in Example 1 was immobilized on to CNBr-activated Sepharose and the antiserum was purified on this gel by affinity chromatography. Fourthly, the antiserum was precipitated with whey proteins prepared from human milk. Antiserum purified by all these steps still crossreacted somewhat with other milk proteins upon analysis by protein blotting but reacted much more strongly with κ-casein when a milk protein sample was separated by electrophoresis, electroblotted and stained using this antiserum.

The crossreactivity can be explained by the fact that it is very difficult to prepare pure β-casein and pure κ-casein from human milk. In addition, the caseins are always present i the whey faction to a small extent in the same manner as the whey proteins are present in the casein fraction. This leads to a situation where it is very difficult to obtain completely pure protein for immunization and it also difficult to prepare casein columns that are completely free from other milk proteins. Therefore, the obtained antisera are at the end enriched in specific antibodies rather than highly purified, although a large number of purification methods have been used.

EXAMPLE 3

Cloning and sequencing of cDNA encoding human κ-casein

Construction of the expression systems of the invention, and the molecular biological characterization of it, employs standard methods generally known in the art of recombinant DNA. Unless otherwise stated, the methods used are those described by Sambrook et al., 1989.

A λ-gt 11 human mammary gland cDNA library generated from mRNA prepared from a tissue biopsy isolated from a human mammary gland was prepared. The donor of the biopsy was a lactating woman. The library was screened by immunological methods using the κ-casein polyclonal antibodies prepared according to Example 2.

Buffers used were: TBS (50 mM Tris-HCl pH 7.9, 150 mM NaCl), TTBS (TBS containing 0.05% Tween 20).

The procedure used was as follows: E. coli Y1090 bacteria were grown on LA plates containing 50 μg/ml of carbenicillin. A single colony was isolated and grown over night in a LB containing 0.2% maltose and 10 mM MgSO$_4$. 0.4 ml of the culture was then mixed with diluted library phages and adsorption was allowed for 15 min at 37° C. The infected culture was mixed with 7 ml soft agarose (0.75% agarose in LB and 10 mM MgSO$_4$). The soft agarose mixture was poured on 150 mm LA plates. The plates were incubated at 42° C. for about 3.5 h. until plaques were visible. Thereafter, each plate was overlayed with a membrane (DuPont NEN, Colony Plaque Screen) previously saturated in 10 mM IPTG (Isopropyl-β-D-thiogalactoside), and incubated over night at 37° C. The positions of the membranes were indicated before the membranes were removed. The membranes were then washed in TTBS, and incubated in TTBS containing 20% FCS and the polyclonal κ-casein antisera diluted 1:25 for 2 h at room temperature. The membranes were washed two times for 5 minutes in TTBS at room temperature. Biotinylated goat-antirabbit IgG in TBS was added and the membranes incubated for 1 h at room temperature. The membranes were then washed again with TTBS two times for 5 min at room temperature. The conjugate of streptavidin and biotinylated alkaline phosphatase in TTBS was added followed by an incubation for 1 h at room temperature. The next step was to wash the membranes four times in TTBS for 5 min and to rinse them three times in a buffer containing 50 mM Tris-HCl pH 9.8, 3 mM MgCl$_2$, 50 μg/ml XP (5-bromo-4-chloro-3-indolylphosphate (Nasalt) and 100 μg/ml NBT (Nitroblue tetrasolium grade III). Approximately 100 positive plaques were identified by reaction with antibodies produced as described in Example 2.

The isolated plaques were purified by dilution and repeated screening. Phage DNA was prepared according to Sambrook et al. 1989 and the DNA preparations were digested with EcoRI. The digested DNA was separated by agarose electrophoresis and a number of EcoRI fragments were cloned into EcoRI digested and alkaline phosphatase treated pUC 18 plasmids and subsequently transformed into E. coli TG2. Transformants were selected on plates containing 50 μg/ml of carbenicillin. 40 μg/ml of X-gal (5-bromo-4-chloro-3-indolyl-β-D-galactoside) and 1 mM IPTG (Isopropyl-β-D-thiogalactoside). Plasmid DNA was analysed from a number of transformants. One of these transformants was found to harbour a plasmid containing the full length cDNA fragment encoding human κ-casein. This plasmid was designated pS 270, FIG. 1. Plasmid pS 270 DNA was subjected to restriction endonuclease analysis. The complete nucleotide sequence of both strands of the region encoding κ-casein was determined, using a T7 sequencing kit (Pharmacia, Uppsala, Sweden), on double stranded templates as described by the vendor. As primers for sequencing reactions, specific oligonucleotides complementary to pUC 18 or κ-casein sequences were used.

The nucleotide sequence (SEQ ID NO:1) contained an open reading frame sufficient to encode the entire amino acid sequence of a κ-casein precursor protein consisting of 162 amino acids and a signal peptide of 20 amino acids (SEQ ID NO:2).

EXAMPLE 4

Cloning, sequencing and organization of human κ-casein genomic fragments

To determine the structural organization and sequence of the human κ-casein gene, human genomic DNA libraries and human genomic DNA were screened and analyzed. Human genomic libraries were obtained from Clontech (Palo Alto, USA). The libraries were constructed from placenta DNA (catalog #HL1067J) or female leukocyte DNA (catalog #HL1111J), cloned into λEMBL-3 vector. The average size of inserts are 15 kb or 16 kb and the number of independent clones are $2.5 \times 10^6$ or $1.7 \times 10^6$, respectively. Human genomic DNA preparations were extracted from human tissue samples or from human cell lines. Human genomic DNA was also obtained from Clontech (catalog #6550-2). In order to isolate recombinant phages containing exon and intron sequences of the human κ-casein gene, 195 individual bacterial plates with a diameter of 150 mm and approximately $10^4$ individual plaques per plate, were screened. The methods and solutions used were as described in the Library Protocol Handbook: General Procedures for the Hybridization of Lambda Phage Libraries w/DNA Probes (Clontech) with some modifications as will be apparent from the following.

The experiment was carried out essentially as follows. The numbers will be given per plate basis. A sample of the phage library diluted in 0.1 ml sterile lambda diluent was prepared in order to obtain an estimated titer of 10,000pfu (plaque forming units). A 0.6 ml LD-medium culture of the E. coli host strain NM 539 (obtained from Clontech) was infected with 10000 pfu recombinant phages and 0.3 M SM buffer was added. The infected culture was incubated for 20 minutes at 37° C.

The culture was then mixed with top agarose (7.2 g of agarose added per litre LB) and poured onto LB plates. The plates were incubated at 37° C. for approximately 7 hours. The plates were then chilled at 4° C.

Plaque hybridization experiments wee as follows. Membrane filters, Colony/Plaque Screen (DuPont, USA), were placed onto the top of the plates for 2–3 minutes. The filters were removed and floated in 0.5 M NaOH on a plastic wrap for 2 minutes, with the plaque side up, for denaturation of DNA. This step was repeated once to ensure efficient denaturation. The membrane filters were then transferred to a neutralizing solution, 1M Tris-HCl pH 7.5, for 2 minutes for two times to ensure efficient neutralization. The filter membranes were then allowed to dry.

To obtain a probe for DNA hybridization screening of the membrane filters, pS270 was digested with EcoRI and a 857 bp fragment was separated by agarose electrophoresis, excised and transferred to a polypropylene microcentrifuge tube. The isolated cDNA fragment was $^{32}$P-labelled using multiprime DNA labelling system (Amersham) by the following procedure. Water was added at a ratio of 3 ml per gram of gel, and placed in a boiling water bath for 7 minutes to melt the gel and denature the DNA. The tube was then transferred to a water bath at 37° C. for at least 10 minutes. A volume of DNA/agarose solution containing 0.25 ng of DNA was added to the labelling reaction, according to the supplier's instructions.

The hybridization method was under stringent conditions at 65° C. according to the method described below. The filter membranes were prehybridized by treating in a solution of 1% SDS, 1M NaCl, 10% dextran sulfate in a bottle using a hybridization over (Hybaid) at 65° C. for at least 1 hour. Following prehybridization a solution containing denatured herring sperm DNA of a final concentration of 100 mg/ml and the $^{32}$P-labelled DNA probe at a concentration <10 ng/ml (for optimal signal to background ratio) was added to the prehybridization solution and the membrane filters were incubated at 65° C. for 10–20 hours. To wash the membrane filters the hybridization solution was removed. In the first step the membrane filters were washed in a 2×SSC (0.3M NaCl, 0.03M Na-citrate), 1% SDS solution two times for 5 minutes at room temperature. In the next step the membrane filters were incubated in the same solution for two times at 65° C. for 30 minutes. In a third step, the filters were washed two times at room temperature in 0.1×SSC. Finally, the membrane filters were then placed on a sheet of filter paper with the DNA face up, and allowed to dry. The dried membrane filters were then exposed to X-ray films and autoradiographed.

Of the approximately 2×10$^6$ individual plaques analyzed as described, three hybridizing plaques were detected and isolated. These three isolates were designated #2, 41 and 42, respectively. After several rescreening experiments, the recombinant phage DNA was purified according to Sambrook et al, 1989. The purified DNA was digested with SalI and the fragments representing the inserts were isolated by agarose electrophoresis.

The sizes of the inserts were approximately 18 kb, isolate #2; 15 kb, isolate #41; and 17 kb, isolate #42. These fragments were cloned into SalI digested linearized pUC19, resulting in pS457 (isolate #2), pS458 (isolate #41), pS459 (isolate #42) (FIG. 2). The inserts from the three plaques which hybridizes to the κ-casein cDNA probe from pS270, were analyzed by PCR, restriction mapping and hybridization to $^{32}$P-labelled oligonucleotides representing various regions of the κ-casein gene. The fragments were also hybridized against each other. The insert from isolate #42 was shown to contain a large portion of the κ-casein gene, although not the entire transcribed region. The cloned fragment in isolate #2 was found to show partial homology with isolate #42. However, a number of discrepancies between the two isolates were observed. It was demonstrated by comparison to human genomic DNA using PCR analysis that isolate #2 contains partially rearranged regions. The insert in isolate #41 was shown to contain homologies with the 3' end of the cDNA, and the insert was shown to extend further downstream of the transcribed part of the κ-casein gene. Thus, for the analysis and characterization of κ-casein exon and intron sequences and organization the insert from isolate #42 was selected.

The cloned fragment in pS459 (FIG. 2) was characterized by restriction enzyme mapping, using EcoRI, HindIII, XbaI, AccI, PstI, KpnI, and SacI. The resulting restriction map is shown in FIG. 5. The approximate positions of the exons and the approximate size of the introns were analyzed by PCR and electrophoresis. The results generated from the pS459 clone were compared to results obtained with the same PCR primers using human DNA as template. The generated results from the two templates were identical.

In order to facilitate nucleotide sequence analysis, 18 restriction fragments derived from pS459 were isolated and subcloned into pUC19, resulting in pS461–478 (FIG. 5). The orientation of the subcloned fragments were determined by PCR analysis. The following strategy was employed; by combining PCR primers located within the pUC19 sequence at each side of the cloning site, separately, and the other PCR primer with defined orientation and specific for the κ-casein derived subcloned fragment allowed the determination.

The inserts in the 18 plasmids pS461–478 were subjected to nucleotide sequence analysis. The complete nucleotide sequences for all subclones were determined using a T7 sequencing kit (Pharmacia, Sweden: United States Biochemical, USA) on double stranded templates as described by the vendors. As primers for sequencing reactions specific oligonucleotides complementary to pUC19 (E20 5'-GTTGGGTAACGCCAGGGTTTTC-3' (SEQ ID NO: 5), SYM 1121 5'-CAGGAAACAGCTATGAC-3' (SEQ. ID NO: 6), SYM 2589 5'-TTCCGGCTCGTATGTTGTGTGG-3' (SEQ ID NO:7)) or primers complementary to κ- casein (see Table 1) were used.

TABLE 1

Primers used for sequencing of the human κ-casein gene

| Primer | Location | Sequence | Direction | SEQ ID NO: | Nucleotides |
|---|---|---|---|---|---|
| SYM 2271 | Exon 4 | AACCAACACCAGCTCCTGCC | 5'-3' | 4 | 10349-10360 |
| SYM 2272 | Exon 5 | AAGGAGAGTGTGAAGTAGTA | 3'-5' | 4 | 12315-12296 |
| SYM 2430 | Exon 4 | ACATAATACATTGGGACATA | 3'-5' | 4 | 10079-10060 |
| SYM 2445 | Exon 4 | CCGCTGAGGAATTTGGGCAT | 3'-5' | 4 | 10215-10196 |
| SYM 2446 | Exon 4 | TATCAGAAAACAGCTCCATA | 5'-3' | 4 | 10042-10061 |
| SYM 2448 | Exon 5 | ACCAAATTACTACTTCACAC | 5'-3' | 4 | 12288-12308 |
| SYM 2449 | Exon 4 | TTCAGTGGCAGGAGCTGGTG | 3'-5' | 4 | 10374-10355 |
| SYM 2767 | Exon 4 | ACACCAAGGAAATATCAAAG | 5'-3' | 4 | 10479-10498 |

TABLE 1-continued

Primers used for sequencing of the human κ-casein gene

| Primer | Location | Sequence | Direction | SEQ ID NO: | Nucleotides |
|---|---|---|---|---|---|
| SYM 2768 | Exon 5 | GCAATCAGTTGGCTTTATTG | 3'-5' | 4 | 12442-12423 |
| SYM 2921 | Exon 2 | AGGCAGGGTTAATGCCAGGG | 3'-5' | 4 | 2241-2223 |
| SYM 2922 | Exon 3 | TGCTGGTTGTTTCTGGTTT | 3'-5' | 4 | 8849-8867 |
| SYM 3255 | Exon 3 | CTGTGGAGGTTCAAAACC | 5'-3' | 4 | 8836-8853 |
| SYM 3272 | Exon 1 | CTTTCCTCGTGCCAGTCAGGTC | 3'-5' | 3 | 45-24 |
| SYM 3273 | Exon 2 | CAATAATGAAGAGTTTTCTTC | 5'-3' | 3 | 2190-2210 |
| SYM 3410 | Intron 4 | GCCATTATCCATTGGTCCAAG | 3'-5' | 4 | 11182-11162 |
| SYM 3411 | Intron 4 | CATAATTCTGGTTGCTATAAGAC | 5'-3' | 4 | 10477-10499 |
| SYM 3412 | Intron 3 | GAAGTATGGAACCCAGCAG | 3'-5' | 4 | 9884-9902 |
| SYM 3415 | Intron 3 | CAAAAGATTAGATAAAGAATTGTC | 3'-5' | 4 | 9434-9411 |
| SYM 3416 | Intron 4 | GACAAAGTGAAAATAATTGG | 5'-3' | 4 | 10717-10736 |
| SYM 3431 | Intron 4 | GTAGTCCCATGATATCACAG | 3'-5' | 4 | 11391-11372 |
| SYM 3445 | Intron 4 | CAAATGGGAGGCAAACCAAAC | 5'-3' | 4 | 11748-11768 |
| SYM 3470 | Intron 3 | GGTTTTAGACAGAAGGCATC | 3'-5' | 4 | 8961-8942 |
| SYM 3531 | Intron 2 | CTTAGCACAGACTCTGGCAC | 3'-5' | 4 | 4392-4373 |
| SYM 3532 | Intron 2 | GGATAGGATATTAGTAGAG | 5'-3' | 4 | 4776-4794 |
| SYM 3533 | Intron 2 | GTAAGCATAATTCATAGCATAG | 5'-3' | 4 | 880-901 |
| SYM 3534 | Intron 2 | ATACTTGTTGAGTGAATGAC | 3'-5' | 4 | 5788-5769 |
| SYM 3535 | Intron 2 | CAGTCAGTAGTTCCCAACC | 5'-3' | 4 | 6004-6022 |
| SYM 3536 | Intron 2 | GAAGCAACAGTAGTCTAACTG | 3'-5' | 4 | 8670-8650 |
| SYM 3537 | Intron 2 | CAAGCCACACGAAGGCCCAAC | 5'-3' | 4 | 6209-6229 |
| SYM 3538 | Intron 2 | CAACTCTCCTGCCTCAGCC | 5'-3' | 4 | 200-239 |
| SYM 3539 | Intron 2 | CACCACACTTTTATGAACTGC | 3'-5' | 4 | 3081-3061 |
| SYM 3540 | Intron 2 | GAATGATTATTAAGATCAGTAG | 3'-5' | 4 | 680-662 |
| SYM 3541 | Intron 2 | GAGGTGCTGAAAGATTAAGTG | 5'-3' | 4 | 4528-4548 |
| SYM 3546 | Intron 2 | CCTCCCATTTGTCACTATCC | 3'-5' | 4 | 75-56 |
| SYM 3547 | Exon 1 | CAGCTCAACCTACTGCCAAC | 5'-3' | 3 | 1-20 |
| SYM 3548 | Intron 2 | CTTCTTCATGGAAGTACTCC | 3'-5' | 4 | 2830-2811 |
| SYM 3549 | Intron 2 | GAGCAGGCCGGACGATGTG | 3'-5' | 4 | 403-384 |
| SYM 3555 | Intron 2 | GATTACAGGTGTGAGCACAG | 3'-5' | 4 | 4094-4075 |
| SYM 3556 | Intron 2 | CAGTTACTAACGTCTGTGATAC | 5'-3' | 4 | 1469-1490 |
| SYM 3557 | Intron 2 | CAACAGAGGTGAGTGCCGC | 3'-5' | 4 | 2249-2231 |
| SYM 3558 | Intron 2 | GATTACAGGGTGAGACATGTG | 5'-3' | 4 | 7959-7979 |
| SYM 3567 | Intron 2 | CTGCACAAAATAAGTGTACAC | 3'-5' | 4 | 1322-1302 |
| SYM 3568 | Intron 2 | CCTCTGGATTAACATTGTTC | 5'-3' | 4 | 2351-2370 |
| SYM 3569 | Intron 2 | GTTTGAACTCTCACCACTC | 5'-3' | 4 | 3431-3450 |
| SYM 3570 | Intron 2 | GCTTCATGCCTGTGGTCCATG | 5'-3' | 4 | 5037-5057 |
| SYM 3571 | Intron 2 | CTCATCAATGGCCAGATCTTC | 3'-5' | 4 | 5565-5545 |
| SYM 3572 | Intron 2 | GAAGATAGATGTTGGGAAG | 5'-3' | 4 | 6451-6469 |
| SYM 3573 | Intron 2 | TCTCACTTTGATTGTATGTGGT | 3'-5' | 4 | 7577-7557 |
| SYM 3574 | Intron 2 | TAAGAATGAAAGAGGGGGTCG | 5'-3' | 4 | 6910-6930 |
| SYM 3575 | Intron 2 | GTAGATGATGAGGTGATGAGG | 3'-5' | 4 | 7798-7778 |
| SYM 3577 | Intron 2 | GTCTGACTGGAAGGGACCAG | 5'-3' | 4 | 1638-1657 |
| SYM 3578 | Intron 2 | GCAACACCTAAGCCATACTGTG | 3'-5' | 4 | 2019-1998 |
| SYM 3587 | Intron 2 | CATGAACTGAATGCAATCTC | 3'-5' | 4 | 3879-3860 |
| SYM 3588 | Intron 2 | GCTCTCATCTTGTATCTCAG | 3'-5' | 4 | 7281-7262 |
| SYM 3604 | Intron 1 | GGTAGATTTAGCCGATGTG | 3'-5' | 3 | 2078-2060 |
| SYM 3605 | Intron 2 | GCCTCAGCCTCCCGAGTAG | 3'-5' | 4 | 7115-7097 |
| SYM 3608 | Intron 1 | GTTCATGGCGATTCTCAAG | 5'-3' | 3 | 1675-1693 |
| SYM 3609 | Intron 1 | GATGACATCGTATGGGCAG | 5'-3' | 3 | 837-855 |
| SYM 3610 | Intron 1 | CTCCTTATTAATGCTTCAC | 3'-5' | 3 | 757-739 |
| SYM 3612 | Intron 1 | GTAGGATGGAATGGGAAGTG | 3'-5' | 3 | 1342-1323 |

The genomic fragment cloned in pS459 contains a large portion of the transcribed part of the human κ-casein gene. The complete sequence of all exons and introns cloned in pS459 is listed in SEQ ID NO:4. the cloned sequence extends from the second intron to sequences downstream of the last exon, containing 11748 bp of intron sequences.

To obtain information about the length and sequence of the first intron of the human κ-casein gene, a PCR experiment was designed. By comparison of the human κ-casein cDNA sequence to the published bovine κ-casein cDNA and genomic DNA sequence and organization, putative exon/intron boundaries were postulated for the human κ-casein gene. A set of oligonucleotides to be used as PCR primers (SYM 3579 5'-ATCCCGGGCAGGGTTAATTGCCAGGGC-3' (SEQ ID NO:8), SYM 3580 5'-CGAAGCTTCAGCTCAACCTACTGCCAAC-3'(SEQ ID NO:9), complementary to sequences on either side of the postulated border between exon 1 and 2, were designed and synthesized. The results obtained in PCR experiment with these primers indicated that the size of the first intron is about 2.1 kb, PCR fragments generated using SYM 3579 and SYM 3580, representing intron 1 and partial sequence of exon 1 and 2 were cloned into XmaI and HindIII digested pUC19 for analysis. A detailed restriction map was obtained for the cloned fragments using EcoRI, HindIII, XbaI, AccI, PstI, KpnI and SacI (FIG. 4). To exclude the potential risk of PCR generated mutations independent transformants were analyzed, and PCR generated fragments using different template DNA have been analyzed. In order to facilitate sequence analysis 6 restriction fragments representing intron 1 sequences were isolated restriction fragments representing intron 1 sequences were isolated and subcloned into pUC 19, pS479–484 (FIG. 6). The complete sequence of intron 1 of the human κ-casein gene was obtained by methods as described above. A pUC 19 plasmid containing this PCR fragment with the sequence shown in SEQ ID NO:3 (comprising exon 1 and part of exon 2 as well as intron 1) was identified and designated pS 460 (FIG. 3).

The human κ-casein gene consists of 5 exons and four introns (FIG. 4). The translational start is localized in exon 2 and the translational stop is localized in exon 4. The exons are relatively small, the size range is between 33 bp and 469 bp. The structure and organization of the human exons are very similar to that of the bovine κ-casein gene (Alexander et al., 1988). The main structural difference between the human and bovine κ- casein genes is that the second intron of the human gene is much longer than the bovine counterpart.

As can be noted from table 2 exon/intron boundaries are in accordance with the AG/GT rule and conform well to the consensus sequence suggested by Mount et al. 1982.

TABLE 2

Exon-Intron boundaries of the κ-casein gene sequences at exon-intron junctions

| | 5' splice donor | 3' splice acceptor |
|---|---|---|
| Exon1-Exon2 | CGAGGAAAG gtaatg . . . | ctttag GTGCAATAA |
| Exon2-Exon3 | CCTTTTTTG . . . | . . . ccccag GCTGTGGAG |
| Exon3-Exon4 | CAACCAGCA gtaagt . . . | ttatag TGCCATGAG |
| Exon4-Exon5 | TGTTGCGTC gtaaat . . . | ttatag GACTTGCTG |

A comparison of the deduced amino acid sequences derived from the cDNA sequence (SEQ ID NO:1) and the genomic DNA sequence (SEQ ID NO: 4) reveals that the codon for the amino acid in position 110 (SEQ ID NO:2) was changed from encoding arginine (cDNA) to leucine (genomic DNA, SEQ ID NO:4 nucleotides 10255–10257). This observation probably reflects the normal occurrence of genetic variants.

EXAMPLE 5

Expression of recombinant human κ-casein in bacterial systems

In order to produce recombinant human κ-casein in *E. coli*, the κ-casein encoding sequence was introduced into two different vectors. One vector contains a signal sequence in front of the κ-casein encoding sequence whereas the other lacks such a signal sequence.

The cDNA encoding the pro-polypeptide for human κ-casein was isolated and cloned into pUC19, generating pS270, as described above (Example 3). The cDNA was later introduced into an expression vector, pS339, which was designed for stage- and tissue-specific expression of recombinant human κ-casein in transgenic animals, as described below (Example 7).

To facilitate introduction into the expression vectors, a κ-casein cDNA fragment containing a SalI restriction site just downstream of the translational stop codon was isolated from pS339 plasmid. The unique SphI site located downstream of the signal sequence was used to get a convenient site in the 5'-end. The SphI and SalI digested restriction fragment of about 469 bp derived from pS339 was isolated by agarose electrophoresis. This fragment was cloned into SphI and SalI digested pUC18, resulting in plasmid pS428.

To generate an expression vector encoding mature κ-casein without a signal peptide, the following three fragments were ligated. First, the major part of the κ-casein cDNA was isolated as a 481 bp fragment from pS428 by SphI and BamHI digestion. Second, synthetic oligonucleotides were designed to generate a NdeI restriction site in front of the κ-casein encoding sequence in combination with a translational start codon. Furthermore, the synthetic oligonucleotides contain the sequence encoding the eight κ-casein amino acids which are missing in the pS339 fragment. These amino acids are the original amino terminal of human mature κ-casein. The sequences of the two synthetic oligonucleotides are, SYM 3047 5'-CTGGTTGTTTCTGGTTTTGAACCTCCA-3' (SEQ ID NO: 10). and SYM 3048 5'-TATGGAGGTTCAAAACCAGAAACAACCAGCATG-3' (SEQ ID NO: 11).

Third, to provide regulatory elements, replication signals and selection markers, the plasmid pS26 was digested with NdeI and BamHI. The vector pS 26 carries the bacteriophage T7 F10 and the F terminator (Studier et al., 1990), to regulate the expression of recombinant κ-casein. pS26 also contains the origin of replication and sequences encoding ampicillin resistance of the plasmid pBR322.

These three fragments were ligated and transformed into competent *E. coli* cells. Transformants harbouring the plasmid were isolated. The plasmid was analysed by restriction mapping and sequence analysis, designated pS415 (FIG. 7).

In order to construct an expression vector having a bacterial signal sequence in front of the sequence encoding the human mature κ-casein the following strategy was employed.

The selected bacterial signal sequence was the sequence encoding the signal peptide of heat stable enterotoxin II, STII, of *E. coli* (Picken et al., 1983). First, to achieve the major part of the human κ-casein cDNA, the same SphI and BamHI fragment from pS428 as above was used. Second, to provide a sequence encoding the natural amino terminal of human κ-casein and to allow the introduction, in translational frame, of the STII signal sequence in front of the κ-casein sequence, the following two oligonucleotides were synthesized: SYM 3240 5'-TATGCAGAGGTTCAAAACCAGAAACAACCAGCATG-3' (SEQ ID NO:12) and SYM 3241 5'-CTGGTTGTTTCTGGTTTTGAACCTCTGCA-3' (SEQ ID NO:13).

Third, in addition to provide regulatory elements, replication signals and selection markers as described above, the signal sequence was derived from NdeI and BamHI digestion of the plasmid pS28. This plasmid is similar to pS26 except that the STII signal sequence is introduced downstream of the T7 promoter.

The ligation and transformation of these three fragments resulted in the expression vector pS425 (FIG. 8). The pS425 vector was confirmed by sequence analysis and restriction mapping.

The expression vectors pS415 and pS425 were transformed into the *E. coli* strains BL21(DE3). BL21(DE3) pLysS and BL21(DE3)pLysE (Studier et al., 1990). The experiments were carried out as described by Studier et al., 1990. The results were analysed by SDS-PAGE and immuno-blot using the polyclonal antisera raised against human κ-casein (Example 2). The obtained results demonstrate that recombinant human κ-casein was efficiently expressed as a non-glycosylated protein of about 25 kDa, with the two different expression vectors, FIG. 9.

EXAMPLE 6

Expression of recombinant human κ-casein in mammalian cells

To produce recombinant human κ-casein in mammalian cell culture systems, the human κ-casein cDNA was introduced into an eukaryotic expression vector.

In summary, the vector contains human κ-casein cDNA under the control of the murine metallothioneine 1 (mMT-1) upstream regulatory element (Pavlakis and Hamer, 1983). mRNA processing signals are provided by a genomic fragment containing part of exon II, intron II, exon III and downstream elements of the rabbit β-globin gene which is inserted downstream of the κ-casein cDNA. This transcriptional unit was cloned into a vector containing the entire bovine papilloma virus type 1 (BPV-1) genome. Transcription was unidirectional for BPV-1 and the κ-casein transcriptional unit. For propagation and selection of plasmids in *E. coli*, the vector contains pML2d, a pBR322 derivative (Sarver et al., 1982).

The following strategy was employed to construct this expression vector. In order to modify the termini of κ-casein cDNA to facilitate further cloning, a PCR experiment using pS270 as template was carried out. Two synthetic oligonucleotides were designed for amplification of κ-casein cDNA containing a BglII site at the 5'-end and a SalI site at the 3'-end. SYM 2699 5'-GGGGTCGACTGGTGTTTTTATGCCGTAGGT-3' (SEQ ID NO:14) and SYM 2707 5'-GAGAGAAGATCTGACTGGCACGAGGAAAGG-3' (SEQ ID NO:15) The generated PCR DNA was digested with BglII and SalI, separated by agarose electrophoresis and isolated as a 592 bp fragment. This fragment was ligated with the following two fragments. First, the plasmid pS42 which contains the entire BPV-1 genome, the rabbit β-globin element, pML2d plasmid sequences and the mMT-1 upstream regulatory element was digested with SacI and SalI and a fragment of about 12.8 kb was isolated by agarose electrophoresis. The unique SacI site is localized in the mMT-1 sequence and the unique SalI site is localized upstream of the rabbit β-globin element. Second, a plasmid containing the entire mMT-1 gene, pS65, was digested with SacI and BglII to isolate the proximal part of the mMT-1 promoter element as a fragment of about 220 bp. These three fragments were ligated and transformed into competent *E. coli* cells. Plasmids of about 13.6 kb were isolated and prepared from transformants for restriction mapping and sequence analysis. Due to PCR generated mutations in the κ-casein cDNA sequence, it was necessary to combine sequences from two different plasmid isolates. Since the two isolates contain mutations at either side of the SphI site located in the κ-casein cDNA, the following method was used. The two plasmids were digested with SacI and SphI, and SphI and SalI, separately, to get correct κ-casein cDNA fragments. These two fragment were religated with the SalI and SacI fragment of pS42 as described above. Plasmid isolates were prepared from a number of transformants and subjected to sequence analysis and restriction mapping. The resulting expression vector was designated pS330 (FIG. 10.).

The expression vector pS330 was co-transfected with a vector encoding neomycin resistance gene driven by the Harvey Sarcoma virus 5'-Long terminal repeat (LTR) and simian virus 40 polyadenylation signals (Lusky and Botchan. 1984) into the murine cell line C127 (ATCC CRL 1616) and chinese hamster ovary (CHO) cell lines, according to the calcium-precipitation method (Graham and van der Eb, 1973). The cells were cultured in Ham's F12-Dulbecco's Modified Eagles Medium (DMEM) (1:1) supplemented with 10% fetal calf serum. Neomycin resistant cell clones were selected with 1.5 mg/ml (C127) or 0.5 mg/ml (CHO) of G418 (Gibco), and after 2–4 weeks resistant cell clones were isolated from the master plates and passaged for analysis.

Conditioned cell culture media and cells were analysed for production of recombinant human κ-casein by SDS-PAGE and immunoblotting using polyclonal antisera raised against human κ-casein (Example 2). To analyze expression, RNA was prepared from the cells (Ausubel et al., 1991) separated by agarose-formaldehyde gel electrophoresis and blotted to membranes for hybridization to labelled human κ-casein probes.

The results obtained show efficient expression of recombinant human κ-casein, FIG. 11.

EXAMPLE 7

Expression of recombinant human κ-casein in transgenic animals

To achieve stage- and tissue-specific expression in the lactating mammary gland in a transgenic animal of recombinant human κ-casein, to be able to harvest the recombinant protein from milk, the following strategies have been used.

Two plasmids containing murine Whey Acidic Protein (WAP) genomic fragments were obtained from Dr. Lothar Hennighausen (Campbell et al. 1984). The genomic fragments contain about 4.5 kb of upstream regulatory sequences, the entire transcribed region which consists of 4 exons and 3 introns, and about 1.6 kb of 3' flanking sequences.

To allow introduction of the κ-casein cDNA at the position of the unique KpnI site in WAP exon 1 this site was modified by insertion of a synthetic oligonucleotide linker at this position, SYM 2401 5'- CGTCGACGTAC-3' (SEQ ID NO:16), and SYM 2402 5'-GTCGACGGTAC-3' (SEQ ID NO:17), resulting in the addition of a new SalI site 3' of the original KpnI site. Before this linker was inserted, the naturally occurring unique SalI site in the third exon was destroyed by SalI digestion, blunted by fill-in reaction using Klenow enzyme and religation. The plasmid containing the unique KpnI and SalI sites in the first exon is designated pS314.

In order to modify the termini of κ-casein cDNA to facilitate introduction into this vector, a PCR experiment using pS270 as template was carried out. Two synthetic oligonucleotides were designed for amplification of κ-casein cDNA containing a KpnI site at the 5'-end and a SalI site at the 3'-end, SYM 2699 5'-GGGGTCGACTGGTGTTTTTATGCCGTAGGT-3' (SEQ ID NO:14) and SYM 2698 5'-GGTGGTACCATGAAGAGTTTTCTTCTAGTTG-3' (SEQ ID NO:18). The generated PCR DNA was digested with KpnI and SalI, separated by agarose electrophoresis and isolated as a 566 bp fragment. This KpnI and SalI fragment was ligated to KpnI and Sal digested pS314. Transformants were isolated and plasmids were prepared and analysed by restriction mapping and sequencing.

To allow the removal of plasmid sequences NotI linkers were inserted 5' and 3' of the WAP/κ-casein recombinant gene. The resulting expression vector is designated pS339 (FIGS. 12 and 13). Before injection of the expression vector into embryos, pS339 was digested with NotI and the WAP/κ-casein fragment was isolated by agarose electrophoresis, followed by electroelution of the DNA. The eluted DNA was ethanol precipitated and redissolved in 10 mM Tris (pH 7.5) and 0.1 mM EDTA for microinjection.

The experimental procedures employed to obtain transgenic animals are described in Hogan et al. 1986.

The isolated fragments were injected, at a concentration of 3 ng/ml, into the pronucleus of C57B1/6JxCBA/2J-$f_2$ embryos obtained from donor mice primed with 5 IU pregnant mare's serum gonadotropin and 48 hours later with 5 IU human chorion gonadotropin for superovulation. The C57B1/6JxCBA/2J-$f_2$ animals were obtained from Bomholtgaard Breeding and Research Center Ltd., Rv, Denmark. After collection of the embryos from the oviducts, they were separated from the cumulus cells by treatment with hyaluronidase in the medium M2 (Hogan et al. 1986). Following washing, the embryos were transferred to the medium M16 (Hogan et al. 1986) and kept in an incubator with 5% $CO_2$ atmosphere. The injections were performed in a microdrop of M2 under light paraffin oil using Narishigi hydrolic micromanipulators and a Nikon inverted microscope equipped with Nomarski optics. After injections healthy looking embryos were implanted into pseudopregnant C57B1/6JxCBA/2J-$f_1$ recipients given 0.37 ml of 2.5% avertin intra-peritoneally.

Transgenic mice were identified by analysis of DNA which has been prepared from excised tail samples. The tissue samples were incubated with proteinase K and phenol chloroform extracted. The isolated DNA was used in polymerase chain reactions with primers which amplify specific fragments if the heterologous introduced DNA representing the expression vector fragment is present. The animals were also analysed by DNA hybridization experiments to confirm PCR data and to test for possible rearrangements, structure of the integrated vector elements and to obtain information about the copy number of integrated vector elements.

In one set of experiment 11 mice were analyzed. The PCR primers used for this screening were SYM 2228 complementary to murine WAP sequence (5'-CTGTGTGGCAAGAAGGAAGTGTTGT-3' (SEQ ID NO:19) and SYM 2603 complementary to human κ-casein cDNA sequence (5'-GGTTTGGGCGACGTACCACA-3' (SEQ ID NO:20)). The position of the two PCR primers are indicated in FIG. 14. The expected size of PCR amplified DNA from animals harbouring pS339 vector is 486 bp. The analysis resulted into identification of two transgenic founder animals carrying the recombinant WAP/κ-casein gene of pS339 (FIG. 15), one male and one female.

The mice identified to carry pS339 vector DNA element, founder animals, were then mated and the F1 litter were analysed for transgenicity by the same procedures.

Milk samples were collected from female lactating animals injected with 2 IU oxytocin intraperitoneally, and 10 minutes later anaesthetized with 0.40 ml of 2.5% avertin intraperitoneally. A milk collecting device was attached to the nipple via a siliconized tubing and milk was collected into a 1.5 ml eppendorf tube by gentle massage of the mammary gland. The amount of milk varied, dependent of the day of lactation, between 0.01 and 0.5 ml per mouse and collection. The collected milk was analysed for the presence of recombinant human κ-casein. This was done by SDS-PAGE, transfer to nitrocellulose membranes and incubation with polyclonal antibodies generated against native human κ-casein. The obtained results demonstrated expression of recombinant human κ-casein in milk from transgenic mice, FIG. 16.

Stable lines of transgenic animals are generated.

In order to achieve high-level expression of recombinant human κ-casein in milk from transgenic animals using the genomic fragments containing intron sequences derived from the human κ-casein gene, the following expression vectors are constructed.

The first expression vector contains the entire sequences of intron 1,3, and 4 of the human κ-casein gene under transcriptional control of the murine WAP upstream regulatory sequences. The downstream regulatory sequences and mRNA processing signals are provided by the human κ-casein genomic fragment which extends about 4.5 kb downstream of exon 5. This expression vector construct is schematically illustrated in FIG. 17.

In summary, this expression vector is constructed as follows. Two synthetic oligonucleotides are synthesized extending from the BsaJI cleavage site located in exon 2 to the MnlI site located in exon 3. An EcoRI site is added upstream of the BsaJI site to facilitate subsequent cloning of this fragment; 5'-AATTCCCCTGGCATTAACCCTGCCTTTTTTG-3' (SEQ ID NO:21) and 5'-AAAAAAGGCAGGGTTAATGCCAGGGG-3' (SEQ ID NO:22). After annealing of these two synthetic oligonucleotides they are ligated with a isolated MnlI/HindIII 340 bp fragment drived from pS465, into EcoRI/HindIII digested pUC19. The cloned fragments are subjected to sequence analysis, and the insert is isolated as BsaJI/HindIII fragment. This fragment is then ligated to a 0.66 kb XbaI/BsaJI fragment isolated from pS460. The XbaIIBsaJI fragment from pS460 and the BsaJI/HindIII fragment is then cloned into XbaI/HindIII digested pUC19. From this plasmid a XbaI/HindIII fragment of about 1 kb is isolated, and ligated to the PCR fragment described below.

To introduce a KpnI site in the 5' untranslated leader sequence a PCR fragment containing exon 1 sequence and the intron 1 sequence extending to the XbaI site is generated. For this experiment two PCR primers are synthesized, 5'-CCGGTACCAAGACCTGACTGGCACGAGGA-3' (SEQ ID NO:23), and 5'-ATTCTAGACCAGGCCTTATCT-3' (SEQ ID NO:24). The resulting 0.77 kb fragment is then ligated to the 1 kb XbaI/HindIII described above. These two fragments are cloned into KpnI/HindIII digested pUC19. From the resulting plasmid a KpnI/HindIII fragment of about 1.8 kb is isolated which contains the 5'part of the κ-casein minigene.

In the next step, pS339 is digested with NotI and KpnI and the WAP upstream regulatory sequences is isolated as a fragment of about 4.5 kb. This WAP fragment is then ligated to the KpnI/HindIII 1.8 kb fragment containing the 5'part of κ-casein minigene, and cloned into a modified pUC19, pUC19-N, in which the EcoRI site has been changed to a NotI site. The resulting plasmid, designated pWAP/K1-5', contains the WAP 5'regulatory sequences in front of the p5'part of the κ-casein minigene as a NotI/HindIII fragment of about 6.3 kb.

To complete the final expression vector this 6.3 kb NotI/HindIII fragment is ligated to a SalI/partial HindIII digested fragment of about 7.8 kb drived from pS459, providing the 3' rest of the transcribed part and 3'flanking untranscribed sequences of the κ-casein minigene. These two fragments are then ligated into SalI/NotI digested pUC19-N. The resulting recombinant WAP/κ-casein minigene is shown in FIG. 18.

In the second expression vector the translational initiation located in exon 2 of the human κ-casein gene is ligated directly to the KpnI site located in exonI of the murine gene. The natural translational initiation of murine WAP is located just downstream of the KpnI site. Thus, it can be anticipated that the sequence around this position has evolved to provide optimal conditions for translation initiation. This recombinant gene is shown in FIG. 18.

The vector is constructed as follows. A PCR fragment containing a KpnI site direct upstream of the translation initiation codon, ATG, was generated by using the following synthetic oligonucleotides as primers; 5'-CCGGTACCATGAAGAGTTTTCTTCTAGTT-3' (SEQ ID NO:25), and 5'-TTAAGCTTTACTTATGTTTTCATT-3' (SEQ ID NO:26). The resulting 0.4 kb KpnI/HindIII fragment is then cloned into KpnI/HindIII digested pWAP/K1-5' (described above). The resulting plasmid, designated WAP/K2-5' is used to complete the final expression vector. The same strategy as described above is used. In summary, the 4.9 kb NotI/HindIII fragment derived from pWAP/K2-5' is ligated to a SalI/partial HindIII digested fragment of about 7.8 kb derived from pS459, providing the 3' rest of the transcribed part and 3'flanking untranscribed sequences of the κ-casein minigene. These two fragments are then ligated into SalI/NotI digested pUC19-N. The resulting recombinant WAP/κ-casein minigene variant is shown in FIG. 18.

These two κ-casein minigene fragments will also be cloned under transcriptional control of other upstream regulatory sequences derived from other mammal milk protein genes e.g. β-lactoglobulin and α-casein.

EXAMPLE 8

Genetic variants of human κ-casein

It is assumed that human κ-casein exists in a limited number of genetic variants. These variants will have a number of amino acid substitutions as compared to the amino acid sequence deduced from the cDNA sequence shown in SEQ ID NO:1. The assumption is based on the fact that most other species investigated to date do have genetic variants, but also on the discrepancies found between the obtained cDNA sequence (SEQ ID NO:1) and the genomic sequence as described in Example 4 and the partial sequence determined by Menon et al. Genetic variants, i.e. analogues of the DNA sequence shown in SEQ ID NO:1, may be isolated and characterized by the following procedure:

DNA is isolated from fresh human milk provided by donors with varying genetic background (ethnicity). Similarly, mRNA is isolated from fresh milk and cDNA is synthesized by use of the reverse transcriptase methodology. Using specific synthetic oligonucleotides, selected from regions flanking sequences with pronounced amino acid discrepancies, DNA fragments are synthesized by the use of the PCR technique. Synthesized DNA fragments are isolated from agarose gels and sequenced by the dideoxy chain-termination method.

EXAMPLE 9

In vitro maturation, fertilization and culture of bovine oocytes

Immature oocytes are obtained in large quantity (400–600/day) by aspirating follicles of ovaries obtained at abattoirs. Immature oocytes are cultures for a period in vitro before they are competent to be fertilized. Once "matured", oocytes are fertilized with sperm which has also been matured, or "capacitated" in vitro. The pronuclei of the fertilized oocyte is then injected with the transgene coding for the expression and secretion of human κ-casein. Zygotes resulting from this in vitro fertilization and microinjection are then cultured to the late morula or blastocyst stage (5–6 days) in medium prepared, or "conditioned" by oviductal tissue. Blastocysts are then transferred non-surgically to recipient bovine species for the balance of gestation or analyzed for integration of the transgene as described herein.

In vitro maturation (IVM)

Ovaries are obtained immediately after slaughter at local abattoirs and oocytes are recovered. Alternatively, oocytes are obtained from living bovine species by surgical, endoscopic, or transvaginal ultrasonic approaches. In all cases, oocytes are aspirated from ovarian follicles (2–10 mm diameter). After washing, oocytes are placed in a maturation medium such as a medium consisting of M199 supplemented with 10% fetal calf serum, and incubated for 24 hours at 39° C. (Sirard et al. (1988) *Biol. Reprod.* 39, 546–552).

In vitro fertilization (IVF)

Matured oocytes are fertilized with either fresh or thawed sperm. Sperm is prepared for fertilization by first obtaining a population of sperm enriched for motility by a "swim-up" separation technique (Parrish et al. (1986) *Theriogenology* 25, 591–600). Motile sperm is then added to a fertilization medium, consisting of a modified Tyrode's solution (Parrish et al. (1986) supra) supplemented with heparin to induce sperm capacitation (Parrish et al. (1988) *Biol. Reprod.* 38, 1171–1180). Capacitation constitutes the final sperm maturation process which is essential for fertilization. Sperm and oocytes are co-cultured for 18 hours. A useful feature of this IVF method is that (in the case of frozen sperm) consistent, repeatable results are obtained once optimal fertilization conditions for a particular ejaculate have been defined (Parrish et al. (1986) supra).

In vitro culture (IVC)

Conventional culture systems, which support development of murine, rabbit, or human ova, do not support development of bovine embryos past the 8–16 cell stage. This problem has been overcome by pre-conditioning culture media with oviductal tissue. Oviduct-conditioned medium will support bovine embryos past the 8–16 cell stage to the blastocyst stage in vitro (Eyestone and First (1989) *J. Reprod. Fert.* 85, 715–720).

Bovine embryos did not yield to attempts to culture them in vitro past the 8–16 cell "block" until Camous et al. (1984) *J. Reprod. Fert.* 72, 779–785 demonstrated cleavage to 216 cells when embryos were co-cultured with trophoblastic tissue.

The co-culture procedure was extended to oviductal tissue, based on the ability to homo- or hetero-oviducts to support development from zygote to blastocyst. Thus, bovine embryos co-cultured with oviductal tissue, or in medium conditioned by oviductal tissue, developed from zygote to blastocyst in vitro (Eyestone and First (1989) *J. Reprod. Fert.* 85, 715–720; Eyestone, W. H. (1989) "Factors affecting the development of early bovine embryos in vivo and in vitro," Ph.D. Thesis, University of Wisconsin). Blastocysts have been produced in this system after superovulation and artificial insemination, or by in vitro maturation (IVM), and fertilization (IVF) of immature oocytes. Blastocysts produced in this fashion resulted in pregnancies and live calves after transfer to recipient animals. The results obtained were as follows:

| Step | Efficiency (%) | Number (per 100) |
|---|---|---|
| IVM | 90 | 90 |
| IVF | 80 | 72 |
| IVc | 30 | 22 |
| Embryo transfer (% pregnant) | 50 | 11 |

Therefore, from an initial daily harvest of 500 oocytes, it is expected that approximately 55 pregnancies will result.

Preparation of oviduct tissue Co-culture and conditioned medium

1. Obtain oviducts after slaughter or by salpingectomy.
2. Harvest lumenal tissue by scraping intact oviduct gently with a glass slide.
3. Wash tissue 5 times in 10 ml modified tyrodes-hepes solution (Parrish et al. (1988) *Biol. Reprod.* 38, 1171–1180).
4. Resuspend final tissue pellet in M199+10% fetal calf serum at a ratio of 1 volume tissue:50 volumes of media.
5. Tissue suspension can be used for embryo co-culture.
6. Alternatively, media may be conditioned for 48 hours; after centrifuging the suspension, the supernatant may be used as embryo culture medium. Conditioned medium may be stored at −70° C., if desired. Conditioned medium should be used at full strength for embryo culture (no dilution) (Eyestone (1989) ibid).

EXAMPLE 10

Microinjection of human κ-casein transgene into bovine pronuclei

The DNA fragment containing the human κ-casein expression system is excised from the vector by digestion with the appropriate restriction enzyme(s) and separated on agarose gels. The fragment is purified by electroelution, phenol and chloroform extraction and ethanol precipitation (Maniatis et al.). The DNA fragment is dissolved in and dailyzed in 10 mM tris, 0.1 mM EDTA pH 7.2 at a concentration of 1 to 2 μg/ml. Microinjection needles are filled with the dialyzed DNA solution.

Before in vitro fertilization, cumulus cells are removed from the egg by either vortexing at maximum speed for 2 minutes or pipetting the eggs up and down several times in a standard micropipette. Bovine pronuclei are injected in principle as murine pronuclei (Hogan, B. et al. (1986) in: Manipulating the mouse embryo, Cold Spring Harbour Laboratory) with an additional centrifugation step in order to visualize the pronuclei. The injection takes place 18–24 hours after fertilization. The time varies depending on the bull used as a source of semen. Different batches of semen cause the nuclei to become visible at different times.

Bovine oocytes, matured and fertilized in vitro, are spun in an eppendorf tube in 1 ml of tyrodes-hepes solution (Parrish (1987)) at 14500 g for eight minutes (Wall et al. (1985) *Biol. Reprod.* 32, 645–651). The embryos are transferred to a drop of tyrodes-hepes solution on a microscope slide covered with paraffin oil. Using a hydraulic system the oocytes are fixed to the egg holder in such a way that both the pronuclei are visible (using interference-contrast or phase contrast optics). If necessary, the oocytes are rolled to change their position on the egg holder to visualize the pronuclei. The injection needle is brought into the same sharp focus of one of the pronuclei. The needle is then advanced through the zona pellucida, cytoplasm into the pronucleus. A small volume of 13 pl is injected (containing 20–100 DNA copies) into the pronucleus either by using a constant flow or a pulse flow (using a switch) of DNA solution out of the needle. Alternatively, two cell stage embryos are spun as described and the nuclei of both blastomers are injected as described. The injected embryos are then transferred to a drop of co-culture medium as described in Example 6 in order to develop to the morula or blastocyst stage.

EXAMPLE 11

Early detection of transgenesis with human κ-casein transgene

Upon the microinjection of a construct as described in Example 7, the oocyte is cultured. A proper site of each embryo is cleaved and subjected to lysis (King, D. et al. (1988) *Molecular Reproduction and Development* 1, 57–62), proteolysis (Higuchi, R. (1989) "Amplifications (A forum for PCR Users," 2, 1–3) and digestion. PCR is performed as described previously in Example 4 with sets of two primers, one in exon 3 (SYM 3120) (see Table 1) and the other in exon 4 (SYM 2887).

EXAMPLE 12

Production of human κ-casein in milk of bovine species

Bovine morula developed from microinjected oocytes are split according to the method of Donahue (Donahue, S. (1986) *Genetic Engineering of Animals*, ed. J. Warren Evans et al., Plenum). One half of the morula is kept in culture to develop into blastocysts. The other half is subjected to the DNA analysis as described in Example 8. When the result of this analysis is known, the morula kept in culture are developed into a blastocyst or as a source for nuclear transfer into enucleated zygotes. Blastocyst transfer into synchronized cows is performed according to the method of Betteridge (Betteridge, K. J. (1977) in: Embryo transfer in farm animals: a review of techniques and applications).

Human κ-casein is detected in the milk of lactating transgenic off-spring using the methods described in Example 8.

DEPOSITION

Plasmid DNA, designated pS 270 has been deposited in the collection of Deutsche Sammlung von Mikroorganismen und Zellkulturen GmbH, Mascheroder Weg 1 b, D-3300 Braunschweig, Germany, on Jan. 17, 1992 in accordance with the provision of the Budapest Treaty and has been identified there by the accession number DSM 6878.

Plasmid DNA, designated pS 459 and pS460 has been deposited in the collection of Deutsche Sammlung von Mikroorganismen and Zellkulturen GmbH, Mascheroder Weg 1 b, D-3300 Braunschweig, Germany, on Jan. 20, 1993 in accordance with the provision of the Budapest Treaty and has been identified there by the accession numbers DSM 7414 and DSM 7415.

Expression vectors designated pS 330, 339, 415 and 425 has been deposited in the collection of Deutsche Sammlung von Mikroorganismen and Zellkulturen GmbH. Mascheroder Weg 1 b, D-3300 Braunschweig, Germany, on Jan. 20, 1993 in accordance with the provisions of the Budapest Treaty and has been identified there by the accession numbers DSN 7410, DSM 7411, DSM 7412 and DSM 7413.

---

What is claimed is:

1. A transgenic non-human mammal whose germ cells and mammary gland cells contain an expression system comprising
   (a) a first DNA sequence coding on expression for a peptide comprising
      (i) amino acid sequence 21–182 of SEQ ID NO:2,
      (ii) an amino acid sequence differing from sequence (i) solely by one or more conservative amino acid substitutions,
      (iii) am amino acid sequence at least 85% identical to sequence (i),
      (iv) an amino acid sequence which is encoded by a DNA sequence having a coding strand which hybridizes to the complementary strand of the DNA sequence of SEQ ID NO:1 when hybridization is carried out at 67° C. in 2×SSC and final washing at 67° C. in 1×SSC,
      (v) an effective subsequence of a sequence according to (i) above, or
      (vi) an amino acid sequence which is at least 85% identical to a subsequence (v), said subsequence (v) and said sequence (vi) being at least 25 amino acids long,
   said peptide having a biological activity of human kappa casein, and, in the case of (v) or (vi) above, said activity including a non-nutritional biological activity of human kappa casein; and
   (b) a second DNA sequence preceding said first sequence and operably linked in phase thereto, said second DNA sequence encoding a secretory signal peptide functional in mammary gland cells; and
   (c) a promoter functional in said mammary gland cells, whereby said mammal, under conditions conducive to expression, expresses said peptide in a mammary gland of said mammal, and secretes said peptide, in milk produced by said mammary gland, at detectable levels.

2. A mammal according to claim 1 which is selected from the group consisting of mice, rats, rabbits, goats, sheep, pigs, llamas, camels and bovine species.

3. The mammal of claim 1 in which the promoter is a milk protein gene promoter.

4. The mammal of claim 1 in which said expression system further comprises at least one intron.

5. The mammal of claim 4 in which the intron is a kappa casein intron.

6. The mammal of claim 1 in which the peptide comprises the amino acid sequence 1–182 of SEQ ID NO:2.

7. The mammal of claim 1 wherein the biological activity is a nutritional activity.

8. The mammal of claim 1 wherein the biological activity is a non-nutritional activity.

9. The mammal of claim 1 wherein the biological activity is an antimicrobial activity.

10. The mammal of claim 1 wherein the biological activity is an opioid raptor-mediated activity.

11. The mammal of claim 1 wherein the biological activity is an immunostimulatory activity.

12. The mammal of claim 1 wherein the biological activity is a calcium binding activity.

13. The mammal of claim 1 wherein the biological activity is a micellar formation activity.

14. The mammal of claim 1 in which said peptide comprises sequence (i).

15. The mammal of claim 1 in which said peptide comprises sequence (ii).

16. The mammal of claim 1 in which said peptide comprises sequence (iii).

17. The mammal of claim 1 in which said peptide comprises sequence (iv).

18. The mammal of claim 1 in which said peptide comprises effective subsequence (v) of sequence (i).

19. The mammal of claim 18 in which said effective subsequence is at least five amino acids long.

20. The mammal of claim 18 in which said effective subsequence is at least 25 amino acids long.

21. The mammal of claim 1 in which said peptide comprises effective subsequence (v) of sequence (iii).

22. A method for producing a peptide which has a biological activity of human kappa casein, said method comprising
providing a transgenic mammal according to claim 1, expressing the peptide in a mammary gland of the mammal, and collecting peptide-containing milk selected by said gland.

23. The method of claim 22 in which said peptide comprises sequence (i).

24. A method for producing a transgenic non-human mammal capable of expressing a peptide which has a biological activity of human κ-casein, said method comprising chromosomally incorporating a DNA sequence encoding the peptide into the genome of a non-human mammal so said genome comprises an expression system comprising
   (a) a first DNA sequence coding on expression for a peptide comprising
      (i) amino acid sequence 21–182 of SEQ ID NO:2,
      (ii) an amino acid sequence differing from sequence (i) solely by one or more conservative amino acid substitutions,
      (iii) am amino acid sequence at least 85% identical to sequence (i),
      (iv) an amino acid sequence which is encoded by a DNA sequence having a coding strand which hybridizes to the complementary strand of the DNA sequence of SEQ ID NO:1 when hybridization is carried out at 67° C. in 2×SSC and final washing at 67° C. in 1×SSC,
      (v) an effective subsequence of a sequence according to any of sequences (i) or (iii) above, or
      (vi) an amino acid sequence which is at least 85% identical to a subsequence (v), said subsequence (v) and said sequence (vi) being at least 25 amino acids long,
   said peptide having a biological activity of human kappa casein, and, in the case of (v) or (vi) above, said activity including a non-nutritional biological activity of human kappa casein; and
   (b) a second DNA sequence preceding said first sequence and operably linked in phase thereto, said second DNA sequence encoding a secretory signal peptide functional in mammary gland cells; and
   (c) a promoter functional in said mammary gland cells, wherein said mammal, under conditions conducive to expression, expresses said peptide in a mammary gland of said mammal, and secretes said peptide, in milk produced by said mammary gland, at detectable levels.

25. A transgenic non-human mammal which is a founder mammal prepared by the method of claim 24, or progeny of said founder mammal, wherein said transgenic mammal, under conditions conductive to expression, expresses said peptide in a mammary gland of said mammal, and secretes said peptide, in milk produced by said mammary gland, at detectable levels.

26. A method for producing a human infant formula comprising a peptide which has a biological activity of human κ-casein comprising
providing a transgenic nonhuman mammal according to claim 1,
obtaining expression of the peptide by said transgenic non-human mammal,
harvesting and optionally purifying the peptide expressed by said transgenic non-human mammal, and
formulating a human infant formula with said peptide, said infant formula further comprising at least one other infant formula constituent selected from the group consisting of other milk proteins, lipids, carbohydrates, vitamins, minerals and other nutrients essential to meet the nutritional requirements of a human infant.

* * * * *

UNITED STATES PATENT AND TRADEMARK OFFICE
CERTIFICATE OF CORRECTION

PATENT NO. : 6,222,094 B1
DATED : April 24, 2001
INVENTOR(S) : Lennart Hansson, Mats Strömqvist, Sven Bergström, Olle Hernell and Jan Törnell It is certified that error appears in the above-identified patent and that said Letters Patent is hereby corrected as shown below:

Title page,
Item [30], delete "(SE)" and insert therefor -- (DK) --.

Column 1,
Lines 7, 12, 17, 20 and 25, delete "ε-casein" and insert therefor -- κ-casein --.

Column 2,
Lines 54, 55, 57, 59, 62, 64 (both occurrences) and 65, delete "ε-casein" and insert therefor -- κ-casein --.

Column 3,
Lines 1, 13, 31, 33, 34, 35, 36, 53, 58 and 63, delete "ε-casein" and insert therefor -- κ-casein --.
Line 13, delete "ε-caseinoglycopeptide" and insert therefor -- κ- caseinoglycopeptide --

Column 4,
Lines 34, 63 and 67, delete "ε-casein" and insert therefor -- κ-casein --.

Column 5,
Lines 23, 28, 31, 34, 37, 40 (both occurences), 42, 46, 51, 55 and 57, delete "ε-casein" and insert therefor -- κ-casein --.

Column 6,
Lines 2, 3, 6, 10, 12, 21 and 54, delete "ε-casein" and insert therefor -- κ-casein --.

Column 7,
Lines 33, 35, 36, 37, 50, 52, 55 and 67, delete "ε-casein" and insert therefor -- κ-casein --.

Column 8,
Lines 4 and 17, delete "ε-casein" and insert therefor -- κ-casein --.

Column 12,
Lines 8, 15, 20, 21, 23, 50 and 54, delete "ε-casein" and insert therefor -- κ-casein --.

UNITED STATES PATENT AND TRADEMARK OFFICE
CERTIFICATE OF CORRECTION

PATENT NO.   : 6,222,094 B1
DATED        : April 24, 2001
INVENTOR(S)  : Lennart Hansson, Mats Strömqvist, Sven Bergström, Olle Hernell and Jan Törnell It is certified that error appears in the above-identified patent and that said Letters Patent is hereby corrected as shown below:

Column 13,
Lines 19, 33, 64 and 67, delete "ε-casein" and insert therefor -- κ-casein --.

Column 14,
Lines 4, 16, 35, 39, 41 and 43, delete "ε-casein" and insert therefor -- κ-casein --.

Column 77,
Line 51, delete "am" and insert therefor -- an --.

Column 78,
Line 59, delete "1-182" and insert therefor -- 21-182 --.
Line 67, delete "raptor" and insert therefor -- receptor --.

Column 79,
Line 16, delete "of sequence (i)".
Line 22, delete "(v) of sequence (iii)" and insert therefor -- (vi) --.
Line 29, delete "selected" and insert therefor -- secreted --.
Line 44, delete "am" and insert therefor -- an --.

Column 80,
Line 14, delete "and".
Line 27, delete "wherein" and insert therefor -- whereby --.

Signed and Sealed this

Seventh Day of May, 2002

*Attest:*

*Attesting Officer*

JAMES E. ROGAN
*Director of the United States Patent and Trademark Office*